US012168802B2

(12) United States Patent
Lenardo et al.

(10) Patent No.: US 12,168,802 B2
(45) Date of Patent: Dec. 17, 2024

(54) METHODS OF DIAGNOSING AND TREATING CD55 DEFICIENCY, HYPERACTIVATION OF COMPLEMENT, ANGIOPATHIC THROMBOSIS AND PROTEIN LOSING ENTEROPATHY (CHAPLE), A NEWLY IDENTIFIED ORPHAN DISEASE

(71) Applicant: The United States of America, as represented by the Secretary, Dept. of Health and Human Services, Bethesda, MD (US)

(72) Inventors: Michael J. Lenardo, Bethesda, MD (US); Helen Su, Bethesda, MD (US); Ahmet Oguzhan Ozen, Istanbul (TR); William Andrew Comrie, Rockville, MD (US); Kaan Boztug, Vienna (AT); Rico Chandra Ardy, Vienna (AT)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 18/154,745

(22) Filed: Jan. 13, 2023

(65) Prior Publication Data

US 2023/0295730 A1 Sep. 21, 2023

Related U.S. Application Data

(62) Division of application No. 16/333,561, filed as application No. PCT/US2017/051413 on Sep. 13, 2017, now abandoned.

(60) Provisional application No. 62/394,630, filed on Sep. 14, 2016.

(51) Int. Cl.

| | |
|---|---|
| ***A61K 39/395*** | (2006.01) |
| ***A61K 38/12*** | (2006.01) |
| ***C12Q 1/6827*** | (2018.01) |
| ***C12Q 1/6851*** | (2018.01) |
| ***C12Q 1/6883*** | (2018.01) |
| ***G01N 33/68*** | (2006.01) |
| *C07K 16/40* | (2006.01) |

(52) U.S. Cl.

CPC ............ *C12Q 1/6883* (2013.01); *A61K 38/12* (2013.01); *C12Q 1/6827* (2013.01); *C12Q 1/6851* (2013.01); *G01N 33/6893* (2013.01); *C07K 16/40* (2013.01); *C12Q 2600/156* (2013.01)

(58) Field of Classification Search

None

See application file for complete search history.

(56) References Cited

U.S. PATENT DOCUMENTS 4,496,553 A * 1/1985 Halskov ............... A61K 9/2081 514/166

FOREIGN PATENT DOCUMENTS

WO 2009029669 A1 3/2009

OTHER PUBLICATIONS

Lowe, Derek; "Not alphafold's fault." Blog "In the pipeline" entry of Sep. 7, 2022.*

Aomatsu, Tomoki et al; "Neutralization of complement component c5 ameliorates the development of dextran sulfate sodium colitis in mice." J. Clin. Biochem. Nutr. (2013) 52(1) p. 72-75.*

Chang, Regina; "Identifying inflammatory bowel disease patients in tcga database." Master's thesis (Oct. 2016) Georgia State University.*

Brodsky, R.A.: Paroxysmal nocturnal hemoglobinuria, Blood, vol. 124, No. 18, Oct. 30, 2014, pp. 2804-2811, XP055430451, US ISSN: 0006-4971, DOI:10.1182/blood-2014-02-522128.

Cazander, Gwendolyn et al: "Complement activation and inhibition in wound healing." Clin. Develop. Immunol. (2012) article 534291, doi: 10.1155/2012/534291.

International Search Report and Written Opinion for PCT Application No. PCT/US2017/051413, dated Feb. 5, 2018.

Habtemariam, Solomon; "Natural inhibitors of tumor nectosis factor alpha production, secretion and function." Planta Medica (2000) 303-313.

Hue-Roye K, et al: "Three new high-prevalence antigens in the Cromer blood group system", Transfusion., vol. 47 No. 9, Sep. 2007, pp. 1621-1629, XP055429921, US ISSN: 0041-1132, DOI:10.1111/j.1537-2995.2007.01333x.

(Continued)

*Primary Examiner* — Fred H Reynolds

(74) *Attorney, Agent, or Firm* — Klarquist Sparkman, LLP

(57) ABSTRACT

Disclosed herein are methods of diagnosing, and treating and/or preventing CD55-deficiency, hyperactivation of complement, angiopathic thrombosis and protein-losing enteropathy (CHAPLE). The method of diagnosing includes: providing a sample from a patient; performing an assay detecting at least one of at least one mutation in a DNA sequence of a CD55 gene, at least one mutation in a RNA sequence of a CD55 transcript, at least one mutation in a DNA sequence of a CD55 complementary-DNA (cDNA), CD55 protein, CD55 protein binding, complement deposition or combination thereof, and diagnosing the patient with CHAPLE. The method of treating and/or preventing at least one symptom of CHAPLE includes: administering an effective amount of a composition comprising at least one complement inhibitor to a subject in need thereof, wherein the composition is effective in treating or preventing at least on symptom of CHAPLE. The disclosure further relates to compositions effective at treating and/or preventing CHAPLE.

10 Claims, 35 Drawing Sheets

Specification includes a Sequence Listing.

(56) References Cited

OTHER PUBLICATIONS

Kavanagh, D et al: The decay accelerating factor mutation 1197V found in hemolytic uraemic syndrome does not impair complement regulation. Mol Immunol. 44(12), Apr. 17, 2007, pp. 3162-3167. doi: 10.1016/j.molimm.2007.01.036.
Kim, Hanguen et al: "Inhibition of C3 Convertase Activity by Hepatitis C Virus as an Additional Lesion in the Regulation of Complement Components." PLoS ONE (2014) 9(7) e101422. doi:10.1371/journal.pone.0101422.
Kurolap, Alina et al: "Loss of CD55 in Eculizumab-Responsive Protein-Losing Enteropathy." N Engl J Med. Jul. 6, 2017;377(1):87-89. doi:10.1056/NEJMc1707173.
Li, Xiao et al: Somatostatin regulates tight junction proteins expression in colitis mice. Int J Clin Exp Pathol. Apr. 15, 2014;7(5):2153-62.
Lin, F. et al: "Decay-Accelerating Factor Deficiency Increases Susceptibility to Dextran Sulfate Sodium-Induced Colitis: Role for Complement in Inflammatory Bowel Disease," The Journal of Immunology, vol. 172, No. 6, Mar. 15, 2004 (Mar. 15, 2004), pp. 3836-3841, XP055427415, US ISSN: 0022-1767. doi.org/10.4049/jimmunol.172.6.3836.
Lowe, Derek: "More magic mehtyls, please." Blog "In the pipeline" entry of Oct. 30, 2013.
Lv, Ruxi et al: "Tumor necrosis factor alpha blocking agents as treatment for ulcerative colitis or refractory to conventional medical therapy: a meta-analysis." PLoS ONE (2014) 9(1) e86692. doi: 10.1371/journal.pone.0086692.
Mawarti, Herin et al: "The effects of aloe vera on tnf alpha levels, the percentage of nk cells ind th 17 cells in rat that received izoniazid and rifampycin." Med. Arch. (2017) 71(5) p. 308-311. doi: 10.5455/medarh.2017.71.308-311.
Morgan, B. Paul et al: "Complement, a target therapy in inflammatory and degenerative diseases." Nat. Rev. Drug Discov. Dec. 2015;14(12): p. 857-77. doi: 10.1038/nrd4657.
Ozen, A. et al: "CD55 Deficiency, Early-Onset Protein-Losing Enteropathy, and Thrombosis," New England Journal of Medicine, the—NEJM, Massachusetts Medical Society, US, vol. 377, No. 1, Jul. 6, 2017, pp. 52-61, XP009501678, ISSN: 1533-4406, DOI: 10.1056/NEJMOA1615887.
Serruto, Davide et al. "Molecular mechanisms of complement evasion: learning from staphylococci and meningococci." Nature Reviews Microbiology 8.6 (2010): 393-399. doi: 10.1038/nrmicro2366.
Chiu et al., "Antibody structure and function: the basis for engineering therapeutics," *Antibodies* (*Basel*) 8(4):55, E-pub Dec. 3, 2019.
"Complement C5 Antibodies," ThermoFisher Scientific Catalog, Accessed https://www.thermofisher.com/antibody/primary/target/complement%20c5, Retrieved May 15, 2024.
Hoy, "Pozelimab: First Approval," *Drugs* 83(16):1551-1557, Nov. 2023.
Kolker, "Antibodies and the written description requirement of 35 U.S.C. 112(a)," USPTO presentation, Sep. 17, 2020.
Ozen et al., "CD55 deficiency, early-onset protein-losing enteropathy, and thrombosis," *The New England Journal of Medicine* 377(1):52-61, E-pub Jun. 28, 2017.
Ozen, "CHAPLE syndrome uncovers the primary role of complement in a familial form of Waldmann's disease," *Immunological Reviews* 287(1):20-32, Jan. 2019.
Ozen et al., "Broadly effective metabolic and immune recovery with C5 inhibition in CHAPLE disease," *Nature Immunology* 22(2):128-139, Feb. 2021.
Ozen et al., "Evaluating the efficacy and safety of pozelimab in patients with CD55 deficiency with hyperactivation of complement, angiopathic thrombosis, and protein-losing enteropathy disease: an open-label phase 2 and 3 study," *Lancet* 403(104272):645-656, E-pub Jan. 23, 2024.

* cited by examiner

FIG. 2A

Family 1 and Family 7 Mutation c.149_150delAAinsCCTT
p.Glu50Alafs*12

*mRNA alignment*

```
CD55 WT      101 GTGACTGTGGCCTTCCCCCAGATGTACCTAATGCCCAGCCAGCTTTGGAAGGCCGTACAAGTTTCCCGAGGATACTGTAATAACGTACAAATGTGAAGA 200 - SEQ ID NO: 24
CD55 (1,7)   101 GTGACTGTGGCCTTCCCCCAGATGTACCTAATGCCCAGCCAGCTTTGGCCTTGGCCGTACAAGTTTTCCCGAGGATACTGTAATAACGTACAAATGTGAA 200 - SEQ ID NO: 25
                 ***********************************************          *    **  * *   *  *   *     * *  **   *
```

*protein alignment*

```
CD55 WT      1 MTVARPSVPAALPLLGELPRLLLLVLLCLPAVWGDCGLPPDVPNAQPALEGRTSFPEDTVITYKCEESFVKIPGEKDSVICLKGSQWSDIEEFCNRSCEV 100 - SEQ ID NO: 26
CD55 (1,7)   1 MTVARPSVPAALPLLGELPRLLLLVLLCLPAVWGDCGLPPDVPNAQPALALAVQVFPRIL**RTNVKKAL*KFLARRTQ*SALRAVNGQILKSSAIVAAR 100 - SEQ ID NO: 27
                 ***********************************************          .             .       . .   . * .          .    .
```

FIG. 2B

Family 2, Family 3 and Family 5 Mutation c.109delG
p.Gly37Alafs*24

*mRNA alignment*

```
CD55 WT        101 GTGACTGTGGCCTTCCCCCAGATGTACCTAATGCCCAGCCAGCTTTGGAAGGCCGTACAAGTTTCCCGAGGATACTGTAATAACGTACAAATGTGAAGA 200 - SEQ ID NO: 28
CD55 (2,3,5)   101 GTGACTGTGCCTTCCCCCAGATGTACCTAATGCCCAGCCAGCTTTGGAAGGCCGTACAAGTTTCCCGAGGATACTGTAATAACGTACAAATGTGAAGAA 200 - SEQ ID NO: 29
                   *********  * * ****        *   *    **   *     ** * * * *      *   *** **   *         * *       **     * *
```

*protein alignment*

```
CD55 WT        1 MTVARPSVPAALPLLGELPRLLLLVLLCLPAVWGDCGLPPDVPNAQPALEGRTSFPEDTVITYKCEESFVKIPGEKDSVICLKGSQWSDIEEFCNRSCEV 100 - SEQ ID NO: 30
CD55 (2,3,5)   1 MTVARPSVPAALPLLGELPRLLLLVLLCLPAVWGDCAFPQMYLMPSQLWKAVQVFPRIL**RTNVKKAL*KFLARRTQ*SALRAVNGQILKSSAIVAARC 100 - SEQ ID NO: 31
                   ************************************ *              **          . *      .  * . .   .    .    .  . .
```

FIG. 2C

Family 6 Mutation c.287-1G>A

This is a splice acceptor site mutation for Exon 3, start of Exon 3 shown in blue

*Genomic Sequence Alignment*

```
CD55 Gene WT     8071 TTTGTTAATACTTTTAGGTAGCTGCGAGGT 8100 - SEQ ID NO: 32
CD55 Gene (6)    8071 TTTGTTAATACTTTTAAGTAGCTGCGAGGT 8100 - SEQ ID NO: 33
                      **************** *************
```

FIG. 2D

Family 4 Mutation c.800G>C p.Cys267Ser

*mRNA alignment*

```
CD55 WT     701 GAATAATTCAAGGGGAACGTGACCATTATGGATATAGACAGTCTGTAACGTATGCATGTAATAAAGGATTCACCATGATTGGAGAGCACTCTATTTATTG 800 - SEQ ID NO: 34
CD55 (4)    701 GAATAATTCAAGGGGAACGTGACCATTATGGATATAGACAGTCTGTAACGTATGCATGTAATAAAGGATTCACCATGATTGGAGAGCACTCTATTTATTC 800 - SEQ ID NO: 35
                ***************************************************************************************************
```

*protein alignment*

```
CD55 (WT)   201 SSFCLISGSSVQWSDPLPECREIYCPAPPQIDNGIIQGERDHYGYRQSVTYACNKGFTMIGEHSIYCTVNNDEGEWSGPPPECRGKSLTSKVPPTVQKPT 300 - SEQ ID NO: 36
CD55 (4)    201 SSFCLISGSSVQWSDPLPECREIYCPAPPQIDNGIIQGERDHYGYRQSVTYACNKGFTMIGEHSIYSTVNNDEGEWSGPPPECRGKSLTSKVPPTVQKPT 300 - SEQ ID NO: 37
                ******************************************************************.*********************************
```

FIG. 4

Table 2. Clinical and immunological characteristics of patients with CD55 deficiency

| **Patient ID.** | **P 1.1** | **P 2.1** | **P 3.1** | **P 4.1** | **P 4.2** | **P 4.3** | **P 5.1** | **P 5.2** | **P 6.1** | **P 7.1** |
|---|---|---|---|---|---|---|---|---|---|---|
| **Demographics** | | | | | | | | | | |
| Current age (yrs) and gender | 8, F | 23, F | 17, M | 3, F | 17, M | 18, M | 11, M | 13, F | 15, M | 4, F |
| Age of Onset | 6 months | 6 years | 27 months | 1 year | Toddler age | No complaints | 1 year | 10 years | 1.5 years | 1 year |
| **Disease manifestations** | | | | | | | | | | |
| Facial and extremity Edema | **Yes** | Yes | **Yes** | **Yes** | **Yes** | None | Yes | Yes | **Yes** | **Yes** |
| Bloody Diarrhea and Vomiting | **Yes** | Yes | No | **Yes** | None | None | **Yes** | No | Yes | Yes |
| Serum Proteins | | | | | | | | | | |
| Albumin | **2.3** (3.5-5.4) | **1.9** (3.5-5.4) | **1.0** (3.5-5.4) | **1.4** (3.5-5.4) | **3.2** (3.5-5.4) | **4.5** (3.5-5.4) | **2.2** (3.5-5.4) | **2.0** **(3.8-5.4)** | **0.8** **(3.5-5.4)** | **1.6** (3.5-5.4) |
| IgG | **150** (745-1804) | **186** (876-2197) | **143** (549-1584) | **143** (604-1941) | **321** (913-1894) | **699** (913-1894) | **184** (886-2530) | **493** (976-2120) | **157** (604-1941) | **240** (648-2010) |
| IgM | **33** (78-261) | **49** (75-440) | 39.2 (23-259) | **44.9** (71-235) | **49** (88-322) | **78** (88-322) | 75.5 (67.7-527) | **96.8** (78.8-370) | **24** (71-235) | **39** (52-297) |
| IgA | **28** (57-282) | **53** (100-447) | **21.3** (61-348) | **10.5** (26-296) | **43** (135-378) | **146** (135-378) | **151** (27-198) | **11** (97.8-456) | **25** (26-296) | **35** (44-244) |
| GI Malabsorption features | | | | | | | | | | |
| Growth retardation | **Yes** | **Yes** | | **Yes** | **No** | **No** | **Yes** | **Yes** | **Yes** | **Yes** |
| Anemia | **Yes** | **Yes** | **Yes** | **Yes** | **No** | **No** | **Yes** | **Yes** | **Yes** | **Yes** |

FIG. 4 Continued

| | | | | | | | | | | |
|---|---|---|---|---|---|---|---|---|---|---|
| Micronutrient def. | Low vit D, vit B12 | Low iron, ferritin, folate, vit B12 | Low vit B12, calcium | Low vit B12 | Low ferritin | Low vit B12 | Low iron, vit B12, calcium, and other nutritional deficiencies | Low iron, vit B12, and other nutritional deficiencies | Low calcium, iron, ferritin, folate, magnesium, vit D | Low iron, ferritin, vit D, and vit B12 |
| Demonstrated Lymphang-iectasis | **No** | **Yes** | **No** | **No** | **N/A** | **N/A** | **Yes** | **Yes** | **Yes** | **Yes** |
| GI exam; endoscopy and imaging | Mucosal ulcers in terminal ileum, lymphoid aggregates ;intestinal wall thickening on abdominal CT | Mucosal ulcers in terminal ileum, lymphoid aggregates ;cryptitis, crypt. abscesses, villous blunting, Dilation of intestinal segments on CT | Mucosal ulcers, cryptitis and crypt abscesses, lymphoid infiltration | Lymphoid aggregates in the colonic biopsies | **N/A** | **N/A** | Ulceration, epithelial erosion, chronic inflammation, and dilated lymphatics in the small intestine mainly jejunum | Ectatic lymphatic vessels in submucosal and subserosal small bowel. | Dilated lymphatic vessels in duodenum, normal mucosa | Non-specific duodenitis, intestinal lymphang-iectasia in duodenum |
| Respiratory manifestations | Recurrent infections | Recurrent pneumonia chronic coughing, and hemoptysis bronch-iectasis resolved with IVIG Rx | None | None | None | None | None | None | Recurrent cough, fibrotic changes in lung CT | Recurrent pneumonia |

FIG. 4 Continued

| | | | | | | | | | | |
|---|---|---|---|---|---|---|---|---|---|---|
| Vascular features | None | None | None | None | None | None | Multiple thombi in mesenteric and hepatic veins and right atrium. | None | Multiple thombi in IVC, heart and pulmonary arteries | None |
| Other systemic features | Hypo-thyroidism, osteopenia finger clubbing, increased fecal $\alpha$-1 antitrypsin level | Hypo-thyroidism, finger clubbing | Arthralgia | Thrombo-cytosis, finger clubbing, transient proteinuria at the onset of symptoms | None | None | None | None | Low Complement C3, clubbing, transient proteinuria at the onset of symptoms. Hepatos-plenomegaly, left renal agenesis, c5-6 hemi-vertebrae, develop-mental delay | None |
| **Medications** | | | | | | | | | | |
| | | | | | | | | | | |

FIG. 4 Continued

| | | | | | | | | | | |
|---|---|---|---|---|---|---|---|---|---|---|
| Supportive Rx | Vitamin B12 and -D replacement, intermittent infusions of albumin, enteral feeding, omega-3 fatty acids. | Vitamin B12 replacement, intermittent infusions of albumin, enteral feeding, folate, iron. Erythrocyte transfusion for one. | Vitamin B12 replacement, folate, calcium | Vitamin B12 replacement, intermittent infusions of albumin | No treatment | Vitamin B12 replacement | Albumin infusion one every two weeks. Medium chain triglyceride and vitamin supplemental diet | Albumin infusion one every two weeks | Albumin infusion multi-vitamin. Calcium supplementation, vit D, iron, Mg, medium chain fatty acids, zinc, enteral feeding | Albumin infusion, vit D, vit B12, erythrocyte transfusion for once |
| **IBD Rx** | Corticosteroids mesalazine, azathioprine, anti-TNF-a | Corticosteroids mesalazine, azathioprine, anti-TNF-a | Corticosteroids mesalazine, azathioprine | None | None | None | None | None | None | None |

FIG. 4 Continued

| | | | | | | | | | | |
|---|---|---|---|---|---|---|---|---|---|---|
| **Other Rx** | IVIG+ cotrimox-azole, Thyroxin | IVIG+ cotrimox-azole, Thyroxin | Colchicine | None | None | None | Octreotide, low molecular weight heparin | None | Cortico-steroids for lymphang-iectasia, octreotide, low molecular weight heparin, aspirin, Laroxyl for headache | Octreotide, cotrimox-azole, IV antibiotics for pneumonia |
| **Clinical Outcome** | | | | | | | | | | |
| | PLE persists, with growth retardation, frequent albumin Rx | Underwent surgery for intestinal obstruction. In the short term follow-up post-surgery normal albumin levels | PLE persists, albumin Rx | PLE persists, retarded growth, frequent albumin Rx | Asympto-matic, with sub-clinical hypo-protein-emia | Asympto-matic, mild hypo-gamma-globulin-emia | Resection of localized lymphang-iectasis led to an intermittent recovery of PLE, which recurred | Hypo-albumin-emia alleviated after surgical resection of lymphang-iectatic segments | Severe PLE, frequent albumin Rx, unstable GI disease and thrombosis | PLE persists, impaired growth and lung infections, frequent albumin Rx |

SEQUENCE LISTING

```
Sequence total quantity: 48
SEQ ID NO: 1            moltype = DNA  length = 46495
FEATURE                 Location/Qualifiers
source                  1..46495
                        mol_type = genomic DNA
                        organism = Homo sapiens
SEQUENCE: 1
cctgaagaac tcatgtataa gaaatgggag agtccactca tttgttttca tttattaaaa  60
aataccctta ttctgtgaag cagaattacc tgtatttgca gctgcatgac aaaaatgcct  120
caatataaag ctccccccaa cccccacccc ccgcccattg gctattttaa gataagttgg  180
caataaattt aggctgagtt agaatgtaaa tatgaaatag actggttcct cagatgtgag  240
gcatagatag gcacattaca tactttggta gcatagagga aggtaccagg tatgatgcaa  300
tggcaaggga gattttctgg aggaatgttg cctggccagt ctaacagagg tgttaagatc  360
ctaagcacta gttctactgc cagcaagcca tgtggtttgg ggctagtttc ttaacttccc  420
taaacaccag ctggttcact tgcaatgagg gtgataatat ttgctcacag ttttgtattc  480
cttggctttc aagaaattgc acaatcctct ttcctttcca ctaccttctc ctttcccttt  540
ctctgtcatt tgtactttct aacgtggggc tcctcaagtc tcacaccttg ggcttctcta  600
tttccacatg ctatgctccc ttggttcaaa ccttgcctgc agtcacatct ctacccactc  660
cacctcaatc ttgcctccgt ttcaatcgca tgctggacat ttccacgtag acactctgcc  720
aaggcatttg aaattcaaca agtgtaaagc tgaatatgga tagttctttt aaatagggct  780
gctaatctca caaactccaa acttccgagt cctcttcaac atctttttcc ccactgttcc  840
ttatctaatc agttgccaaa ttctgtggct tattactttg aaacttgttt ggtcagagca  900
ggaatggaaa ttcaaaagtc tataataatt gtgtcaggag ttttacagag caacaggact  960
ggaactcctt aatatagatt tattaatttt aaaactaaaa gacattttttg ttctctaaac  1020
acctggactg ttgtaattag ctaaattgga tctttgctta cacagccatt cccattccag  1080
catcttagat gcaaattcca aattacccag gtgcttcctc cttacaagtg tcaaccgtcc  1140
tttaatgctt ctgaatggtg taaaaggcac aggccttgcc tttaaggctc tctcaaatct  1200
ctttccagcc tctcttaccc tcttgttcca ttgccattgc ctcaattcag ttctccatac  1260
tctccctaaa ctaaactcct tactattcct ggaatcaaca ggactgaccc caaacctttg  1320
ttcgtatctc atctcttttc ctatttttgc cctattgcat tgacacttgt catatttagt  1380
tgaatcactg ggcctttagc cttccccgct ccaattacca cactcccttc tttcctttct  1440
gaagccccat accactttgg ttgtgatatt tgtatagcat ttatcatgga aaacctccct  1500
actagattgt agattctcaa acacaagtat tgacacttag tgggtttctg tatactaggg  1560
aagtttatta aacagtcttt gatttagtca ttgtatggtt cctgggataa gagtaagaac  1620
cgtggtccct tgctctgtca aaatcataaa cctattttct ttgtattttg acttaattac  1680
ataagcttgt tttggattgg aaggtctata gagactattt tagtgccaaa tgctatttaa  1740
tcaatgcaga aataagccct tgagaggtgc agtgactcag ctgaggacac actgatagtt  1800
tctggtagat aagtatgaag ccttggaact acttctcata tcataagccc ctgggttccc  1860
```

-continued

```
aaatcacctc cccaagtacc taattcatca tcctctgcat acaagaaatt tttgctcatt  1920
ccaataaaaa gaatgtagta cggcaggaca ggagaagtac aggttttgga atcaaactag  1980
gtttagattc tgacctggtc gctagttagt gcatgggctt tggtaaacag cctctcagcc  2040
tgtttccttg tctgcaaaat atggatagtt atcttcactt catgaagttg tgttggtgaa  2100
atggtataat gtgtataaag caactggaac acaacaaatg aggccattta tttaaaataa  2160
tctttagtaa gttataaatt cacatatttg ctttttttctg aggaatgctt agattttatc  2220
atagatctct tttctaaatt gagtaaatac atagtggatt tctttgtttc cttcccctca  2280
gaatgttgaa atttggctga ttgtaactat tacttaagac tctatccagt aattgttcgt  2340
aaaatttctt ttcttttttt tttttgaga cggagttttg ctctcgtccc ccaggctgga  2400
gtgcaatggc gcgatcttgg ctcactgcaa cctccgcctc ccaggttcaa gtgattctcc  2460
cgcctcagcc tcccaagtag ctgggattac aggcacctgc cacaacgccc agccaatttt  2520
tgtattttta gtagagacgg ggtttcacca tgttggccag gctagtctgg aactcctgac  2580
ctcaggtgat cctcctgcct tggcctccca aagtgctgag attacaggcg tgagccacca  2640
cgcccggcca aaatttcctt ttaaaaaaag ttattgccaa taactaagta tgctggaagg  2700
tgaatgctta ggacatttag tgtcactgag ctgtgtgata gagataatat ttttgacact  2760
ttgcagagct cattgtttc tctccatata aagctatgac attcacataa taaacatgta  2820
gagagcttta acagacttca atgttaagtc ttctaacagc tgcataactg gtcttgcttg  2880
aacctgtctt tttcataatg ctaccttgcc tttcacacca attctgtgag cccaagcagg  2940
aatgaagatt acctatctct aatggcagga cagaagggag tggtggttaa ggttactgga  3000
ggttattggg ggaataaatg aagacctcat gccacttcta aacactgcca ggacctaaca  3060
taccttgtgt ttttatatcc aatatgggag taaaggttag atattttaac atcaaatatg  3120
aggatgacac tagatggttt taaaagcccc ccaccataac ttctaaactc cacaatgttc  3180
gaatattgtt aggtttcagt gaaatcctac agtagtccct tgcttggaat cactgtagga  3240
ttggctccag caatgggcaa cacaaggttt ggttctatac agtaggtatg ggtcaaagaa  3300
aatgctatga ttgaaaaatt gctgttttcc tcctcaaaaa gctcatacca accaggaaag  3360
agctatcaga aaaccttcag gaaagaatat aatgatagga tataacaaat acccccacag  3420
ctggtccata gaccaaagta taattccaag tagggaattt cacttaacga ggtaaggcat  3480
ttaagggaaa aggaatctag gctaggactc tgctagccag acccagataa attattacag  3540
ggaagcatgt tcttgaggct attctctatg aagaagggca acccaccttg ccatctatat  3600
cctttctgtt ttcgacaggg gtggtcctaa gctggataga tctttactct gaccagtacc  3660
atataggtct gtggttctca aacctggctg cacagtgtgg cactttaagt aatcctgata  3720
cccagtccca tccccaaaga tgctgattta atttgtctaa ggtgcagttt gggcctctgg  3780
attggaacca acccatatac ccatcaatga tagactggat aaagaaaatg tggcacatat  3840
acaccataga atactacaca gccataaaaa aggatgagtt catgtcctat gcagggacat  3900
ggatgaagct ggaaaccatc aacctcagca aactaacata agaccagaaa accaaacact  3960
gcatgttctt actcataagt gggagttgaa caatgagaat acacagacac agggagggga  4020
acatcacaca cgggggcctg ttggagggtg ggggttaggg gagggatagc attaggagaa  4080
atacctaatg tagatgttgg gttgatgggt gcagcaaacc accatggcac gtgtatacct  4140
atgtaacaaa cctgcatgtt ctgcacatgt attccagaac ttaaagaata tatatttata  4200
tatgtataaa tatatatgaa tatataaata taaatatata tataagctcc ccacgtgatt  4260
ctaatgtgtg gccagtcttg caaacctcag gctatttatt ctaaagggtt tgtaacaagc  4320
cttcctctta aaatccaccc caccaccatt cagcgttttg gggtctgttt gtttttattg  4380
ttatcccacc ccacaccgcc ccgaggcgcg cgcgcgcgcg cgcacacaca cacacacaca  4440
cacacacaca catacacaca cgcacactgg tgaatttctc tctacagtca gtctggagta  4500
atcccaaagt ggtgtctttc gtaaataagg agaacccggg tgaagaaaat gactccccacc  4560
cgaacaaggc atgaacaatg ttcactccct actgtgttat tcaacctgtt tccccaggtc  4620
tctgttttca cattagagag tgttctagga gatgacgccc ttcctcctta gttatttccc  4680
caccctcgtg ctggcctttg acagacctcc cagtagaggg cccaagacgc gggtagagca  4740
ccgcgtctca gcgcctgagt ctcagccccc gaactccacc gcacctgcag gtccccttgg  4800
cagcactcaa gcgcggggat gctccgctta gacgaactca cgtgcgggca gcaaggcctg  4860
cgatacttga gcacccctcc ccctctcccg tttacacccc gtttgtgttt acgtagcgag  4920
gagatattta ggtttctaga aggcaggtca tcgcaggccc cacccagcag tggagagagt  4980
gagtcccaga gggtgttgcc agcgagctcc tcctccttcc cctccccact ctccccgagt  5040
ctagggcccc cggggcgtat gacgccggag ccctctgacc gcacctctga ccacaacaaa  5100
cccctactcc acccgtcttg tttgtcccac ccttggtgac gcagagcccc agcccagacc  5160
ccgcccaaag cactcattta actggtattg cggagccacg aggcttctgc ttactgcaac  5220
tcgctccggc cgctgggcgt agctgcgact cggcggagtc ccggcggcgc gtccttgttc  5280
taacccggcg cgccatgacc gtcgcgcggc cgagcgtgcc cgcggcgctg cccctcctcg  5340
gggagctgcc ccggctgctg ctgctggtgc tgttgtgcct gccggccgtg tggggtgagt  5400
aggggcccgg cggccgggga agcccctggg ctgggtggga ggtccaagtc ggtctctgag  5460
acacgcacag gggccggcga cttggcaggt ggggagcttg gcccgcggtc gtggttcccg  5520
ccgtcctgtg cctttaaggc tctcgccgct caccagcatt tggggctcct gctgtgtcgg  5580
cccccagctg acttggcttt aggggtcggc gtggagggtt aaagaggccc cggctgggtt  5640
tgcggagcag ccaagcctgg caaaatcgaa agggagggct caaagagact gtatccttaa  5700
cccccaaaaa gctggtctaa aaggatggga ggccagaccg ctgaccgttc ccccactctcg  5760
acagagtcca gccgtgtgga gcacacgatg ctgcaaactt gcatgtcatc tctttcaggt  5820
gtggcatttc aagggggctt gtgtcttgaa aacagcaact gtgaggacac ttgatagtca  5880
tttccttcag ttctgctttt gtctccctag gtgactgtgg ccttccccca gatgtaccta  5940
atgcccagcc agctttggaa ggccgtacaa gttttcccga ggatactgta ataacgtaca  6000
aatgtgaaga aagctttgtg aaaattcctg gcgagaagga ctcagtgatc tgccttaagg  6060
gcagtcaatg gtcagatatt gaagagttct gcaatcgtaa gttcttcatc tttttagaaa  6120
agttctggga atggaatgta tcttaaattt atttttatat acctttggag tgactagtaa  6180
ttgatagttc tctagcgtta ctaaacccca gggtataccc tgttggcacg tcacactcca  6240
gctaattgaa gacatttacc accctgagta ggtcctgctg cttcattaag agtttttctt  6300
cctaacactg tacctcttga acgaactagt agagaaaata aacaataggt attgtttagg  6360
gagtaaacat ataaaatata tttggcaatt gccttgagac acatagcgta aatgatatgt  6420
tttcttaagt attttataaa gtaggactta ccaaatacaa ctctgtggtg gcatttttaa  6480
aagctctcaa tatttacttc aaaatctgtt atacttgtac atatttatag ggtacatgtg  6540
atattctggc acatgcatac agtgtgtcat gatcaatcag ggtaattgga tagccagtac  6600
```

-continued

```
ctcaaacact tggtgtttgt gtggagaata ttccaaatct tctcttcttg ctactttgaa  6660
aaaatatatg tatatatata aattgggata tatatatagg gagagagata tatataattg  6720
ggatatatat atataaggag atatataatt gggatatata taaggagata tatataggga  6780
gagatatata tatataggga gatatatata tatagggaga gagatatata tagggagaga  6840
gagatgtata aactgggata tagacaggta gataggttga ttgttaaaaa tgaataagag  6900
gcccagtgaa gagttgtttg ggggctaaca cagtaaccgt gtttgatact gatacctagt  6960
agaattaaaa gaaatgaaga tttcttgttt taggtgaata tacatacagt catccacacc  7020
ttatgtgccc tttgatttca taaaatatat attggcatta tcttggagga aaaaaatctg  7080
ttacttacat agccctgtat tagctttgag atatatgagt agagataaag ataaagagac  7140
ccgataacct gactttgaac aacttaaatc aatagaagct actgtaaata cagaaattgg  7200
cacaaatacc tttagaagcc atgcgtgaaa taggctttaa ctttttattt ttatccacaa  7260
tagaggcagt aggatgaagt acatagtctt tgcacatgta tcatgtttta actcttcccc  7320
atgttattac tttatccaat cctccaaaca accttatgag gtaagttggg gctcttacac  7380
tctttttatg gcggaggaga cagaccccag tagtttaata acttcctcaa gagcagcagc  7440
ttttacgcca aaaccaaggt gtaaacttgg gtcttctgac tacaaatcca atgatgaccc  7500
ttccacttga ccatgcctct ctagattcac atttgtgggc aatctgttta cagatgtaaa  7560
tactttatgt atacaatttg tgggcaatct gtttacaggt gtaaatactt tatgtataca  7620
attgactcat ccttgccccc agggctcatg ggaattaaat gagtttgtac gtaaataaat  7680
attagctgct attattgttg tgcaggacat tagtccaggg gtctggaaat accctattcc  7740
tgtactgtat ggtgctgtgt agttctttag ggcagggtaa ggaaaccaac atttattgaa  7800
tgccagaact gggccaggca acttaaattt tttttttttt ttaagtgggg atagtgatat  7860
gtgtgtacca actctacttc ctaagcctct agtaactagg aaacaaagta tacatgtgaa  7920
tacatttgct acattgcaag tgccatggtg atattaatat agttaagtac taaatatgcg  7980
caaagcagta aagaaagggg gttattaggg tccagataat taaatataga ttataaaaca  8040
aaaattgata ctacattttt tgttgctgct tttgttaata cttttaggta gctgcgaggt  8100
gccaacaagg ctaaattctg catccctcaa acagccttat atcactcaga attattttcc  8160
agtcggtact gttgtggaat atgagtgccg tccaggttac agaagagaac cttctctatc  8220
accaaaacta acttgccttc agaatttaaa atggtccaca gcagtcgaat tttgtaaaag  8280
tgagtaaaat tttttaaagt attttcaacc atctggtgtt tgggggaaat agtatccctt  8340
ccttcattca tgctagaact ctatgtgtat atattattat ataggatgtt tcttgatagg  8400
accatgagtg tcaatttatt ttgaattaga ctaaatattt atgtggtagg aatacttatt  8460
cattcaaaaa tttcacattt aattagtttg aggttaccta aaataaaaca agtatatatt  8520
ctaaattcgt tgctttttca aaacttatta taaagagaaa ttagaattaa agaagtctaa  8580
gggtcaggca tggtggctca tacctgtaat cccagcactt tgggagacag aggcaggtgg  8640
accacttgag gtcaggagat tgagagtagc ctggccaaca tgatgaaacc ctgactctac  8700
taaaaataca aaaactagct gggtgtggtg gcgcatgcct gtaatcccag cttcttggaa  8760
ggctgaggca ggagaatccc ttgaacctgg gaggcagagg ttgcagtgag ctgagattat  8820
gtcaccgcgc tccagcctgg gcaacagagc aaaactccat ctcaaaaaaa aaaaaaaaaa  8880
agtctaagga taagaaatat caatggttca gatgatgaat ttacatatat gtgcttgata  8940
atttttttcaa aattttttacc tgagctttat tgaggtataa tcgacaaata ttatcttagg  9000
tgtacaacat gatgttttga tatatgtgca cattgtgaaa tgattaacac agtcaagcta  9060
attaacatat ctaccacctc acatagttac cttctttgtg tgtatgcctg ataatttaat  9120
tttaaaaaat caatttgtat tctattctag agaaatcatg ccctaatccg ggagaaatac  9180
gaaatggtca gattgatgta ccaggtggca tattatttgg tgcaaccatc tccttctcat  9240
gtaacacagg gtaagtttgg gcatactaaa accctgtatt taggaaatga gaaaacaaat  9300
taggacttaa ggtgagattg ttagtttcat gactggtatt cacagctagt agcaattaaa  9360
acaatccctc tcctcaaaga cccttcatca tgagctcatc acagttaaat ttagtaaaat  9420
gggggcaaga aaggaagatt tcttaaacca ccagaattct ctaaattctg atttcagtaa  9480
atatgtgatt caatataaaa ttttaaatgt gattaataaa aaaatttgag atgatgatac  9540
ttgcagaaat cttcaaatgt taaatactaa accaatcttt agttgaccta aataatgaat  9600
ttgcatgagt ttttctatat gcaaacaagc tgttacaaaa cagcatgagt taaagacatt  9660
cctagtgtga aagtattcta agttctttga taagttctct gtatagggag aaggaactca  9720
ttcattgagt accatcaatg tctcagacac tgttgaaaac tttacattta ttttctcatt  9780
tcatatctgt aaattaaata attctatttt actctgtgtg tgtccctatt ctttataaag  9840
taaaaatatc agtatcactt gtctcctata cgaaacacag atattggtta ggtcatgaac  9900
acaaaatctg ggaagtactt tgaacccttt aaatataagt acattctatt attctgtgaa  9960
gcccatattt agaactcaga ggtataaaat gttcaatcat ctatgtcatt taaaaatgtt  10020
taaaacactt ttatgctttc taacatattc cccatgcaaa taaaaaatgt acatgtctta  10080
tctgttttta ctcttggat gtcacgtttt taaacttaat ttttctttc ctttaaacta  10140
ctgtgtggac ttttatcaac tactgtttta tattcaccta attgtgtagt aaatatttta  10200
agataataac ctggagaatt tgaggaaagt caaatatgtg tgaatgtaac aaactctttt  10260
ttcttcccct gttgctttag gtacaaatta tttggctcga cttctagttt ttgtcttatt  10320
tcaggcagct ctgtccagtg gagtgacccg ttgccagagt gcagaggtaa gagttaaaaa  10380
atctaagcac tcagattgtg aggctgagta ctcaatgata aattaatttc tgccccttaa  10440
gaatattagc acagtgtgta tttgtagcaa acccaccttt caatatatga gtgctttgct  10500
aattttaaga ccttttctag tgatgttcct tcatttagca gctgtgaaga taaaccagca  10560
agttttctga gtcccaattc ccaaattgta gaatgaggat taaaaacaaa cttaggtttg  10620
tattgcactt ggtcatttat tgtctaacca ttacttctaa agtcaagtat gataggtgaa  10680
agatttccgc cccacaattt tgtgtaagaa aatagtgtca atcagagggt ctgtaagact  10740
tgaccccata tcctaaaaca agtggcaatg gaaggcattt aaccaggtct cttatttcaa  10800
acccagcatt tttctaaaat ccagtgttgc ctacatgctg cttcttagga ttaaaataat  10860
taaccgagat aattatctag aggggtttta aggtgtgata tattcttatc attagagaga  10920
taagcttata ccgtcaagaa gaaatactgt gtctgtattt gagaatcttc tcaaagaaag  10980
atatggtgca gaaataatat tataaatgga tatatatcca gtcaaattta tgtcaattag  11040
agacacatgt ctcttggaaa ttgagaggaa taaaatacat gcaacatttt aaaatgtagg  11100
cttgctttct ttccatcctt ctctctctcc acacacaatg tgccctcctg caaatgactt  11160
ctgaaggccc tattgtcaaa attattgata agttaaagtt tttgtatgtt actaggggaa  11220
gaaaactaga gtagatttag tgtaatttat caagcattta tcgattgaca ctctggtagg  11280
caacgtgtac ggtcaactga cacgaagaca aataaaatga agccgtgcca ttaaggagcc  11340
```

-continued

```
tgtccctgcc acacccacca tgtgcccttc tttttgagat gtcatactac tacctttttt  11400
ttctcattgt agttgttttt aaatttttca tcattgctac ccagtagcac ctttcccatt  11460
ttcgttgtcc agtaagagac attgtaaatg atagtaaatt aaagatagaa aacaaggaaa  11520
agctgggcca tatcttttgt ttgacccagg caacatgtca caaagttcag acaaacagtc  11580
tcccatctga agccagtatt ttcacaagca cctgctgtgt catgaatttg acagaaatgc  11640
aaacccactt tatcttcctg cttgcacatc taggccacag ccttgcttcc ctatctggtg  11700
tcttgaactc catgctgaat attctgatgt tcatgttttc ctccttgact cttctatcct  11760
ctctgtgact cagcaaccac tgacatctgc atcctgtagg aaagagcccc tgttcttaag  11820
caatcccagt gccttcaaat atccctataa ggccttactt ctttcaggat cattttgatt  11880
ttccacataa cttgttttga ccataccaaa aagattgaat ggaaagtgaa ttcttaaaca  11940
atgtactgct tcacctcaag tatgtagccc tagactataa acacatgagg ttgcttcagt  12000
gtccatgcgt gaatatggat acgaagaagg aaagaacagt ggacacattc actaattgtc  12060
tatagttata cagaaaacag aggtgctgct agtttacctc tgaatagagc ctcactgtca  12120
gaggacctgt ttgcttatct ctctgccaat gttttctttt tcaaaatttt agttgactga  12180
tggtatctgc taacctagaa tcaatccctg ctatatgact atcatgccag acccttctct  12240
ttatcttaac tccccacatc tcatccctaa atcattgtgc tttacctcct caatctgttt  12300
ttcaaacttg tgttttgctc tccatctgta tatttctagc atagtttatt attcctcctg  12360
tggactattg caattagggc caccccctaac attttcaggg cccaggcaag aatataaatg  12420
gaggtcgctg gcctaagacc caccttgtat caaatagccc ttcctcttcc cacactgtat  12480
gggttctctg gtgcacataa gcggacaact cagcctacat acccaagaca tgtccaccac  12540
atccaccata acttgtatcc accctccatt gtctgttggg ttagaggtga gtatatcagc  12600
aggatagacc accctcaaga acatggacca gtgggaggga ccctctcagg ccctggaagg  12660
ggtgttggca cagggaattc tgggtgctag ttcctggagc atgttctgga atggaggaga  12720
agtcgtagga caggctgtca ttgagtatat gctatcagcc tacaaacatc ccaccaacag  12780
gggagaaatg catccagagg agggccagag cacagccttt taaaatgtgg ggtttgaggc  12840
agcaatctta gttgcctgag ttcaagagtg acactgatag caatggcctc ctgcctccat  12900
tctttcactc tattaatgtt tcatccatat tttacccaga gcgatctgaa acacagatgt  12960
gacttagaca tctatttcct ccttagagct tattcatatc tcctatcact taaaaagccc  13020
aaattcctta gtatagtgta caaggcagcc atggtctacc tactgcttga cactcaggtc  13080
ttgccttcat gttttatgcc ttatacatgc aaactgctgt ggtttccatg tacctctttt  13140
ttttcttttt tttaaattga gacagggtct cactctgttg cccaggctga agtgcagtgg  13200
tgcgatcaca gctcactgca gcctcaacct ccttggccca agtgatcctc ccacctcagc  13260
ctcccttgta gctgggacta taggtgcaca ccaccatgcc cagctaattt atgtattttt  13320
tgcatagaca gggcttcctc atgttgtcca ggctggtctc gaactcctgg gctcaagcag  13380
tctgcccgcc tcagcctccc aaagttctgg gattacaggt gtgaaccacc atgccccgct  13440
gccccttctt tacttagcta tattttcctt actaagagtt agttccctag cccatcagaa  13500
agattcccag gctggctact tcgggatgac ccttgcattt tttattgaaa tcatttctga  13560
atctttttc ccactagctt ttaagacata ggaactatat cttgttcagc tttgcgcttc  13620
caattataaa aaaatgcctg gcgtgtgtta ggcactcaga aaatgtttga actgaaccaa  13680
tggtgtgtgt gtctctgcac actctaagtt agtgtaaatc agaacagctt gttgttgctg  13740
cttgttttga tccaagacca aagagtgatt gataaatgtg ctaagtattt tctgtgttct  13800
taagtatgtt tggtgtaaca taatttggca tacacacata ttaaattgcc ttcattctta  13860
aaaaaaaaaa aaaggacaac aacatcatgc ctttagatta tgtggaacca ttgaattttt  13920
tctcagggta actgccaggg agtggtccct ttttacagta taactaaaaa aacttctgct  13980
tgtatttatt ttgtaagttc agctgctcag taagattgtt ttgagtgaag tctctgtgag  14040
tccatatgtg ctaaaaattt ttactctaga agtcaaaatg taatcctgac atttaagatc  14100
tctgctgtat ccaaaatgat ctatacttaa ctcttaaaca tgctgcttga attttcaact  14160
ccttgcattt gctagcgttt ccctcttaga gtgaagagca acgctttctc cgctgttctc  14220
tctcaaaagc atggtacata ttaggtttaa actcaagttc tatttccctg cccaagtctt  14280
ctctgactac actgctttca tctctaaaat cctgcagcat tcacttttcc tagcaccgtt  14340
ttgatatgca cacatcttac tataattttt cttttacata catgttctga atcttattat  14400
ttctatgaat tggtctcaag gttagcattt gtcttctaca ccatttgcat tcaaagctcc  14460
cacatactac caattactta ataggcattt ataagcatct cttgttggta atgctgaatt  14520
tagaaaaatg atattttgat ttctttaaaa tataatcttt aacatgtttt gatcttattt  14580
gtaaaaatac tttactagtt ttatttattt aaaagatgtt ggaattgttt tttaagaaat  14640
ttattgtcca gcaccaccac aaattgacaa tggaataatt caaggggaac gtgaccatta  14700
tggatataga cagtctgtaa cgtatgcatg taataaagga ttcaccatga ttggagagca  14760
ctctatttat tgtactgtga ataatgatga aggagagtgg agtggcccac cacctgaatg  14820
cagaggtaat cactttggat agttatattt ttgctttatt cttaccctca ggtctatatg  14880
tgggttgcag acattcaatg aacccccctaa gaaaaaaatg taaaatgttt acatatacat  14940
atttgtattt ttctgtggga cacaattttt ctacagcttc tcagaagggt ctatggcttg  15000
tatacacaca cacacacaca tactcacaca tattatgatg tgtatatata aaataggcct  15060
catatttttg gcaaatttgc ttacatttgc tgttttatac catgttgctt tcagtaagtt  15120
aatataggta ctttgtttat acaaagagat ataaagtggt ttattggagg gagaatctta  15180
gattgaaggc tctagatagt gatcatacct gttgcaacaa ctgggaaact cttgccatct  15240
gttgacttca ctgaattaac attcaattct tttctgcctc cagaatttct attattatcc  15300
attctccttc atccttctag acgtttttct ttcaatgtct ttttataccc agaaggtact  15360
ctcagaatcc ttcgaactgc tttttaaata tattttaaaa gaaatattta gaagatcagt  15420
gaagctggac taaacattgc ctagtatcaa taggtggcgt ttaagtagtg gtgaatacca  15480
acatgactca agcatttgag tatttacttt tataattata attgaaattt tattagtatg  15540
aattttaaaa attccttatt aaaatagatt tttattataa gtgttataca tagacataat  15600
gacataatat taaagccagg gagatgagta caaaatggga agtgaaagtc tcttctctat  15660
cactagtcct actcggagag gtaacaattt tttacaaatt cttttgtttt attctagaat  15720
ataaataaac atacaaatat tttttattta ttatatcaat ggtgtgggta ttcatttatc  15780
taaccagtcc tctattgatg acaatttagg ttttttgttc tagtttgatt ttttttatga  15840
actattatta caaatgatgc tataatattc ttgtacatct gtcactgcac atatatgcaa  15900
gtacatttgt acaataaatt ccttgtagta taattattta taacaaaggt atgtgaatta  15960
catttttcat gcccattagt agcactgctt tttaaaagac tgtaccaatt tagtctccca  16020
ctgatacaac atcattgtgg tgtttgcacc tttaatgata atgattgtta gggagatttg  16080
```

-continued

```
acaatgtaaa tggtaaaaat ttgtattatt tgaattcatt taattatgaa gtttagtgtg  16140
tgtgcttttt taatttggcc atttgatcca gttcatattt atttttccaa gttttattaa  16200
atgatcagtt atttagagct taaaaaacca tatggaagta cccaagtagg tcatggcagg  16260
ctgatgcttc cattaaaacg actataaaat ctcaatagat taccaaaaaa ttatattttt  16320
taaggcataa gatacagctg tggaagcaac aaggtctgaa tgaactaaaa ttcctggggg  16380
caggtggtga aggcaaccca tcctgatgta aggcagtttt ccctagggac ctttgctgat  16440
tctgaacctg gactaaggat tcaccttgac ccagacaaaa gaccacttct aggaaagaga  16500
aaccagcaaa gctttaatgg ttatggaggg atagggtaat acactggaaa ttgaggccct  16560
caaatgcaga accaattttt cctaaaggcc atttgcaaat tttggggctg catgtgaggc  16620
tgggaaggtt gacccagagc ttctaaagta caaaatgaaa tctctcagaa cctgatggta  16680
tttggatagc atatacccac cagaggaaca ggcttttatc tagcatacca caggtctccc  16740
ctttagcaca tctgtgctca ttttgaaact gtatagggaa ggacattagg tggctgggag  16800
aactctgaag gacagacctg gatctcctgc caccttccaa aggtgaaaca acaaaaatcc  16860
gccaggcttt cagtcagaag cccggaaggg ccactcccaa ggaacagagg caagagcaga  16920
agtagatgga gtcttactga aactgaaacc cagctcaatt cctaataggt tgaagatatg  16980
attacctcaa tgcagtctgc ttatcagaaa ggcatatcat atcatccgga tggtttatat  17040
acaatgtttg gcatacaaca aaagactgtt agatatggaa ggaagcaaga aaatgtgacc  17100
aaatcaagag aaaacaaaac caaataaaga atatccagat aattgagtta gcaaatgaga  17160
accttaaaat aactgattaa caagtttaag atgataaaag aaaagagaac ttcagttgga  17220
atctgcaaaa atggtgtaaa atgaatattc tacaactgga aaatatctga aattaagaac  17280
acaatagata ggtttagcta ttcaggcaga gcaggaaaca gtattaggaa ctgaaagatc  17340
ggttaaaaat acccaaactg atgcacaaag agaaaaagga atgtgaaata tagataaaag  17400
tttgagacat ttgagacatg ttaaactgtg ctaacacatt aggaaaaaga gaaagtgaga  17460
caaaaaggaa gaggggaagg aggaggagga gaagagaaat aggagcagaa gaaatattta  17520
aaatgatact tactcagaat tttccaaaac tgataaagta cattagccaa cagattcaag  17580
aagctctctg actctaagct gaataaaaat aaaaccactt tagcaaaaaa tctaactcta  17640
agctgaacaa aaataaaacc actcgtagca aaaacaaaca acaaaaactt caaagaagca  17700
acagtataac tgattactgc tcagcaaaaa atgatgcaaa ccaaaagaca ataagaagaa  17760
atctttaaaa tactgtaaga aaattactgt tcacctagaa ttttataccc agttaatata  17820
tccttcaaaa ctgaatgcaa aatagagatg tattcagaca aaaaccaaga aaactttgca  17880
ctagcagacc aaacatgcac agaatgagaa actaaaggaa attcttcaag tagaatgaaa  17940
ataatgccag gtaaaacatg aaaatacaaa aggaaatgaa cagtgacaag gataaatgaa  18000
tactgagttt acaaacagtg aatgtaatgt cctgtggggt ctgaattata catagaatac  18060
aaatgcacaa taacaatgcg aaaggcagaa agaggtaaat tcatttaaag gttacacagt  18120
tctagcagta ctgaaaaggt ggtaaaagtg atagtttgca taattgactt atagtctaat  18180
aaatattgtg atctctaggg ttgctacaaa tgaatgacag aagaatacat aaatcacaag  18240
ctaataaaag aataataatg gatatttaat ccaaaagaga acgagagaga gagaagcaga  18300
aaggaacaca gaatagatgg gagaaataga aaactaataa ggttgttgat ataaacccaa  18360
gtatgtcagt aattatgtta agtgcaattt gaccaagatt gtcagactta aaaagatttt  18420
aaaaagaacc tagttcttta ctatttacaa gagacacagt ttaattacaa gaacacagaa  18480
tagttgaaag taaaggatgg aaaaatatac catgcaaata ttaacccttc aaaataagct  18540
gacacagtta cattaatatc aatgtatatt ttaagatgaa acagttcata atgataagga  18600
ggccaactca acagtaatat atcataatct ggaatctata tgtacttgat aaaatagctt  18660
caatctatat gtagcaaaaa tggacagaaa aaatagacaa atacacactc atagttagaa  18720
aattccacac ctatctcaat agctaatagg acaagcaacc aaaaatcagt gagactaaag  18780
atctgagcaa caattaaaca tatatacata tgagaccatt gaatctatta ggaccgatga  18840
caggtatgtt ttttcaagtg cgcatgggct atttaccaaa attgaccctt tgctgggctc  18900
taagctacaa tacattgcaa aagattgaag ttattcagag catactttct agccacagtg  18960
gaattaaact agatgtcagt aacgaaaaga taactaaaaa attaacttct aggaaattta  19020
aactctaagg tagtatatac attctctgga tcaaaactga gaactaactt gatagaacaa  19080
agaataattt agaatagttt ttatatagga gggtcttaga atgaaaagtt cataaaaaaa  19140
ctttacttat cttaataatg attatcattg tttgagtgcc tgctaaatgc tgttacctgc  19200
taggcgtttt actcaattta tcccttatag cagcctgtga gataggttag gaggcagaaa  19260
aaaatgaccg ataccatctg agttcctagg gcatcccgtg tgtgatgggg ctggcaacag  19320
tcatcctgga tgatgtaatc tcttgcttca gggacagaca ctgtgaaata gcttactcaa  19380
ttatttccct taatccttcc tcaataataa ttactcaatc tgttctgctt ttatcctcat  19440
tttacagatg aggaaactat agcttagaag ggttagggac ttgctagagc tcactaatac  19500
gtggtgaaat caggcttcgg cactacccaa tactgcctca acaggggact ttgtataagt  19560
gacccaatgg cagttgggct ctgaagactg aaaaagttgc tctgctgtta gatttatgct  19620
tttcagaata tgttcttaat gaaagtttca cctgacttgt tatctagtct gaaatctaaa  19680
gaggaactgg tgtatggaaa gttggtaacc agcacaagag aattaaaagg agttattttt  19740
actcagactc gagtatcact ttaaacaaga cgtgaaacaa aacaaattct caggctcatt  19800
aaggttaagt gatagaaaag gctgtgactg tctctgttgg cttagttgtt ctagaacaac  19860
atcctgttgt tctttagtat tagcacaaaa gataatttgg gagacaaaat agagatgtgc  19920
cacagaataa gatcactagt gactctttga tttgtttatt tcacaagaag cagcttaagc  19980
acctcagtat actttggtat aagtcttctt tagttaccca taggtataat ttatatcaaa  20040
gcaaacgcaa cttagaactt cagctccttg agaaatactc aataagagtt ggtttcctga  20100
aagtcatacc taggtgtttg tggggagaga gaaaggatag ccacagagca agcaatggct  20160
aagaatgtta atgtggccag caatatttag ctaacttgtt tctcaacctt ttctttcaca  20220
ggaaaatctc taacttccaa ggtcccacca acagttcaga aacctaccac agtaaatgtt  20280
ccaactacag aagtctcacc aacttctcag aaaaccacca caaaaaccac cacaccaaat  20340
gctcaaggta cagagactcc atcagttctt caaaaacaca ccacagaaaa tgtttcagct  20400
acaagaaccc caccaactcc tcagaaaccc accacagtaa atgtcccagc tacaatagtc  20460
acaccaacac cttagaaacc caccacaata aatgttccag ctacaggagt ctcatcaaca  20520
cctcaaagac acaccatagt aaatgtttca gctacaggaa ccctaccaac tcttcagaaa  20580
cccaccagag caaatgattc agccaccaaa tccccagcag cagctcagac atctttcata  20640
tcaaaaaccc tatctacaaa gaccccttct gcagctcaga atcccatgat gacaaatgct  20700
tctgctacac aggccacact aacagcccaa aaattcacca cagcaaaagt tgcatttacg  20760
cagagtcctt cagcagcacg taagtccact aatgtacatt ccccagtgac taatggtctc  20820
```

-continued

```
aagagtacac aaagattccc ttctgctcat attacagcaa cacggagtac acctgtttcc  20880
aggacaacca agcattttca tgaaacaacc ccaaataaag gaagtggaac cacttcaggt  20940
cagttgacac tgttcaggtt tactgagtat ggatctaatg tgctatggtg gaaatatgaa  21000
cttgaccaag attgcaggat taaatggtct ctaatttatt gtagccaggg tttttcatac  21060
taatactttt tactttattt ggaagcggac ttggattgta ctagggcaaa tctttaaaaa  21120
aagaaacatt tacaataata gagaaaaaga ctgtggcccc attaaaaaaa tgctaaatta  21180
agattggtaa aaaaaaaaaa attctgtttc ctgtagtagt tttagggagt caacgaatta  21240
ttcaagaccc cttcaaagaa ccaaatatgt actgtcttta aggctgagtc ctgggtctgg  21300
ttcattgata gagatccatc cctcaaagta tgctaaggaa tcttcccgga ttccctagag  21360
ttgcagatct gctaaagcat ctcaatagtg tcgtctaagt aattgaaaat acagagatcc  21420
tttcaaatag ttcgtattat tacaaggctc tataaacgat aggttctcag tggcaccaag  21480
taattgtgtt ttatctatag ttttacccat tatgaccgta ttttcaaaat gattttatat  21540
atttcataat tgttaccttg aagcctattt tgccagcacc tggatatttt taagaattta  21600
aacattatgg atgttatcgt taaagttccc ttaaaacatt tccccagccc atttttctcc  21660
ctctaaggca attactgccc tgaaactgat gtgcttactt cctgtctgtt ttcattctta  21720
tactccatgt ttccataagt agtacataat aatgtttcat atttttaaaa taatttacag  21780
aaactgtgta tgtttcatta cctcttagca ctcagcattg gttttgtggc ttacattgat  21840
taatttagat ttactatact aattttaatt ctttatgtgg ttttttttact tctttacaat  21900
tttatgactt ctcttggtct aaaatttcta ggttgaacac gtccagtttt taatagggca  21960
aggcaaagag aaataagcat cacttataaa tttgttatag aactaacttt attgacatat  22020
ttccttctgt aaaaagtata agataattta agacatttaa actgaacctg atgagtcaat  22080
tataatatat caatatttgg gatcaaattt tactcttagg tacaattaat ttactctttc  22140
agggcacaat ataaaaaaat tgtagccacc acttactgag tatatactat agtgatatgt  22200
tccgttcacc ttctgtttga tgccactcgt ctgtaccaca accttgcaaa gtatcttcag  22260
attgatttta tagatgagga attagaggct tagagattaa ttcatccagt tcatatccag  22320
tgcacagttt aatcctgcac ttttctgct gagtaatatt gcttgttcta aatggcactc  22380
ttgagtcaat gtgttcacct cgcttaggag agcagcttat ttattgttat aaatatgctt  22440
atctgaaagt aaatttattt ttgcaatgcc ccatccgtag tcattgaaag atataaataa  22500
taaggtgata tggcattttt gagttttgat atagtctgct aaaagggact tagtcgtctt  22560
atagtttctt gttagtagga ttggatcagc aattatttac tgtttaagtt ttcaaacatg  22620
tttcttgccc tcaagtccta taaccaaatt taaatggcat ttgttttggt aatcaataac  22680
tctttatcat aatttatatt tacagtgttg attctgttga acaggtatag acagtaatgt  22740
ttacattcta cttgattaag ttaatgtgta attgttttta taaatttata attatttcat  22800
ttgtggaaat ttgagttgct ttcgagtttt ctagtgtagt ttattgatag tatatgaaat  22860
tgctagcaaa tcaatgactt taacaaattt ttgttgttaa tcctttttttt ccccttcgtc  22920
tgtaggtact acccgtcttc tatctggtaa gtttggctct caggccatta aaagaaattg  22980
ttttcactgt gggatataca atccatattc ctgggagata atattgtctt cttgttttta  23040
aaaaaatgta tcctgcaatt tatttttaaa ctttttagta tggaaaactt taaacgtcac  23100
tcaaataggg aaaatagtac agtgaatcct catatactcg ctcggattca gcaattttca  23160
actcatggat acccacttca cccacactcc ctggattatt tggaagataa tcccagacat  23220
cgtatcattt ccttcataaa catttcacta agtaaccttt ataaaaacat aaccatgtag  23280
catacctaaa aaaatccagt aattccttaa tatcagcaaa tatttagtca atatccaaac  23340
ttccctgatt atcttataat tttttaattg atacataatg ttttatatat ttatgaggta  23400
catgtgatat tttgttacat gcatggactg tgtgattctc aagttggtat ttggggtatt  23460
catcaccttg agtattattt ttgtgtgttg gaaacatttt aggtcctttc ttctagtgac  23520
tatgaaaaat atatcacaca ttattgctaa ctatactcac cctactctgc tattgaatat  23580
tagaatgtaa tccttctatc taattgtatg tttataccca tcggccaaag tctcttcatc  23640
ctccctccta ctcacacact tttctcagcc tctggtatct aacattcttc tctctacctc  23700
catgagaact tttttaggtc tcacatgtga gtaagagcat gtgatatttg tcttttttgc  23760
ttggcttatt tcatttaata taatggcctc tagttccatt catgttgctg caaatgacat  23820
aactttattc tttttatggc tgaatgtatt tcattctata tatgctagat ttgttttctt  23880
tcttttcttt tttttatttt tattttttt ttgagacagg ttctcgtcct gtcacccagg  23940
ctggtatgcg gtggtgtgat cgtagctcac tgcagtctcg aactcctggg ttcaagcgat  24000
ccttccactt cagcctccca agtagctggt actacaggtg tgtgccacga cacccggcta  24060
agtttttgaa atttattttt tgtagagaca ggattttcct atgttgccca ggctggtttc  24120
aaactcctgg ccgtaagcga tttttccggc ctcccaaaac gttgcgatta taagtgtgag  24180
ccactgcacc tggccccaca ttttctttat ccatttgtac attgatggac acttaagatg  24240
attccatatc tttgctattg tgaatagtgc ttcaataaat atgtgaatgc acatatcttt  24300
ttgatatatt ggttttattt tcctttggat aaatacccag tagtgggatt gctggatcct  24360
aagatagtta tatttttttta tgttttcagg aacctccata ttgttttcca cagtggttgt  24420
actaatttac attctcacca acagtatata agatttccct tttcttcacg tcctcaccag  24480
cgtctgttat tttttgtcta aaaatggcca ttctaactga ggttaagaac tgatagctca  24540
ttgtggagct tgatttgcat ttccatgatg attagtgatg agcagttttt catatacctg  24600
ctgagaaatg tctgttcatg tcttttgccc acttttagt gtgattattt gtttttcgct  24660
agtaagttga gttcgttgta tattctggat attagtacct ttacagatga atagtttata  24720
gatattttct tccatttagc aggttgtctc ttcactctgt tgattgtttc ctttgctgta  24780
cacaagcttt ttagtttaat atagtcctat ttatctattt ttgtttttat tgtctatgct  24840
tttgaggttt tagccattaa acctttgcct agactaatgt cctgtagcat cttcctgatg  24900
ttttcttcta gtatttttat agttgtggat cttatgttta agtttttaat catctcgatt  24960
tgatttttgt acatggtgag gggcagaggt ccagtttcat tcttctgtat tttcccagca  25020
ctatttattg aagaaggtat ccattttcca atgtatgttc ttggcacctt tgtaaaaaaa  25080
tcagttagct ataaatatgt ggatttattt ctgggttctc tattctgttc cattattctg  25140
tgtgcctgtt tttataccaa taccatgctg tttttggtta ctataacctt atattttgaa  25200
gtcaggtagc gtgatgctgc cagctttgtt tttgctcggg ttgtgttagc tctttggact  25260
cttttggttc cacaatcatt ttaggacttt ttttttcta tttctgtgaa aaatggcatt  25320
gatatcttga taggggttgt actgaatctt tagattgctt tggcagtgta gtcattttaa  25380
caataatagc tcttccagtc cgtgagcatg ggatgtcttt ccctttgtgc cctcttcgat  25440
ttcttttatc tatgttttgt agttttcctt gtaggggtct ttcacctcct tagttaaatc  25500
tgttcctagg tattttattt atttttttag ttattgtcaa tggaattgcc ttcttgattt  25560
```

-continued

```
ctttctcagt ttgttcatta ttgtatagaa atgttattga tttttgtatg ttgatcttgt  25620
ttcctgcaac tgtactgaat ttatcagatc taagagtttt tggtgaagtc tttaaggatt  25680
tttttttaca tataaaatcg tatcattaaa aaagagggac aatttgactt cctctattcc  25740
agtttggatg ccttttattt ctttcttttg cctggctgca agttaataaa tgaaaacttg  25800
gttctctatg agccaaatga aacttggttc ttcaatgaaa tggaaactag ggcttacagc  25860
attatgttga atagaagtgg tgaaagtaga catccttctc ttgatccagt tcttagaaga  25920
aaggctttca gcttttcctc attcaacaga atattagctg tgggtttgtc atgtatgacc  25980
tttatgatgt taatatgctt cttctatgcc tagtttgttg agagttttat tgatttctat  26040
gtgttgaatc atccttgcat ccctggtcga aatcccactt ggtcttggca tactaatttt  26100
ttgatgtggt gttggatttg gtttgctaat actttgctga gaatttttgt gtctatattc  26160
atcaagagta ttggcctgtg attttgttgt tcttgttgtg ttcttgtctg gttttggtat  26220
cagggtaatg ctggccttat agaatgagtt agggaaagtt tcctcctctt caatttttg   26280
gaattgtttc aggagaattg gtattagttc tcttttgtat gtttggtagc atttggcttt  26340
gaatccatcc agtcctgggc ttttctttgt caggagactt tttattacaa ttcagtctta  26400
ctactcatta ttggtctgtt cagattttct gtttcttcct gactcagtct tgatagggag  26460
catgtctcca agaatttatt catttcctct aggttttcca gtttgtcaat gtataggtgt  26520
ttataatagt ctctgatatt ttgtatttct gtggtatcag ttgtaatgtc tctttttca   26580
tttctgattt tatttggggc ttctctcttt ttttcttggt tagtctagca agtactttat  26640
cagtttggtt tatcttttca aaaaaacaag ttttcacttt attgtttttt agtctctatt  26700
ttgtttagct ctgctctgat ttttcttact tctttccttc tgctaatttt ggggttggtt  26760
tgttcttcct tctctagttc cttaagatgc attgttagat tgtttatttg aaatctttct  26820
actttttga tgtaatcatt tattgctgta aacttccctg ttagcactgc ttttgctatg   26880
tctgataagt tttgctacac tgttgccatt tctatttttt caagaaattt tttgtctaat  26940
cctgaatttc tcccttgacc taatggtcat tcagaagcat gttgtttaat tttcatttat  27000
ttgtacggtt tccaaagttc ctgttgttat taatttctag tttaattcca ttatggtttg  27060
agaagatact tgatacaatt ttgacttttt caaatttatt gagacttgtt tggtatccta  27120
acatatgttc tattctggag attgtttcat gtgccattga gaaaattctg tagctattgg  27180
gtgaactctt ctgttagtgt ctgttaggtc catttggtct aatgtgcaat ttaaatccaa  27240
tgtttctttg tgaatttttt gtccagatga gctaatgctg acagtgggat gttgaagttc  27300
ttaacaatta ttgtattgga gtctatccct ttagattgga caatatttgc tttatatgtt  27360
tgggtactcc aggattgggt gcatacatac ttagaattgt tatatcctct tgctgaattg  27420
atctctttgt caattatata atgacctcct ttgtctcttt ttactgtttt ttacctaaag  27480
tctgtttcat ctgatataag tacagctact cctgtttgtt tttggtttgt gttagcatgg  27540
agtatctttt tccatctctt tactttcagt cacaatgtgt tttcacagat gagatgaatt  27600
tcttgaaaga aacgtatagt tgggttgtgt ttttgcatcc attcagccag tatacatctt  27660
ttaagaggaa agtttaatct gtttacattc agggttattg atatgtgagg aattattcct  27720
gtcatcttat taattgattt ctggttgttt tgttcctttt gttctctctt attattgtga  27780
tgtagagttt ttctttcata acattttagt cttttctctt ctttgtgtgt ttgctctacc  27840
agtggttttt aaaatttctg tgtgttttca tgattgtaga tatcattctt tctcttctgg  27900
gtatagcact cccttaagca tttcttgtaa gccatctcat ggtgatgaat tccatcatgg  27960
tgattaattc catcagcttt cttttgtctg ggaaagacat tgtttctcct tcatttatga  28020
aggataactt tcctaatcct tggttggtag tctttttctt tcagcgcttt gagtatatca  28080
tcccgttctc tcctggcctg taaggtttct gctgagaaat ccattgttag tctgatgggt  28140
ttcctttata agtgactaga tgcttttccc ttgctgtttt tagaactctc tctgtctttg  28200
acttttgaca gtttgagtat agtttgtcat ggagaaaacc tttttttttt tttggttttg  28260
agacagagtc tcattctgtc actcagcctg gagtacagtg gcgcaatctc agctcactgc  28320
agcctctgcc tcccaagttc aagcgattct cccacctcag cctcctgagt agtagctggg  28380
attacaggtg tgtgttacca cacccatcta atttttgtat ttttaataga gacagggttt  28440
caccatgttg gccagtctgg tctcgaactc ctgacctcag gtgatccacc tgcctcggcc  28500
tcccaaagtg ctgggattac aggcatgagc caccgcaccg ggccagagaa gacctttta   28560
aattgtatct acttggtgat ctctgagcct cctgtgtcag gatgtctaca tttcttgtta  28620
gacttgagaa attttcctct gttgttttag taatagattt tctaatcctt tcactttctc  28680
ttcaccttct gagactccta aaatttgaat agttggccac tttagggtgt cccatatgtc  28740
atgtaaactt tgcccatttt tttattcttt tttccttatt cttatctgac tgtgttatct  28800
caaaagacct gtcttcaagt tctgagattc tttcttctgc ttgatctagc ctattattga  28860
tgctttcaag tatattatgt atttaatatt tcatcaagta tattatgtat ttcatcaata  28920
aattatttcc agaagttgtt tggttctttt atatgtatct tttttgata aacatctcat   28980
taatatcctg aattgttttt ctgatttctt tgtatttttt taaaacaaat tttaaagttt  29040
gtatctcacc tccctgagct tttttaatat cacaacttg  aattcttttc ccagaatttt  29100
gtaagtttac ttttgattgg gatctgttgc tggagaatta ttgtgttcct ttggtggtat  29160
catattttct tgttttttca cgtttcctgc atcctgaagt tgatatctgt gcatctgatg  29220
tgatatttgc tgtttctaat ttttcaaatt tgcttttgta ggggaggact tttcctgaag  29280
atgtatttat ggtgtcagtt aggtggggca ctttggcttt aattctgggt gcatgcagta  29340
gtgtagtttc tgtatgactt tcagctgtaa atatcatcag tggtatctgt catttcctca  29400
gtgctttagg atgcggttac tagtggagat ttgctaggga ataggatgcc atgtgggcca  29460
atgttcggac ccaagtgttg gcagtggtgg gctgagtttg cctgtccttg ggcccagggt  29520
gatgttgctg gcaccagtgt tagcaagccc aatcaggcca gttattgggt ctccaggtgg  29580
ctcacttggg tgccagaaat ggcgggtgac ctggttctca ggctacttgg cagcaagtgg  29640
gggcatgggt gatggcagta gtagtggtgg gacaaccctg tgggacacaa gcagtctgtg  29700
ccagtgttgg ctgtgggtgc ggtgattggg tggatcagtt tccaggtctg caggtggctt  29760
accagctgtg atgttagtgg caggttgagt gggcctgact tcagacacca ggaagagtgc  29820
tcagctgcta ttggtggtgg actggctgag catccgggta cctgatggca ggcttgtgta  29880
ctgagagggt gacgctgggc cagatggact tgtcctcagg cctccctgtg gtgcatgtga  29940
gtgctggctg tggtaggaag aggtagagta ttcctaggct actggtggaa tgcttaggtg  30000
aggacagtgt ggctgtgctg tggaccagct acttgggaca gcagtgttgt tttcagttgg  30060
gagcagccac agagaggtgg ctggggcaca tgcagtttgc tcatgcctca gcccaaagca  30120
gccagcagca gccatagccg catgcactgg aatttgtcct cagggaacca gaaaatgcct  30180
ggctgctcct ctattggggg tgtcaggtcg ctgccagtgg ctcctgcttt ggcttaggca  30240
acagtggcca cagagcaaga tgcagtctgg gaggggctgg gctctcaaaa tagtcttgtg  30300
```

-continued

```
ctgtggctgc ttaggactca gtggtttata gtactcagtg tgaacttact ctctggagta  30360
atgccatcac actgtctcca ggcagcttcc tatgttagat ctagagccta cgagaatcaa  30420
gggactcctg tagctaggat tgtgggagtc ttcagaggga atgtggactg ctggggttct  30480
ctcacttact cttttcctgc attagggagt ctctccaggc ttccaggcaa tctcagccaa  30540
acaggctgcc ttgcttctgt ctccttcctt gctttggtgc atcctgtcac ttgtttgtta  30600
aattctagtg ttctctcttt gatgatctct tcaaaatgtg attatgtaat tcctgcttag  30660
gtttctctcc atggaagagg agaagaccag aggcatctag tcagacatct tgaagccact  30720
ccccatgata ctgtcttagg aaaacaatca acatgtagca ttcatggata ccaaagggaa  30780
aatgggtaaa cacatttttt ttttttaga cggaatctcg ctctgtcacc caggctggag  30840
tgcagtggcg tgatctcggc tcactgcaag ctctgcctcc cgggttcacg ccattctcct  30900
gcctcagcct cccaagtagc tgggactata ggcgcctgcc accacacccg gctaattttt  30960
tgtatttttc agtagagacg gtgtttcacc gtgttatcca ggatggtctt gatctcctgg  31020
cctcgagatc tgcctgcctc ggcctcccaa agtgctggga ttacaggcgt gagccaccgc  31080
acctggccag gtaaacacat ttttttcttt ccacctttta ttttaggttt gggaggtaca  31140
ggtgaaggtt tgttacatgg gtaaattgtg tgtcattagg gttgagtgta cataatattt  31200
catcacccag gtagtgagct tagtacccaa taggtagttt attgattctc accctcctcc  31260
caccttccat tctcaaataa gccctggtgg ccattgttcc cttctttgca tccatgtgta  31320
ctcattgttt agttcccact tataggtgag aagatgcagt atttggtttt ctgttcctgc  31380
attaattcac ttaggataat ggtttccagc tgcatccata ttactgcaaa ggacatgatt  31440
tcattccttt ctatgtttgt gtaatatccc gtggtgtata tataccacat tttctttatc  31500
cagttcacca ctgatgtgca tctaggttga ttccatgtta ttgtgaaaag tgctgatgaa  31560
catatgtgtg catatgtctt tatggtagaa tgatttttgt tggtttgggt atatacccaa  31620
taatgagatt gctaggtcac atggtggttc taagttcttt gagaaatctc caaactgctt  31680
tccacagagg ctgaactaat tacattccca ccagcaatgt ataagtgttc tctgttttcc  31740
acaaccttac caacatttgt tattttttca ctttttaata atagccattc tgtctgctat  31800
gagatggtat ctcattgtgg ttttgattgc atttctctaa tgattagtga tgttgagcat  31860
tttttcata tgcttgttgg cctcatgtat gtcttctttt gagaagtgtc tgtttatgtc  31920
ctttgcccat tttttaaggg ttggtttgat ttttgtttgt tgatttgttt aagttcctta  31980
gagattttga atattagaac tttgttagat gcatagtttg caaatatttt ctccttttct  32040
gtaggttgtc tgttttctct gttgatatat atttttttgc catgcagaag cactttagtt  32100
taattatgtc ccacttgtca atttttgttt ttgttgcaat tgcttttgga gacctcatca  32160
tgaaatattt accaacacct atgtcagaat ggtatttcct aggttttctt ctagagtttt  32220
tatactttta ggttttaagt ttaattcttt aatccatatt gagttgattt ttgtatatgg  32280
tgaaaggtag ggtccattt tcaatcttct gcatatggct agccagttat agcatttatt  32340
gaatagagaa tccattcccc attgcttgtt attgtcgact tcattgaaga tcagatggtt  32400
gtaggggtgt ggctttatat ctgggtttc taacctcttc cattggtcta tgtgtctatt  32460
tttgtaccag taccatgctg ttttggttac tgtagccttg taatatagtt tgaaatcagg  32520
tagtgtgatg cttccagctt tgttctttt acttacggtt gttttggcta tttgggttct  32580
tttttgattc catatgaatt ttagaatgta tattttttaa ttctctgaaa gatatcattg  32640
gtagtttgat aggaatagca ttggatctat aaattgcttt aggcagtatg gcccttttta  32700
aaaattttgt attaattttt tttttttttg agacagagtc tcactctgtc actcaggctg  32760
gagtgcagtg gcatgatctt ggttcactgc aacctccgtc tcctgggttc aagtgattct  32820
cttgcctcag cctcccaagt agctacgatt acaggtgcac accaccacac ccagctaatt  32880
tttgtatttc tagtagagat gaggtttcac catgttggcc aagctagtct caaactcctg  32940
acctcaagtg atccacctgc ctcagccttg caaagtgctg ggattacagg catgagccac  33000
catgcccgca gtatggccct tttaaaaata tttattcttc ctatgcatga gcatggaata  33060
tttttccatt tgtttgtatt gtctctgtct tctttgtttt gtatttctct atagagatca  33120
ttcacctccc tggttagctg tattcatagg tattttatcc ttttgtggct attgtgaata  33180
ggattgcatt cttgatttgg ctgtcagctt gacattgttg gtgtatagaa atgcttctga  33240
tttttgtacc ccgaagcttt actgatgttg tttaacagtt ctaaaagctt ttgggcagac  33300
tatggagtat tctaggttta aactcatatc atctgtgaag agagatagtt tacttcctct  33360
cttcctatat ggatgccttt tatttccttg cctgattgct gtggctagga tttccagtac  33420
catgttgaat aggaatgata ataatggaca tccttgtctt gtactggttt tcaaggtgaa  33480
tgcttccagc ttttgctcat tcagtatgat gttggctgtg ggtttttcct ggcggctctt  33540
attattttgt ggtatgttcc tttgatgcct agtttgttga tgacttttaa catgaaggga  33600
tgttgaatgt tgtcaaaagc cttttctaca acaattgaga tgatcatgtg gttttttttgt  33660
ttgtagttct gtttatgtga tgaatcacat ttattgattt ggatatgttg agccaacctt  33720
gcatcccagg aataaagcct acttgatcgt ggtaagttag gtatttgatg tgctgctgga  33780
tttgatctgc tagtatttttg ttgaggattt ttgcatttac tttcatcagg gatgttggcc  33840
tgaagttttc ttttttgtc ctgtctcttt gccagatttt ggtatcagtg tgatgctggc  33900
cttatagaat gaggagtccc tcctccttga tttttggcat agtttcagta tgattggtac  33960
cggctcttgt ttgtatgttt ggtggaattt gtctgtgaat ccatctggta cagggctctt  34020
tctggttggt aggtttttta aattactgat tcaatttaag aacttgttat tggtctgttc  34080
aggtatttaa tttcttcctg gttcaatctt aggaggttgt atttttccaa gaatttacca  34140
tttcttctac gttttctagt ttatgtacat agaggtgttc aaaatagtct ctgagggtgt  34200
tttgtatttc tgtggggttg gtggtaatgt cccctttgtc atctgagatt gtgtttattt  34260
ggatgttctc tctctttatt aatctagcta gttgtctatc aatcttattt attctttcaa  34320
aaaaccagct ttggttttgt tgatcttttg tatggatttt tgcatctcaa ttttattcag  34380
ttcagctctg attttggtta tttttttctt tctgctagct tttgggttgg tttgctcttg  34440
ttttttctac atcctctaga ggtgatgtta ctttgttaat ttgagatttt tctaacattt  34500
tgatgtaggt gtttaatgct acaaactttc ctcttgacat tgttctggct gtgtcccaga  34560
cactctggta tgttgtatct ttgttttcac tagtttcaaa gaatttcttg atttctgcct  34620
taattttcag aatgccaaaa gtcattcagg attaggttgt ttaatttcca tgttattgta  34680
tagttttaag agatcttcct ggtattgatt tatattttat gctgtggcct aagagtatgg  34740
ttagtatgat tttggttttt tgaatttgtt taaaattgct ttatggttga gcatgtggtc  34800
aatcttagag tatgtgctat gtgcagatga gaagaatgta tatcctgttg ttcttgggtg  34860
taatgttatg tagatgtctg ttaagtccat ttggtcaagt gtcaagttta ggtcatgaat  34920
atctttgtta gttttctgcc ttgattatgt gtctaacatt gtcaatgggg tgttgaagtc  34980
tcccactata ttgtgtggtt atttccatct cttcataggt ctttaagaac ttgtcttatg  35040
```

-continued

```
aatctggatg atccagtgtt ggatctgaaa agagtaataa aaacattatc attactatca  35100
ttattattta ttgtggttat tttatatttt gaatgaactt ctaagctaaa agatttatct  35160
tgaaagattc caactgttgg aattcacttt gttttaaata gaaataaatg tgtttcaaat  35220
gaaagtctga tgatttaatg atcacaaaag tgatgagttt aataaatgag tttttctca  35280
cctgctcaat ggcactcaat gaaggtttga aatgcctttt tttcctgaaa ttctttaagt  35340
attataccct ttgattttct agaaaacttt ccttagtcgg cattccagct tgtgttaaaa  35400
aataaagagg aagtccttcc ttcttaaact ggacatatgg caacattttt tgtgtgtgat  35460
ttcatatttg taggacataa acctgaaaat tatattcatt aaatttatta tgtgaatgag  35520
gttactcttc tttaaagata aattaactct actgcaagaa aattgtttca tcaattacac  35580
tgcaatgtaa gtaaaatgat acagatgatc tttgaatttt ggaagtattt gatttttttt  35640
tcctattctg ctaaggaaga aagactgact aatgttacag aactttctaa tttgccttgt  35700
aaatgaagca tgtgttgtga atttaaatc ttttcttccg ttggctttgt ataagtgttt  35760
cccaattttt ttttgtgggg ggtggggggt gcgttaattc ttgctctctt ctcaccaaag  35820
accttttag acattttttt ttgatcatcc tccaccacac atatactgta aatcagttta  35880
tgtatcacat atatatctgc actctgtact taaaaaagga aaattttttt ttaactttca  35940
tcaggtatca cccccattga gaatgcttgc tttctgttgg ttttgttttt attgttttta  36000
aagacaaaat catatagaag aaagagctta acctctggag tcaaaccagt cggatgttgg  36060
tttgaatcct gtttttttca cttagtaatt attcaaccca agtgattaag tgattaactt  36120
aatctctctg agactcagtt ttctcattta agagatagag attgtgattc ctatgtgaag  36180
tatttgaagc ttaatgtgat tagtgggtat gaaaactcca agcacagtcc taaaagttga  36240
ataaatatta gcttaaggaa gtcactgcat gcaatcacta ttattttcct aagctggatt  36300
tctgataatt tcatcactcc ctctggccac accaaagaat aagaacagtc ttttattcag  36360
gtaatattta catgtttttct ctgtggcaag tactgtactg atttttttta atgtattatt  36420
tcatattctt ctcacaacaa tcttataatg tagcattttt atcccatttt cagctaagat  36480
aactgtggtt ttgcaaaatt tgtaacttgc ctttcacaga gctagtaggc aataaataga  36540
ggccgatgac tagtttctct attaccaggt tttttttttt tttttttttt ttttggatgg  36600
gggacagggt ctcactctgt cacccaggct ggtgtgcagt ggtgcaatct cggctcacgg  36660
caacctctgt ttcccaggct caagtgatct tcccaggtac tttaaaagat agaaagatgc  36720
tcatcctagt gacagaccaa gagacaatac aacccaaatt ggacaattaa ggtgccgtga  36780
ttccctacaa gtattgcttt attcccctct gttgccaaag tcctatactg agacattcat  36840
aagtccctca tggggactaa tagatcaatt taaagaataa taaataagaa gtcaggaaat  36900
attcagtgaa atatagaaaa tattttttct gtatccccta acaattgtgt acttatttat  36960
cctttaaact tgaatatggc atatattaca gactagccca aatctaaatg tactttcaag  37020
agtcttgact cttaagtagc tatttgaagt taataagatg tggttacagg ggtctttatg  37080
tcttattaca tgcccctata catgacaaac ttaagtccca ttataaagtg acatcagtta  37140
tctgcctgtt attcaggttt aagtcagata atataatcat ataatctttc tgtgatacgt  37200
ttagtctgga aaaggaagta tgtgaatttc ccttattaaa aaaattgaag aaatacagag  37260
gtacagaaaa tccaacgatg atggcaagac acttaaaggg tcctgtggat gtctctctga  37320
ggaagcagag ttgaatctgc atttacaaaa tggaaaattt aagggttact caagcatact  37380
gtttttcaaa tcatctacga aaatctcttc ccagggtgcc ttcacttgtc cacaggccct  37440
ttattctgtt acattaagta tgatataagc aagaacaaaa cctttccata actttttgtt  37500
ttcatagcac atgcattgca tttccacttt gttagctctg caagttagac cttttgaagt  37560
gtctgggtca tcccacattt cttcaaaaaa gatgatgtgc atcctctagg tcactccagt  37620
tcttggaggt aggtagatag aattctaagt tgggttcttt ggcagtgaag atgataccct  37680
atatattaat gtagtatctg tctaatgtaa attttgtttg atgaatatca ggtattttat  37740
tgaaaatatt tcaaacagtt aaaattatgg cctgaatctg gggctagaag tgagtttttc  37800
tatggcaata aactgactta ccctttcttg gtctcagttt tcttatctgg aaacaagata  37860
ttaagtgcaa tttaataaat atttgttaaa cactttctac tgtttgccat gtactgtgtt  37920
aataatgaga ggtgatcaaa tgagataata ggtggcaaac tgctttgcaa tgttttcaac  37980
actgcaatac agttctacat gatggggaac cttactaaaa tactcctttt gtgggggaga  38040
aaaccttttt ctaacattat gttattttcc cacctaagag ctcttcagtt taatcttagg  38100
aacattggaa tcataattat tatttcattc attatttcat actttcattt ttcccaagtt  38160
gtataaatct taatgttgat tcacctttgg ttttctgtag ataccaagtg aattttgaga  38220
tcataaacag ttgcctttga acctgaaagt tttgtttcta atttgggaga taatatgctc  38280
ttattaattt actgagaaga tacgtagaat tttgtttttc atatttctgt gttttgcctt  38340
ggttttctgt taaaccatca gcctctacac tttcttctag aactatgtat atgtgttgag  38400
cattgttctg ggaatagcct tttacttctg tcatctggat gttctagatc actctgaatt  38460
ttctgtcttg atttagtatt caaataaaaa ataagatatt gaaagtggtg gaattagtgg  38520
gaactggtga cagaaagggg gaaacccaaa attttttagg agctgtgatt tatttcatgg  38580
atagtctctc taagttaatg atacaattct aggggatcag ttaaataaac ttctaaagta  38640
aaatactgta aaaacttacc tgtggtagaa atagctgttt tttaaatcac aattttcaca  38700
tggcagtgca attgtacagt gtctctattt tgctgatttg gagccaaata cactcattag  38760
tcacgttaga ttcagttact attctagtgt catctgtcat ttcctttgta gtaaagacca  38820
atagagttga gtccaaggac actgggcagg gttggtgggg gtggtggtgg gagggggggct  38880
gttggtgagg aaagagagaa tgaggatggt gagagaaaag ggcaaatggg tgcatttgag  38940
aagaaagatt gtgtaagcta taaaaatgat ttgatgttga tcaacttatt tgaccaatta  39000
tttgctgttg ttcagctcaa aatagtgctt tgaatcttaa aagtgaatat aatttttgaa  39060
atgaaattta atctaccata gactgaacac taaaaagcat attctgtagg caaagtaaat  39120
atagtttgcc ctccaatctc agatgataat agtacaggca tatttcctgt gatggagaaa  39180
tgtctacata tctgttatat ctactgtaaa ctaggtaaat gtccttccca ttaaccacat  39240
atgttaatgt tcaacttcct tctgagactc aatttactca tctaaaaaat gaaagtgaac  39300
tctaagatgc tttctagctc taaaataaca taattctgtc accatatttg aatgctcaac  39360
gatcaaaaca tttaaaatcg agcatgattg ggttgaaaca cttaagaagc ctctcaaacc  39420
tgtcaaaaaa ttttatttga gcattgtgat attctaaata tatttcttcc tttttctttc  39480
gaagaaaaca ggacaaataa aacatgcatt tgtcaaaaat ttgtgacata aggaagccat  39540
atacaaaatg caattaatat ctcctatttg taactcactt cataaccagt atgtatgtca  39600
ttgtgaaact ataatgtaat tttaattgct catgtttcta ttaactgtgt taccatatct  39660
tttccccttc aaggatttct tgctggtact ctattaattg gtaccctaat tctagtcatt  39720
ggactatgga aaatcagagt gagcagaaat tctgatgatt tttaaaaatt tattcctagt  39780
```

-continued

```
ttatttccag taaaatttgg tactgtatca gtagatgact ctcttagctt tatttaaatt  39840
ttggcgtgtc tctgtattca tttttgtctg taattactat cctggattaa cagacttcat  39900
gtctgttttt tctcaatata ttcaaaggcg catttcaaag caaagtgact tgaagtctca  39960
ttttgtgatc tattaatcca ctgatttttt tccactcagt gtaatttatg atagtatcta  40020
gtgttgcaca gaagcaaaga aatctaggaa aaatcaacct ctaacatact gtgaaattgc  40080
ctgtgattag ggcttttttct cacttatatt aatagatgcc agtccagctc aaaacagcac  40140
agtggttaag gcagcagaca aatgggggaa atatagtacc tacctcatat gattataatc  40200
atatatcaaa tgagttgcca cctgtcaagt gcttagaaca ttgcttggca catagtaagc  40260
actcagatat taaaacaaca acagcacaca cacacatcag tattatttaa aatatctaat  40320
ctgcattgaa tatacataat gttaagtata aatgtcacga ttggctctga tgtgtcctgt  40380
agacagatga tgatttaaat cgaccctctt ctgttttgta gttttaactg ttcagaaaac  40440
tagttgtgga atttatacaa acttgagtta tttctaagct gccctaatgc ctgtccgttt  40500
ttcccattaa taagaaaact attaatttaa tgctgttatt aaattgtctg ttttaattct  40560
ttagatgatg tgacctatct ccttttttacc ctctacaatt tttctactta aattaagaat  40620
attacttaag cctattataa gttaaagcat gtaaatattc tttaactcac taaatgagtc  40680
agtcttgtag aaaaatattt gaccattagg tccaggggag tgattaataa tttttacagg  40740
catttgttta atatcaacaa aatattctag ctgtcatgat agcaaatata gtaagacata  40800
actttttctc cagatatatc agaaacgttt taggaatgtg atttagagcc tagcaaaaac  40860
tcacagttag tactaagtca tctaaagtga gttggtatgg aagcatcagc aaagctactc  40920
tgaaaaaaaa taaaaccacc aatcttacgt actttcttgt acttgttcca actttccttt  40980
tgaaatactg ttatcagttt atcaagttat aaagtatcaa tgtatagagt attatcaatt  41040
taccaaagct actgctttga gactccctgg atcggtggga atggagactg ggcgggggag  41100
ggcggagggc gggcggggc agggcagcaa gatgtgataa gtttaccagg tgctgtctct  41160
tggctttcat cagtttcttt acatactttg gtaaggtgat tggctgtgat acttgtatgt  41220
cctattaagg acataaagta ctggaacatc gaaggaggga atacagtaat ttctgcttat  41280
cctcggttgg ggggcagggt gtttcaagaa cccccagtga atgcttgaaa caacagatag  41340
tgcctaaccc tatatatgct gtgtttttc ctgtatgtac atacctatga gataaagttt  41400
aatttataaa tgaggcacag taagagatta acaccaacga ataatcaatt agaacaattt  41460
attgtagcaa aagttatgtg aatggggtct ctctctctct caaaatatct tattgtattg  41520
tactcaccta ttttcagatt gcagttgact gtgggtaact gaaaccacag ataagcagac  41580
taatgtattt gttttgaatt gtattttggg gttttgcagt gaacttaatt gcttattttc  41640
tgaattagag ggaaagtcat gcaaactcct aagaaagaat ttgtcttttt tatgtgcaca  41700
taaaaaacac tccacttgct ttattttgga aacataagct gttgagggta agagctagct  41760
ttatatatgt ttggctagcc tcctgatttc atactgattt aattaaatat ttgatcttaa  41820
ttaagacagg atatagttaa tgtgcaagtg ataatgtggt ttcatttaat gattcttcat  41880
gtttgcctat cagaggattg atttatttct tttagaagag ttaggtctgt atgataaatt  41940
ttagtttagg gatggaagtg taagcagatg cctgacttcg ttttttgatt gaaatgacag  42000
ttacataatt caattcaata gttttttttct tctctactat tcagctctta taatgcacat  42060
gagagcaaca aagtactcaa tgttgtgttt gaccatttaa gtgtgactgg tggtacctca  42120
gaaataagac tttctggtaa attataaaag gtatatatgg tttaataaaa ttacatttct  42180
gtatcttgca aaatatccat taataccctt ggctaggggg ttcttcatga cttttaaagg  42240
ataatagagg cttaagtctc tgtcactaga gttgtttttt tctttgttga atgactaata  42300
cattgaatct ctcattacta tgacatatcg tcagttctgg acttggtagc agtaatgctt  42360
atcatctcat cctacatttt gaactcagtt tattgtaacg attagatgct ataatgccac  42420
aaatattcgg ggggaaaggg atgatacatt aggactttta aagagaatgc cttcattatg  42480
ataatttgca tcatgagatg gttgacctac cttgtatttc tccttttgct tggtggcttt  42540
tagagttttc aatgtttaag aaaaattata atatgtgcta agatatcctt ttataggtca  42600
tgtttataga tcttaaaaga catctcatat ctttatacaa aattatcaca caaaaaataac  42660
ttggtgtaaa tgtatctgta aaactttctg agtgtcttca tctcttaatc ttctcttcca  42720
catgtagtag tattcagggg tttttattta tttttatatt tttttaacat ctcccacact  42780
taggaattca ttgactttta atctgaaggt accttaattc attctagctt agccactgtt  42840
caactcgaga aactaaaaac tccacgtcac attttagttg ttgctgtagc tgataaaccc  42900
cacctgtaga atcttgtcca tattctatta ctcattattt tttttgtttt gcaccccaaa  42960
ttaactgatt ctttttggtg atttatcaca tagtaactaa aaatttatat ttatcactag  43020
taaataaaat cattttgatt ttaacttttt tttttttttt tttttaattt tcagggcaca  43080
cgtgtttcac gttgacaggt ttgcttggga cgctagtaac catgggcttg ctgacttagc  43140
caaagaagag ttaagaagaa aatacacaca agtatacaga ctgttcctag tttcttagac  43200
ttatctgcat attggataaa ataaatgcaa ttgtgctctt catttaggat gctttcattg  43260
tctttaagat gtgttaggaa tgtcaacaga gcaaggagaa aaaaggcagt cctggaatca  43320
cattcttagc acacctacac ctcttgaaaa tagaacaact tgcagaattg agagtgattc  43380
ctttcctaaa agtgtaagaa agcatagaga tttgttcgta tttagaatgg gatcacgagg  43440
aaaagagaag gaaagtgatt tttttccaca agatctgtaa tgttatttcc acttataaag  43500
gaaataaaaa atgaaaaaca ttatttggat atcaaaagca aataaaaacc caattcagtc  43560
tcttctaagc aaaattgcta aagagagatg aaccacatta taaagtaatc tttggctgta  43620
aggcattttc atctttcctt cgggttggca aaatatttta aaggtaaaac atgctggtga  43680
accaggggtg ttgatggtga taagggagga atatagaatg aaagactgaa tcttcctttg  43740
ttgcacaaat agagtttgga aaaagcctgt gaaaggtgtc ttctttgact taatgtcttt  43800
aaaagtatcc agagatacta caatattaac ataagaaaag attatatatt atttctgaat  43860
cgagatgtcc atagtcaaat ttgtaaatct tattcttttg taatatttat ttatatttat  43920
ttatgacagt gaacattctg attttacatg taaaacaaga aaagttgaag aagatatgtg  43980
aagaaaaatg tatttttcct aaatagaaat aaatgatccc attttttggt atcatgtagt  44040
atgtgaaatt tattcttaaa cgtgactact ttatttctaa ataagaaatt ccctacctgc  44100
ttcctacaag cagttcagaa tgccatgcct tggttgtcct agtgtgaata attttcagct  44160
actttaaaat tatattgtac tttctcaagc atgtcatatc ctttcctatt agagtatcta  44220
tattacttgt tactgattta cctgaaggca atctgattaa tttctaggtt tttaccatat  44280
tcttgtcatc ttgccaatta cattttaagt gttagactag actaagatgt actagttgta  44340
tagaatataa ctagatttat tatggcaatg tttattttgt cattttgctt catctgtttt  44400
gttgttgaag tactttaaat ttcatacgtt catggcattt cactgtaaag actttaatgt  44460
gtatttctta aaataaaact tttttcctc cttaaccaca gttatcacaa ctagcagttg  44520
```

-continued

```
tgatagtttc taatttccta atagtttcta atattaggaa attctttgaa ctttcctaga  44580
agttctaaga gtaggcacat atccatccac ctattcattc attcatttgt taaatatgag  44640
ggcccgctct gcctattctg taataaccca gtgcttccag ggatagcaat aacactggct  44700
cagctattca gaaaaaaagc tgagtgccta ctatgtgcaa gttgtcatat gctaaaatgt  44760
gagcttacca agataactgc aagtgtctgc cctcaagttg cttatagttt gccacaggaa  44820
gaccaaaata tatacttatt gagagaaaga agataaagtt acgagtgtta cagccccgaa  44880
tatggtgggt gcttaagctg tttgttaagc agttgagtgg cagggaggga gatattcaag  44940
gcagaaagct gattgagaaa gcagtaatag atgagattat agtggcagga tggtcgaagt  45000
aggaaaggct tagagcaagg gctagactat gtcatgtgtt ctgtgtagaa gtgaaaattt  45060
gtaagctcta gactttttat tctgctcgat ctaattagaa tcagtgagca taaaataggt  45120
ttctaatagc aagaacttgc tatttagata agggtaaaag cggaaatact attaaacagt  45180
catttacctt gaagaaaata taaacagtag gcttgtgagg gtaaagatat tttcttgtag  45240
gatttatatt taccgtgtat cctgtagtta tgaggttgag tggttttatt tttgcttaag  45300
ataacctctc ctgtgagatt ttactttgat tgcaaaggtt gtattgcttt tcctcttgag  45360
actgatgtat ttgttacagc aagttatacc tgctcactgt agaaatttga gttttataat  45420
atttagcccc ctatcactgt cacttttctg ggaatacttg aacatgaata atttttgtct  45480
tgtcacaccc tagccctgtt tgctttggtt aatgtccaat gtgcaaatgc ctcattttcc  45540
tcccacccat cctgagtgtt ttcttcctcc ttaccgaaac taaaaacagc cccttccctg  45600
aaggtactgc ttcctttgca gcctattcca gtggtggctg gtttatttc atccatatga  45660
ctcattgtta agaggtggcg gaggtgtttt ccttgttcct ttgtcatgtc ttccatctca  45720
acccccacac acatctcttt aaaaagagta actgtccatt cactctggta gggtaattta  45780
ctaaaatgtc aaatgttttt cctataattc tccttggtga aaagcatgga ttctggagac  45840
aaatcggagc cctggcattt atcagctgca ggactcaagg gatgttcctt gtcagtgtac  45900
cttagttatc tatgtgtaaa gtgggcctaa aatcagtacc agcctcatag gatttgcaat  45960
gagaattaag ttaatacacg tagagcttaa aatagtgcca gccatgtagt aagtgctcag  46020
taagttttag ctctttttag tgcacaggtg gagagattgc cttaggtgga agcatgcagg  46080
gcttcagtac atactaggag ggaactgttg caggtgggtt ggagatgccc atggtggcag  46140
cttttggaaa ttgatttcac atttcttctg ttttctcagg gacatataca tcaaggtcat  46200
cataaaaatg atgacacatg aggaggtgtt atgtttgaag acaggcagag aaggaaagga  46260
ctagagacat ttagtcaatt agcaggcaat gctaaagacc cagttgaggt gagtgctcat  46320
gaatttagag tgcaatcatc aagcttcgtt ctgagttttt ctgcagtcat atttagcttt  46380
ctagatacag tctcagaaaa aaccagttgc ttggatttaa tcatgattgg gtgttcccag  46440
gtgaatttga tgacgtgagt tgagcatgtg cacaagggag tgattaaaat gatgg       46495

SEQ ID NO: 2           moltype = DNA  length = 2796
FEATURE                Location/Qualifiers
source                 1..2796
                       mol_type = genomic DNA
                       organism = Homo sapiens
SEQUENCE: 2
agcgagctcc tcctccttcc cctccccact ctccccgagt ctagggcccc cggggcgtat  60
gacgccggag ccctctgacc gcacctctga ccacaacaaa cccctactcc acccgtcttg  120
tttgtcccac ccttggtgac gcagagcccc agcccagacc ccgcccaaag cactcattta  180
actggtattg cggagccacg aggcttctgc ttactgcaac tcgctccggc cgctgggcgt  240
agctgcgact cggcggagtc ccggcggcgc gtccttgttc taacccggcg cgccatgacc  300
gtcgcgcggc cgagcgtgcc cgcggcgctg cccctcctcg gggagctgcc ccggctgctg  360
ctgctggtgc tgttgtgcct gccggccgtg tggggtgact gtggccttcc cccagatgta  420
cctaatgccc agccagcttt ggaaggccgt acaagttttc ccgaggatac tgtaataacg  480
tacaaatgtg aagaaagctt tgtgaaaatt cctggcgaga aggactcagt gatctgcctt  540
aagggcagtc aatggtcaga tattgaagag ttctgcaatc gtagctgcga ggtgccaaca  600
aggctaaatt ctgcatccct caaacagcct tatatcactc agaattattt tccagtcggt  660
actgttgtgg aatatgagtg ccgtccaggt tacagaagag aaccttctct atcaccaaaa  720
ctaacttgcc ttcagaattt aaaatggtcc acagcagtcg aattttgtaa aaagaaatca  780
tgccctaatc cgggagaaat acgaaatggt cagattgatg taccaggtgg catattattt  840
ggtgcaacca tctccttctc atgtaacaca gggtacaaat tatttggctc gacttctagt  900
ttttgtctta tttcaggcag ctctgtccag tggagtgacc cgttgccaga gtgcagagaa  960
atttattgtc cagcaccacc acaaattgac aatggaataa ttcaagggga acgtgaccat  1020
tatggatata gacagtctgt aacgtatgca tgtaataaag gattcaccat gattggagag  1080
cactctattt attgtactgt gaataatgat gaaggagagt ggagtggccc accacctgaa  1140
tgcagaggaa aatctctaac ttccaaggtc ccaccaacag ttcagaaacc taccacagta  1200
aatgttccaa ctacagaagt ctcaccaact tctcagaaaa ccaccacaaa aaccaccaca  1260
ccaaatgctc aagcaacacg gagtacacct gtttccagga caaccaagca ttttcatgaa  1320
acaaccccaa ataaaggaag tggaaccact tcaggtacta cccgtcttct atctgggcac  1380
acgtgtttca cgttgacagg tttgcttggg acgctagtaa ccatgggctt gctgacttag  1440
ccaaagaaga gttaagaaga aaatacacac aagtatacag actgttccta gtttcttaga  1500
cttatctgca tattggataa aataaatgca attgtgctct tcatttagga tgctttcatt  1560
gtctttaaga tgtgttagga atgtcaacag agcaaggaga aaaaaggcag tcctggaatc  1620
acattcttag cacacctaca cctcttgaaa atagaacaac ttgcagaatt gagagtgatt  1680
cctttcctaa aagtgtaaga aagcatagag atttgttcgt atttagaatg ggatcacgag  1740
gaaaagagaa ggaaagtgat ttttttccac aagatctgta atgttatttc cacttataaa  1800
ggaaataaaa aatgaaaaac attatttgga tatcaaaagc aaataaaaac ccaattcagt  1860
ctcttctaag caaaattgct aaagagagat gaaccacatt ataaagtaat ctttggctgt  1920
aaggcatttt catctttcct tcgggttggc aaaatatttt aaaggtaaaa catgctggtg  1980
aaccaggggt gttgatggtg ataagggagg aatatagaat gaaagactga atcttccttt  2040
gttgcacaaa tagagtttgg aaaaagcctg tgaaaggtgt cttctttgac ttaatgtctt  2100
taaaagtatc cagagatact acaatattaa cataagaaaa gattatatat tatttctgaa  2160
tcgagatgtc catagtcaaa tttgtaaatc ttattctttt gtaatattta tttatattta  2220
tttatgacag tgaacattct gattttacat gtaaaacaag aaaagttgaa gaagatatgt  2280
gaagaaaaat gtatttttcc taaatagaaa taaatgatcc catttttttgg tatcatgtag  2340
```

-continued

```
tatgtgaaat ttattcttaa acgtgactac tttatttcta aataagaaat tccctacctg  2400
cttcctacaa gcagttcaga atgccatgcc ttggttgtcc tagtgtgaat aattttcagc  2460
tactttaaaa ttatattgta ctttctcaag catgtcatat cctttcctat tagagtatct  2520
atattacttg ttactgattt acctgaaggc aatctgatta atttctaggt ttttaccata  2580
ttcttgtcat cttgccaatt acattttaag tgttagacta gactaagatg tactagttgt  2640
atagaatata actagattta ttatggcaat gtttattttg tcattttgct tcatctgttt  2700
tgttgttgaa gtactttaaa tttcatacgt tcatggcatt tcactgtaaa gactttaatg  2760
tgtatttctt aaaataaaac tttttttcct ccttaa                            2796

SEQ ID NO: 3            moltype = AA  length = 381
FEATURE                 Location/Qualifiers
source                  1..381
                        mol_type = protein
                        organism = Homo sapiens
SEQUENCE: 3
MTVARPSVPA ALPLLGELPR LLLLVLLCLP AVWGDCGLPP DVPNAQPALE GRTSFPEDTV  60
ITYKCEESFV KIPGEKDSVI CLKGSQWSDI EEFCNRSCEV PTRLNSASLK QPYITQNYFP  120
VGTVVEYECR PGYRREPSLS PKLTCLQNLK WSTAVEFCKK KSCPNPGEIR NGQIDVPGGI  180
LFGATISFSC NTGYKLFGST SSFCLISGSS VQWSDPLPEC REIYCPAPPQ IDNGIIQGER  240
DHYGYRQSVT YACNKGFTMI GEHSIYCTVN NDEGEWSGPP PECRGKSLTS KVPPTVQKPT  300
TVNVPTTEVS PTSQKTTTKT TTPNAQATRS TPVSRTTKHF HETTPNKGSG TTSGTTRLLS  360
GHTCFTLTGL LGTLVTMGLL T                                            381

SEQ ID NO: 4            moltype = DNA  length = 22
FEATURE                 Location/Qualifiers
source                  1..22
                        mol_type = other DNA
                        organism = synthetic construct
SEQUENCE: 4
ctactccacc cgtcttgttt gt                                           22

SEQ ID NO: 5            moltype = DNA  length = 22
FEATURE                 Location/Qualifiers
source                  1..22
                        mol_type = other DNA
                        organism = synthetic construct
SEQUENCE: 5
tttgggggtt aaggatacag tc                                           22

SEQ ID NO: 6            moltype = DNA  length = 19
FEATURE                 Location/Qualifiers
source                  1..19
                        mol_type = other DNA
                        organism = synthetic construct
SEQUENCE: 6
caggtgtggc atttcaagg                                               19

SEQ ID NO: 7            moltype = DNA  length = 20
FEATURE                 Location/Qualifiers
source                  1..20
                        mol_type = other DNA
                        organism = synthetic construct
SEQUENCE: 7
accctggggt ttagtaacgc                                              20

SEQ ID NO: 8            moltype = DNA  length = 24
FEATURE                 Location/Qualifiers
source                  1..24
                        mol_type = other DNA
                        organism = synthetic construct
SEQUENCE: 8
aagtactaaa tatgcgcaaa gcag                                         24

SEQ ID NO: 9            moltype = DNA  length = 22
FEATURE                 Location/Qualifiers
source                  1..22
                        mol_type = other DNA
                        organism = synthetic construct
SEQUENCE: 9
atggtcctat caagaaacat cc                                           22

SEQ ID NO: 10           moltype = DNA  length = 23
FEATURE                 Location/Qualifiers
source                  1..23
                        mol_type = other DNA
                        organism = synthetic construct
SEQUENCE: 10
gttaccttct ttgtgtgtat gcc                                          23
```

-continued

```
SEQ ID NO: 11          moltype = DNA  length = 23
FEATURE                Location/Qualifiers
source                 1..23
                       mol_type = other DNA
                       organism = synthetic construct
SEQUENCE: 11
gctgtgaata ccagtcatga aac                                            23

SEQ ID NO: 12          moltype = DNA  length = 22
FEATURE                Location/Qualifiers
source                 1..22
                       mol_type = other DNA
                       organism = synthetic construct
SEQUENCE: 12
aacctggaga atttgaggaa ag                                             22

SEQ ID NO: 13          moltype = DNA  length = 22
FEATURE                Location/Qualifiers
source                 1..22
                       mol_type = other DNA
                       organism = synthetic construct
SEQUENCE: 13
tgtgctaata ttcttaaggg gc                                             22

SEQ ID NO: 14          moltype = DNA  length = 24
FEATURE                Location/Qualifiers
source                 1..24
                       mol_type = other DNA
                       organism = synthetic construct
SEQUENCE: 14
gcatttataa gcatctcttg ttgg                                           24

SEQ ID NO: 15          moltype = DNA  length = 20
FEATURE                Location/Qualifiers
source                 1..20
                       mol_type = other DNA
                       organism = synthetic construct
SEQUENCE: 15
tcattgaatg tctgcaaccc                                                20

SEQ ID NO: 16          moltype = DNA  length = 22
FEATURE                Location/Qualifiers
source                 1..22
                       mol_type = other DNA
                       organism = synthetic construct
SEQUENCE: 16
ctaggtgttt gtggggagag ag                                             22

SEQ ID NO: 17          moltype = DNA  length = 22
FEATURE                Location/Qualifiers
source                 1..22
                       mol_type = other DNA
                       organism = synthetic construct
SEQUENCE: 17
tctggtgggt ttctgaagag tt                                             22

SEQ ID NO: 18          moltype = DNA  length = 20
FEATURE                Location/Qualifiers
source                 1..20
                       mol_type = other DNA
                       organism = synthetic construct
SEQUENCE: 18
tttacgcaga gtccttcagc                                                20

SEQ ID NO: 19          moltype = DNA  length = 22
FEATURE                Location/Qualifiers
source                 1..22
                       mol_type = other DNA
                       organism = synthetic construct
SEQUENCE: 19
ccatttaatc ctgcaatctt gg                                             22

SEQ ID NO: 20          moltype = DNA  length = 21
FEATURE                Location/Qualifiers
source                 1..21
                       mol_type = other DNA
                       organism = synthetic construct
SEQUENCE: 20
tggaaatttg agttgctttc g                                              21
```

```
SEQ ID NO: 21          moltype = DNA  length = 20
FEATURE                Location/Qualifiers
source                 1..20
                       mol_type = other DNA
                       organism = synthetic construct
SEQUENCE: 21
tctcccagga atatggattg                                        20

SEQ ID NO: 22          moltype = DNA  length = 21
FEATURE                Location/Qualifiers
source                 1..21
                       mol_type = other DNA
                       organism = synthetic construct
SEQUENCE: 22
gcaccccaaa ttaactgatt c                                      21

SEQ ID NO: 23          moltype = DNA  length = 19
FEATURE                Location/Qualifiers
source                 1..19
                       mol_type = other DNA
                       organism = synthetic construct
SEQUENCE: 23
atgtgattcc aggactgcc                                         19

SEQ ID NO: 24          moltype = DNA  length = 100
FEATURE                Location/Qualifiers
source                 1..100
                       mol_type = genomic DNA
                       organism = Homo sapiens
SEQUENCE: 24
gtgactgtgg ccttccccca gatgtaccta atgcccagcc agctttggaa ggccgtacaa  60
gttttcccga ggatactgta ataacgtaca aatgtgaaga                    100

SEQ ID NO: 25          moltype = DNA  length = 100
FEATURE                Location/Qualifiers
source                 1..100
                       mol_type = genomic DNA
                       organism = Homo sapiens
SEQUENCE: 25
gtgactgtgg ccttccccca gatgtaccta atgcccagcc agctttggcc ttggccgtac  60
aagttttccc gaggatactg taataacgta caaatgtgaa                    100

SEQ ID NO: 26          moltype = AA  length = 100
FEATURE                Location/Qualifiers
source                 1..100
                       mol_type = protein
                       organism = Homo sapiens
SEQUENCE: 26
MTVARPSVPA ALPLLGELPR LLLLVLLCLP AVWGDCGLPP DVPNAQPALE GRTSFPEDTV  60
ITYKCEESFV KIPGEKDSVI CLKGSQWSDI EEFCNRSCEV                    100

SEQ ID NO: 27          moltype = AA  length = 96
FEATURE                Location/Qualifiers
source                 1..96
                       mol_type = protein
                       organism = Homo sapiens
SEQUENCE: 27
MTVARPSVPA ALPLLGELPR LLLLVLLCLP AVWGDCGLPP DVPNAQPALA LAVQVFPRIL  60
RTNVKKALKF LARRTQSALR AVNGQILKSS AIVAAR                         96

SEQ ID NO: 28          moltype = DNA  length = 100
FEATURE                Location/Qualifiers
source                 1..100
                       mol_type = genomic DNA
                       organism = Homo sapiens
SEQUENCE: 28
gtgactgtgg ccttccccca gatgtaccta atgcccagcc agctttggaa ggccgtacaa  60
gttttcccga ggatactgta ataacgtaca aatgtgaaga                    100

SEQ ID NO: 29          moltype = DNA  length = 100
FEATURE                Location/Qualifiers
source                 1..100
                       mol_type = genomic DNA
                       organism = Homo sapiens
SEQUENCE: 29
gtgactgtgc cttcccccag atgtacctaa tgcccagcca gctttggaag gccgtacaag  60
ttttcccgag gatactgtaa taacgtacaa atgtgaagaa                    100
```

-continued

```
SEQ ID NO: 30          moltype = AA  length = 100
FEATURE                Location/Qualifiers
source                 1..100
                       mol_type = protein
                       organism = Homo sapiens
SEQUENCE: 30
MTVARPSVPA ALPLLGELPR LLLLVLLCLP AVWGDCGLPP DVPNAQPALE GRTSFPEDTV  60
ITYKCEESFV KIPGEKDSVI CLKGSQWSDI EEFCNRSCEV                        100

SEQ ID NO: 31          moltype = AA  length = 96
FEATURE                Location/Qualifiers
source                 1..96
                       mol_type = protein
                       organism = Homo sapiens
SEQUENCE: 31
MTVARPSVPA ALPLLGELPR LLLLVLLCLP AVWGDCAFPQ MYLMPSQLWK AVQVFPRILR  60
TNVKKALKFL ARRTQSALRA VNGQILKSSA IVAARC                            96

SEQ ID NO: 32          moltype = DNA  length = 30
FEATURE                Location/Qualifiers
source                 1..30
                       mol_type = genomic DNA
                       organism = Homo sapiens
SEQUENCE: 32
tttgttaata cttttaggta gctgcgaggt                                   30

SEQ ID NO: 33          moltype = DNA  length = 30
FEATURE                Location/Qualifiers
source                 1..30
                       mol_type = genomic DNA
                       organism = Homo sapiens
SEQUENCE: 33
tttgttaata cttttaagta gctgcgaggt                                   30

SEQ ID NO: 34          moltype = DNA  length = 100
FEATURE                Location/Qualifiers
source                 1..100
                       mol_type = genomic DNA
                       organism = Homo sapiens
SEQUENCE: 34
gaataattca aggggaacgt gaccattatg gatatagaca gtctgtaacg tatgcatgta  60
ataaaggatt caccatgatt ggagagcact ctatttattg                        100

SEQ ID NO: 35          moltype = DNA  length = 100
FEATURE                Location/Qualifiers
source                 1..100
                       mol_type = genomic DNA
                       organism = Homo sapiens
SEQUENCE: 35
gaataattca aggggaacgt gaccattatg gatatagaca gtctgtaacg tatgcatgta  60
ataaaggatt caccatgatt ggagagcact ctatttattc                        100

SEQ ID NO: 36          moltype = AA  length = 100
FEATURE                Location/Qualifiers
source                 1..100
                       mol_type = protein
                       organism = Homo sapiens
SEQUENCE: 36
SSFCLISGSS VQWSDPLPEC REIYCPAPPQ IDNGIIQGER DHYGYRQSVT YACNKGFTMI  60
GEHSIYCTVN NDEGEWSGPP PECRGKSLTS KVPPTVQKPT                        100

SEQ ID NO: 37          moltype = AA  length = 100
FEATURE                Location/Qualifiers
source                 1..100
                       mol_type = protein
                       organism = Homo sapiens
SEQUENCE: 37
SSFCLISGSS VQWSDPLPEC REIYCPAPPQ IDNGIIQGER DHYGYRQSVT YACNKGFTMI  60
GEHSIYSTVN NDEGEWSGPP PECRGKSLTS KVPPTVQKPT                        100

SEQ ID NO: 38          moltype = AA  length = 4
FEATURE                Location/Qualifiers
source                 1..4
                       mol_type = protein
                       organism = Homo sapiens
SEQUENCE: 38
LEGA                                                               4

SEQ ID NO: 39          moltype = DNA  length = 12
```

```
FEATURE                Location/Qualifiers
source                 1..12
                       mol_type = genomic DNA
                       organism = Homo sapiens
SEQUENCE: 39
ttggaaggcc gt                                                12

SEQ ID NO: 40          moltype = AA  length = 4
FEATURE                Location/Qualifiers
source                 1..4
                       mol_type = protein
                       organism = Homo sapiens
SEQUENCE: 40
LALA                                                         4

SEQ ID NO: 41          moltype = DNA  length = 12
FEATURE                Location/Qualifiers
source                 1..12
                       mol_type = genomic DNA
                       organism = Homo sapiens
SEQUENCE: 41
ttggccttgg cc                                                12

SEQ ID NO: 42          moltype = AA  length = 4
FEATURE                Location/Qualifiers
source                 1..4
                       mol_type = protein
                       organism = Homo sapiens
SEQUENCE: 42
DCGL                                                         4

SEQ ID NO: 43          moltype = DNA  length = 12
FEATURE                Location/Qualifiers
source                 1..12
                       mol_type = genomic DNA
                       organism = Homo sapiens
SEQUENCE: 43
gactgtggcc tt                                                12

SEQ ID NO: 44          moltype = AA  length = 4
FEATURE                Location/Qualifiers
source                 1..4
                       mol_type = protein
                       organism = Homo sapiens
SEQUENCE: 44
DCAF                                                         4

SEQ ID NO: 45          moltype = AA  length = 4
FEATURE                Location/Qualifiers
source                 1..4
                       mol_type = protein
                       organism = Homo sapiens
SEQUENCE: 45
IYCT                                                         4

SEQ ID NO: 46          moltype = DNA  length = 10
FEATURE                Location/Qualifiers
source                 1..10
                       mol_type = genomic DNA
                       organism = Homo sapiens
SEQUENCE: 46
aggtagctgc                                                   10

SEQ ID NO: 47          moltype = DNA  length = 10
FEATURE                Location/Qualifiers
source                 1..10
                       mol_type = genomic DNA
                       organism = Homo sapiens
SEQUENCE: 47
aagtagctgc                                                   10

SEQ ID NO: 48          moltype = DNA  length = 12
FEATURE                Location/Qualifiers
source                 1..12
                       mol_type = genomic DNA
                       organism = Homo sapiens
SEQUENCE: 48
gactgtgcct tc                                                12
```

METHODS OF DIAGNOSING AND TREATING CD55 DEFICIENCY, HYPERACTIVATION OF COMPLEMENT, ANGIOPATHIC THROMBOSIS AND PROTEIN LOSING ENTEROPATHY (CHAPLE), A NEWLY IDENTIFIED ORPHAN DISEASE

CROSS-REFERENCE TO RELATED APPLICATIONS

The present application is a divisional application of U.S. application Ser. No. 16/333,561, filed Mar. 14, 2019, which is a 35 U.S.C. § 371 National Phase Application of International PCT Patent Application No. PCT/US2017/051413, filed Sep. 13, 2017, which claims priority to U.S. Provisional Application No. 62/394,630, filed on Sep. 14, 2016, the contents of these applications are incorporated here by reference in their entirety.

GOVERNMENT FUNDING

Research supporting this application was carried out by the United States of America as represented by the Secretary, Department of Health and Human Services.

INCORPORATION BY REFERENCE

In compliance with 37 C.F.R. § 1.52 (e) (5), the sequence information contained in electronic file name: Sequence.xml, 93,826 bytes, dated May 15, 2024; is hereby incorporated herein by reference in its entirety.

BACKGROUND

1. Field of the Invention

The present disclosure relates to methods of detecting mutations associated with and diagnosing CD55 deficiency, hyperactivation of complement, angiopathic thrombosis and protein losing enteropathy (CHAPLE), methods for the treatment of CHAPLE, and therapeutic compositions for treating CHAPLE.

2. Background Invention

A rare disease is generally accepted as being any disease that affects a small percentage of the population, but there is no single definition. For example, rare diseases are referred to as Orphan Diseases in the United States and defined as conditions that affect fewer than 200,000 people in the United States. Orphan diseases include, inter alia, cystic fibrosis, Lou Gehrig's disease, and Tourette's syndrome, Hamburger disease, Job syndrome, atypical hemolytic uremic syndrome, paroxysmal nocturnal hemoglobinuria, acromegaly (or "gigantism"). An accurate diagnosis of a rare disease can generally take up to 5 years because early stage symptoms could be absent, masked, misunderstood, or confused with other more prevalent diseases. New orphan diseases are discovered each year and are typically caused by inherited gene mutations.

Protein-losing enteropathy (PLE) is characterized by excessive loss of serum proteins through the gastrointestinal (GI) tract resulting in hypoproteinemia, edema, and, in some cases, pleural and pericardial effusions. Pathogenic mechanisms of PLE can involve (1) impaired barrier function of the GI mucosa, often in association with inflammatory bowel disease (IBD) and (2) impaired lymphatic drainage, either due to primary intestinal lymphangiectasia, or secondary to systemic conditions that impair lymph flow, such as cardiac diseases. Although most cases of PLE are sporadic, primary intestinal lymphangiectasia has been reported in multiple siblings of several families, suggesting a genetic etiology in certain cases.

Identifying rare monogenetic defects can elucidate the pathophysiology of disease, improve diagnosis, and promote targeted therapies for specific inherited syndromes and related common diseases. These efforts have been greatly aided by massively parallel DNA sequencing technologies, increasingly comprehensive datasets of human genetic variation, and new gene validation technologies. Several intestinal diseases related to early onset IBD (EO-IBD) have been attributed to Mendelian gene defects. Recently, a loss-of-function (LOF) mutation in the plasmalemma vesicle associated protein gene was reported in a young infant with severe PLE associated with disruption of endothelial fenestrated diaphragms in the intestinal vasculature, demonstrating that PLE may also arise from Mendelian gene defects.

The complement system is a vital part of the immune system of the body that protect against pathogens (e.g., bacteria, fungi, viruses, etc.). The complement system is a complex collection of greater than 25 plasma proteins and membrane factors. The complement components interact through a series of intricate enzymatic cleavages and membrane binding events, which result in the production of products with opsonic, immunoregulatory, and lytic functions. Because complement has potent effects on immunity and cell physiology, it must be tightly controlled.

The complement cascade includes three pathways referred to as the classical pathway, the lectin pathway, or the alternative pathway. The classical pathway of complement activation is initiated or triggered by an antibody recognizing (i.e., binding) an antigen located on a target cell. The lectin pathway of complement activation is initiated or triggered by the binding of a mannose-binding protein that is present in blood plasma to mannose-containing proteoglycans on the surfaces of bacteria and yeast, which has structural similarities to the antibody initiation of the classical pathway. As such, the lectin pathway then proceeds in a similar fashion as the classical pathway. The alternative pathway of complement activation is initiated or triggered by constituents of bacterial surfaces, as will be discussed in greater detail below.

Each of the three pathways lead to the covalent bonding of a particular fragment of a complement component (i.e., the C3b fragment of C3) to the pathogen surface, which is recognized by C3b receptors on macrophages and neutrophils. This deposition of C3b fragments on the surface of the pathogen is mediated by a C3 convertase, which is a protease that cleaves the complement component C3 to yield C3a and C3b. The C3b fragment is an osponin, which mediates interaction with phagocytes (e.g., macrophages, neutrophils, and dendritic cells, which promote inflammatory immune reactions) through their C3b receptors. As such, the opsonized pathogens are targeted by phagocytes. The opsonic function of C3b is one of the most important functions of the complement system, and its disruption leads to a susceptibility to a broad range of pathogens. C3b can then be progressively broken down by Factor I (a protease) and a cofactor (.e., Factor H, CR1, MCP, or C4BP) to iC3b, then C3c+C3dg, and finally C3d. The C3a fragment is a potent anaphylatoxin that stimulates mast cell degranulation, which results in the release of histamine from basophils and mast cells. Histamine enhances vascular permeability, smooth muscle contraction, and leukocyte activation, as well as being an attractant (chemotractic factor) for granulocytes (e.g., neutrophils, eosinophils, basophils) and macrophages.

Complement component C3, which is the most abundant complement protein and is abundantly present in plasma, is spontaneously hydrolyzed (the alternative pathway). In particular, there is a spontaneous cleavage of a thioester bond in C3 that forms C3i or C3($H_2O$). The alternative pathway is facilitated by surfaces that support the binding of activated C3 (i.e., C3i or C3($H_2O$)), as well as surfaces that have neutral or positive charge characteristics (such as those found in bacteria). The plasma protein Factor B binds to the C3i surface bound protein. Factor D then subsequently cleaves Factor B, thereby producing Ba and Bb. The Bb fragment remains bound to C3i to form a C3iBb, which is a C3 convertase that functions as described above and may be referred to as the alternative pathway C3 convertase. The alternative pathway C3 convertase is stabilized by the binding of properdin (although not required). The alternative pathway C3 convertase has an amplification affect because each of the fluid-phase C3 convertase (i.e., the alternative pathway C3 convertase) can cleave multiple C3 proteins into C3a and C3b, which results in the deposition of additional C3b covalently bound to the surface (e.g., a bacterial surface). In a similar fashion, the alternative pathway C5 convertase is formed by the addition of a second C3b monomer to the alternative pathway C3 convertase (i.e., add C3b to C3iBb, which is referred to as (C3b)$_2$Bb), which is also stabilized by the binding of properdin (although not required). The alternative pathway C3 convertase bind and cleaves C5.

The classical pathway C3 convertase is formed when complement component C1 (comprising a complex of C1q, C1r, and C1s) is activated by an antibody-target-antigen complex (e.g., a microbial antigen). That is, the binding of C1q to the antibody-target-antigen complex results in a conformational change in C1, which activates C1r. Activated C1r cleaves/activates C1s. Active C1s is a serene protease that cleaves complement component C4 into C4b and C4a and complement component C2 into C2b and C2a. C4b fragments contain a reactive thiol that readily forms amide or ester bonds with suitable molecules on a target surface (e.g., a microbial cell surface). Activated C4b and C2a form the classical pathway C3 convertase, which functions as described above. When a C3b monomer is added to the classical pathway convertase, the classical pathway C5 convertase (C4b,C2a,C3b) is formed.

As discussed above, the lectin pathway is homologous to the classical pathway with a mannose-binding lectin (MBL, which is similar to C1q) to mannose residues on the surface of a pathogen. This binding activates the MBL-associated serine proteases MASP-1 and MASP-2 (which are very similar to C1r and C1 s, respectively). This complex functions in the same fashion as C1 in the classical complement pathway.

The alternative, classical, and lectin pathway C5 convertases cleave C5, which is found in normal human serum, into C5a and C5b. Similar to C3a, C5a is a potent anaphylatoxin and chemotactic factor. C5a receptors are present on the surfaces of: bronchial and alveolar epithelial cells, bronchial smooth muscle cells, eosinophils, mast cells, monocytes, neutrophils, and activated lymphocytes.

C5b binds to C6 and C7 to form a complex that interacts with C8 and subsequently numerous C9 proteins, thereby producing a membrane attack complex (MAC) or lytic unit (C5b,6,7,8)$_1$(9)$_n$ (n=10-16 molecules) on the targeted cell membrane, which is a pore that extends through the cell membrane. When a sufficient number of MACs are present in the target cell membranes, hypotonic lysis of the targeted cell is achieved. C5a and C5b-9 also amplify the release of downstream inflammatory factors (e.g., hydrolytic enzymes, reactive oxygen species, arachidonic acid metabolites and various cytokines).

The complement system provides a robust defense against infection. However, misregulation or inappropriate activation of the complement system is associated with the pathogenesis of a variety of disorders including (e.g., rheumatoid arthritis; lupus nephritis; asthma; ischemia-reperfusion injury; atypical hemolytic uremic syndrome (aHUS); dense deposit disease; paroxysmal nocturnal hemoglobinuria (PNH); macular degeneration; hemolysis, elevated liver enzymes, and low platelets syndrome; thrombotic thrombocytopenic purpura; spontaneous fetal loss; Pauci-immune vasculitis; epidermolysis bullosa; recurrent fetal loss; multiple sclerosis; traumatic brain injury; and injury resulting from myocardial infarction, cardiopulmonary bypass and hemodialysis). Complement inhibition has been demonstrated to be effective in treating several complement-associated disorders in animal models and in humans (see, e.g., Rother et al. (2007) Nature Biotechnology 25(11):1256-1264; Wang et al. (1996) Proc Natl Acad Sci USA 93:8563-8568; Wang et al. (1995) Proc Natl Acad Sci USA 92:8955-8959; Rinder et al. (1995) J Clin Invest 96:1564-1572; Kroshus et al. (1995) Transplantation 60:1194-1202; Homeister et al. (1993) J Immunol 150:1055-1064; Weisman et al. (1990) Science 249:146-151; Amsterdam et al. (1995) Am J Physiol 268:H448-H457; and Rabinovici et al. (1992) J Immunol 149:1744 1750.

CD55 (decay accelerating factor or DAF) is a widely expressed GPI-linked cell surface protein that regulates complement activation by reducing the activity of C3 and C5 convertases and accelerating their disassembly. Specifically, DAF recognizes C4b and C3b fragments that are created during the C4 activation (classical complement pathway and lectin pathway) and C3 activation (alternate complement pathway). DAF interferes with the conversion of C2 to C2a through its interaction with the cell-associated C4b of the classical and lectin pathways. This prevents the formation of the C4b2a C3 convertase. Similarly, DAF interferes with the conversion of factor B to Bb by factor D through its interaction with C3b of the alternative pathway. This prevents the formation of the C3bBb C3 convertase of the alternative pathway. As a result, the amplification provided by 3C convertases of the complement cascade are limited by the interaction of DAF (or CD55) with C4b and C3b, which results in indirectly blocking the formation of the MAC. A rare CD55 deficiency on red blood cells (RBCs), known as the Inab phenotype, is detected by the loss of Cromer blood group antigens. This rare CD55 deficiency has been associated with complement dysregulation, formation of a strong RBC alloantibody agglutinin, and GI abnormalities. However, a disease resulting from the germline loss of CD55 has not been clearly defined to date.

As mentioned above, rare diseases are often misdiagnosed, and new rare diseases are regularly identified. For example, the present disclosure describes a newly identified rare disease—CHAPLE disease/syndrome. As such, there exists a need to accurately detect the mutations associated with CHAPLE disease/syndrome, as well as diagnose and treat individuals with CHAPLE disease/syndrome with a therapeutic composition.

SUMMARY

The present disclosure relates to the surprising and unexpected discovery of the cause of CHAPLE, and therefore, methods of diagnosing CHAPLE, as well as methods of treating patients with CHAPLE symptom(s) and methods of preventing a symptom(s) of CHAPLE in individuals predisposed to develop CHAPLE syndrome with a therapeutic composition.

In an aspect, the disclosure provides a method of diagnosing a patient with CD55 deficiency, hyperactivation of complement, angiopathic thrombosis and protein losing enteropathy (CHAPLE). The method comprises: providing a sample from a patient; performing an assay to detect at least one of: at least one mutation in a DNA sequence of a CD55 gene, at least one mutation in a RNA sequence (or mRNA sequence) of a CD55 transcript, at least one mutation in a DNA sequence of a CD55 complementary DNA (cDNA), decay-accelerating factor (DAF) or CD55 protein, complement deposition, or a combination thereof, and diagnosing the patient with CHAPLE.

In an embodiment, the patient is diagnosed with CHAPLE when at least one of the following is detected: (i) at least one mutation in a DNA sequence, an RNA sequence or a cDNA sequence of CD55 that results in a CD55 protein with substantially diminished functional activity, a CD55 protein with no functional activity, a lack of expression of CD55 protein (i.e., no CD55 protein expression), or a substantially diminished expression of CD55 protein; (ii) a CD55 protein with substantially diminished functional activity; (iii) a CD55 protein with no functional activity; (iv) a lack of expression of CD55 protein (i.e., no CD55 protein expression); (v) a substantially diminished expression of CD55 protein; or (vi) a combination thereof.

In another embodiment, the patient is diagnosed with CHAPLE when the patient has at least one CHAPLE related symptom and at least one of the following is detected: (i) at least one mutation in a DNA sequence, an RNA sequence or a cDNA sequence of CD55 that results in a CD55 protein with substantially diminished functional activity, a CD55 protein with no functional activity, a lack of expression of CD55 protein (i.e., no CD55 protein expression), or a substantially diminished expression of CD55 protein; (ii) a CD55 protein with substantially diminished functional activity; (iii) a CD55 protein with no functional activity; (iv) a lack of expression of CD55 protein (i.e., no CD55 protein expression); (v) a substantially diminished expression of CD55 protein; or (vi) a combination thereof.

In some embodiments, the CHAPLE related symptom is selected from the group consisting of: inflammatory bowel disease, enteropathy, protein losing enteropathy, protein losing enteropathy associated with hypoalbuminemia, hypoalbuminemia, hypogammaglobulinemia, intestinal lymphangiectasia, lymphangiectasia, thrombotic events, thromboembolism, hyperactivation of complement, angiopathic thrombosis, hypoproteinemia, or a combination thereof.

In other embodiments, the CHAPLE related symptom is selected from the group consisting of inflammatory bowel disease, protein losing enteropathy associated with hypoalbuminemia, hypogammaglobulinemia, intestinal lymphangiectasia, thrombotic events or a combination thereof. For example, in certain embodiments, the patient has at least 3 of the following symptoms: inflammatory bowel disease, protein losing enteropathy associated with hypoalbuminemia, hypogammaglobulinemia, intestinal lymphangiectasia, or thrombotic events.

In a particular embodiment, the method further comprises administering an effective mount of a composition comprising at least one complement inhibitor to the subject with CHAPLE, wherein the composition is effective in treating or preventing at least one symptom of CHAPLE.

In a further embodiment, the complement inhibitor is selected from the group consisting of a serine protease inhibitor, a soluble complement regulator, a therapeutic antibody or an antigen-binding fragment thereof, a complement component inhibitor, and an anaphylatoxin receptor antagonist.

In certain embodiments, the mutation in the DNA sequence of the CD55 gene or in the RNA sequence of the CD55 transcript results in a near to complete absence of CD55 protein expression or the expression of CD55 protein with substantially diminished function or that is non-functional.

In an embodiment, the mutation in the DNA sequence of the CD55 gene is at least one of c.149-150delAA, c.149-150insCCTT, c.109delC, c.800G>C, c.287-1G>C, c.149-150delAAinsCCTT or a combination thereof.

In further embodiments, detecting includes at least one of: (i) sequencing at least a portion of the CD55 gene or the CD55 transcript or the CD55 cDNA; or (ii) contacting a labeled nucleic acid probe to at least a portion of the CD55 gene or the CD55 transcript or the CD55 cDNA; or (iii) contacting at least a portion of the CD55 gene or CD55 transcripts or the CD55 cDNA with a microarray; or (iv) a combination thereof.

In a particular embodiment, hybridization of the labeled nucleic acid probe is indicative of a mutation in the portion of the CD55 gene or the CD55 transcript or the CD55 cDNA. In another particular embodiment, hybridization of the labeled nucleic acid probe is indicative of the portion of the CD55 gene or the CD55 transcript or the CD55 cDNA having a wild-type sequence at the location of hybridization.

In certain other embodiments, sequencing at least a portion of the CD55 gene or CD55 transcript or CD55 cDNA thereof includes amplifying at least one region of interest for sequencing with at least one polymerase chain reaction (PCR) that includes at least one of the following primer sets: (i) CTACTCCACCCGTCTTGTTTGT (SEQ ID NO.4) and TTTGGGGGTTAAGGATACAGTC (SEQ ID NO.5) (Exon 1); (ii) CAGGTGTGGCATTTCAAGG (SEQ ID NO.6) and ACCCTGGGGTTTAGTAACGC (SEQ ID NO.7) (Exon 2); (iii) AAGTACTAAATATGCGCAAAGCAG (SEQ ID NO.8) and ATGGTCCTATCAAGAAACATCC (SEQ ID NO.9) (Exon 3); (iv) GTTACCTTCTTTGTGTGTATGCC (SEQ ID NO.10) and GCTGTGAATACCAGTCATGAAAC (SEQ ID NO.11) (Exon 4); (v) AACCTGGAGAATTTGAGGAAAG (SEQ ID NO.12) and TGTGCTAATATTCTTAAGGGGC (SEQ ID NO.13) (Exon 5); (vi) GCATTTATAAGCATCTCTTGTTGG (SEQ ID NO.14) and TCATTGAATGTCTGCAACCC (SEQ ID NO.15) (Exon 6); (vii) CTAGGTGTTTGTGGGGAGAGAG (SEQ ID NO.16) and TCTGGTGGGTTTCTGAAGAGTT (SEQ ID NO.17) (Exon 7); (viii) TTTACGCAGAGTCCTTCAGC (SEQ ID NO.18) and CCATTTAATCCTGCAATCTTGG (SEQ ID NO.19) (Exon 8); (ix) TGGAAATTTGAGTTGCTTTCG (SEQ ID NO.20) and TCTCCCAGGAATATGGATTG (SEQ ID NO.21) (Exon 9); (x) GCACCCCAAATTAACTGATTC (SEQ ID NO.22) and ATGTGATTCCAGGACTGCC (SEQ ID NO.23) (Exon 10); or (xi) a combination thereof.

In yet another embodiment, contacting a labeled nucleic acid probe to at least a portion of the CD55 gene or the CD55 transcript or the CD55 cDNA is performed using real-time PCR. In an embodiment, hybridization of a real-time PCR probe is indicative of a mutation in the portion of the CD55 gene or CD55 transcript or the CD55 cDNA. In another embodiment, hybridization of a real-time PCR probe is indicative of the portion of the CD55 gene or CD55 transcript or the CD55 cDNA having a wild-type sequence (or not having a CHAPLE related mutations) at the location of hybridization.

In some embodiments, contacting a labeled nucleic acid probe to at least a portion of the CD55 cDNA comprises: isolating CD55 transcripts; reverse transcribing at least a portion of the CD55 transcripts; and contacting the cDNA with the labeled nucleic acid probe.

In further embodiments, the microarray includes probes (e.g., immobilized probes) designed to detect DNA, transcripts (i.e., RNA or mRNA), or cDNA mutations that result in the complete absence in CD55 protein or a CD55 protein with substantially diminished function or that is virtually non-functional.

In certain embodiments, detecting CD55 protein comprises: contacting the sample with at least one CD55 binding polypeptide. The CD55 binding polypeptides can include a detectable label. Furthermore, the binding polypeptide can be an anti-CD55 antibody or a CD55-binding fragment thereof.

In other embodiments, detecting CD55 protein further comprises contacting the sample or a CD55-CD55 binding polypeptide complex with at least one secondary polypeptide that binds specifically to the CD55 binding polypeptide. The secondary polypeptide can include a detectable label. The secondary polypeptide can be an antibody or fragment thereof that binds the CD55 binding polypeptide.

In an embodiment, detecting CD55 protein is performed using at least one of the following assays: western blot, flow cytometry, an immunoassay or a combination thereof. For example, the immunoassay can be at least one assay selected from the group consisting of flow cytometry, enzyme-linked immunosorbent assay (ELISA), radioimmunoassay, magnetic immunoassay, enzyme-linked immunospot (ELISPOT), and immunofluorescence.

In another embodiment, the detecting of CD55 binding function includes examining at least one of C3b affinity, C3b avidity, C4b affinity, C4b avidity or a combination thereof.

In a particular embodiment, detecting complement deposition includes detecting C3d deposition. In an embodiment, detecting complement deposition is determined by flow cytometry.

In a further aspect, the disclosure provides a method of treating a patient having CD55 deficiency, hyperactivation of complement, angiopathic thrombosis and protein losing enteropathy (CHAPLE) or preventing CHAPLE in a patient at risk of developing the same. The method comprises administering an effective amount of a composition comprising at least one complement inhibitor to a subject in need thereof. The composition is effective in treating and/or preventing at least one symptom of CHAPLE.

In some embodiments, the complement inhibitor is selected from the group consisting of a serine protease inhibitor, a soluble complement regulator, a therapeutic antibody or an antigen-binding fragment thereof, a complement component inhibitor, and an anaphylatoxin receptor antagonist.

In certain embodiments, the serine protease inhibitors is at least one of a C3 convertase inhibitor, a C5 convertase inhibitor, a C1 inhibitor, a C1r inhibitor, a C1s inhibitor, a C2a inhibitor, a MASP-1 inhibitor, a MASP-2 inhibitor, a factor D inhibitor, a factor B inhibitor, a factor I inhibitor or a combination thereof. For example, the serine protease inhibitor can be at least one of BCX-1470 (BioCryst, Birmingham, AL, USA), C1s-INH-248 (Knoll/Abbott, Abbott Park, IL, USA), compstatin, Cetor® (Sanquin, Amsterdam, Netherlands), Berinert® (CSL Behring, King of Prussia, PA, USA), Cinryze™ (ViroPharma, Exton, PA, USA), rhC1INH (Pharming Group N.V., Leiden, Netherlands), Ruconest® (Salix Pharmaceuticals, Inc., Raleigh, NC, USA) or a combination thereof.

In other embodiments, the soluble complement regulator is at least one of a soluble form of a membrane cofactor protein (MCP or CD46), a soluble form of a decay-accelerating factor (DAF or CD55), a soluble form of a membrane attack complex-inhibitor protein (MAC-IP or CD59), a soluble form of complement receptor 1 (CD35) or a combination thereof. For example, the soluble complement regulator can be at least one of sCR1 (TP10; Advant Immunotherapeutics, Needham, MA, USA), sCR1-sL$^{ex}$ (TP10; Advant Immunotherapeutics, Needham, MA, USA), sDAG-sMCP hybrid (MLN-2222, Millennium, Cambridge, MA, USA), a membrane-tethered sCD59 (Mirococept or APT070; Inflazyme Pharmaceuticals, Vancouver, British Columbia, Canada) or a combination thereof.

In further embodiments, the therapeutic antibody or the antigen-binding fragment thereof is at least one polypeptide that binds C3, C3a, C3b, C3 convertase, C5, C5a, C5b, C5 convertase, C7, C8, or C9, factor B, factor D, C4, C2, C1, properdin, a functional blocking antibody of an anaphylatoxin or a combination thereof. The binding can inhibit complement activation by at least one of blocking association/binding with other complement proteins, blocking association/binding with receptor proteins, blocking serine protease activity or a combination thereof. For example, the therapeutic antibody or the antigen-binding fragment thereof can be at least one of eculizumab (Soliris®; Alexion Pharmaceuticals Inc., New Haven, CT, USA), ALXN1007 (Alexion Pharmaceuticals Inc., New Haven, CT, USA), neutrazumab (G2 Therapies, Darlinghurst, NSW, Australia), Pexelizumab (Alexion Pharmaceuticals Inc., New Haven, CT, USA), ofatumumab (Genmab A/S, Copenhagen, Denmark), HuMax-CD38 (Benmab A/S, Copenhagen, Denmark), TNX-558 (Tanox, South San Francisco, CA, USA), TNX-234 (Tanox, South San Francisco, CA, USA), TA106 (Taligen, Aurora, CO, USA), anti-properdin (Novelmed, Cleveland, OH, USA) or a combination thereof.

In yet other embodiments, the complement component inhibitor (e.g., a small molecule) is a peptide, nucleic acids, a synthetic molecule or a combination thereof that disrupts protein functions by steric hindrance or the induction of conformational changes. For example, the complement component inhibitor can be at least one of compstatin, anti-C5 RNA aptamer (ARC1905; Archemix, Cambridge, MA, USA), or analogs or derivatives thereof, or a combination thereof.

In another embodiment, the anaphylatoxin receptor antagonist is at least one of a C5aR antagonist, a C5L2 antagonist, a C3a receptor antagonist, a functional blocking antibody of an anaphylatoxin or a combination thereof. For example, the anaphylatoxin receptor antagonist is at least one of PMX-53 (PepTech Corp, Bedform, MA, USA), PMX-205 (PepTech Corp, Bedform, MA, USA), JPE-1375 (Jerini, Berlin, Germany), JSM-7717 (Jerini, Berlin, Germany), rhMBL (Enzon Pharmaceuticals, Cranford, NJ, USA), NTD 9513727 (Tocris Bioscience, Bristol, United Kingdom) or a combination thereof.

In another aspect, the disclosure provides a composition for treating or preventing at least one symptom of CD55 deficiency, hyperactivation of complement, angiopathic thrombosis and protein losing enteropathy (CHAPLE) in a subject in need thereof. The therapeutic composition comprises an effective amount of two or more agents and a pharmaceutically acceptable carrier, wherein at least one of the agents is a complement inhibitor, wherein the composition is effective in treating or preventing at least one symptom of CHAPLE. In an embodiment, at least two of the agents are a complement inhibitor. In another embodiment the effective amount is a synergistically effective amount of the agents.

In an additional embodiment, the complement inhibitor is selected from the group consisting of a serine protease inhibitor, a soluble complement regulator, a therapeutic antibody or an antigen-binding fragment thereof, a complement component inhibitor (e.g., a small molecule), and an anaphylatoxin receptor antagonist.

In further embodiments, the complement inhibitors include a C3 convertase inhibitor and a C5 convertase inhibitor. In another embodiment, the complement inhibitors includes: a soluble form of CD55; and at least one of a C3 convertase inhibitor, a C5 convertase inhibitor or a combination thereof.

In certain embodiments, the serine protease inhibitors is at least one of a C3 convertase inhibitor, a C5 convertase inhibitor, a C1 inhibitor, a C1r inhibitor, a C1s inhibitor, a C2a inhibitor, a MASP-1 inhibitor, a MASP-2 inhibitor, a factor D inhibitor, a factor B inhibitor, a factor I inhibitor or a combination thereof.

In a particular embodiment, the serine protease inhibitor is at least one of BCX-1470 (BioCryst, Birmingham, AL, USA), C1s-INH-248 (Knoll/Abbott, Abbott Park, IL, USA), compstatin, Cetor® (Sanquin, Amsterdam, Netherlands), Berinert® (CSL Behring, King of Prussia, PA, USA), Cinryze™ (ViroPharma, Exton, PA, USA), rhC1INH (Pharming Group N.V., Leiden, Netherlands), Ruconest® (Salix Pharmaceuticals, Inc., Raleigh, NC, USA) or a combination thereof.

In other embodiments, the soluble complement regulator is at least one of a soluble form of a membrane cofactor protein (MCP or CD46), a soluble form of a decay-accelerating factor (DAF or CD55), a soluble form of a membrane attack complex-inhibitor protein (MAC-IP or CD59), a soluble form of complement receptor 1 (CD35) or a combination thereof.

In an embodiment, the soluble complement regulator is at least one of sCR1 (TP10; Advant Immunotherapeutics, Needham, MA, USA), sCR1-sL$^{ex}$ (TP10; Advant Immunotherapeutics, Needham, MA, USA), sDAG-sMCP hybrid (MLN-2222, Millennium, Cambridge, MA, USA), a membrane-tethered sCD59 (Mirococept or APT070; Inflazyme Pharmaceuticals, Vancouver, British Columbia, Canada) or a combination thereof.

In other embodiments, the therapeutic antibody or the antigen-binding fragment thereof is at least one polypeptide that binds C3, C3a, C3b, C3 convertase, C5, C5a, C5b, C5 convertase, C7, C8, or C9, factor B, factor D, C4, C2, C1, properdin, a functional blocking antibody of an anaphylatoxin or a combination thereof, wherein said binding inhibits complement activation by, e.g., at least one of blocking association/binding with other complement proteins, blocking association/binding with receptor proteins, blocking serine protease activity or a combination thereof.

In certain embodiments, the therapeutic antibody or the antigen-binding fragment thereof is at least one of eculizumab (Soliris®; Alexion Pharmaceuticals Inc., New Haven, CT, USA), ALXN1007 (Alexion Pharmaceuticals Inc., New Haven, CT, USA), neutrazumab (G2 Therapies, Darlinghurst, NSW, Australia), Pexelizumab (Alexion Pharmaceuticals Inc., New Haven, CT, USA), ofatumumab (Genmab A/S, Copenhagen, Denmark), HuMax-CD38 (Benmab A/S, Copenhagen, Denmark), TNX-558 (Tanox, South San Francisco, CA, USA), TNX-234 (Tanox, South San Francisco, CA, USA), TA106 (Taligen, Aurora, CO, USA), anti-properdin (Novelmed, Cleveland, OH, USA) or a combination thereof.

In yet other embodiments, the complement component inhibitor is a peptide, nucleic acids, a synthetic molecule or a combination thereof that disrupts protein functions by steric hindrance or the induction of conformational changes.

In a particular embodiment, the complement component inhibitor is at least one of compstatin, anti-C5 RNA aptamer (ARC1905; Archemix, Cambridge, MA, USA), or analogs or derivatives thereof, or a combination thereof.

In additional embodiments, the anaphylatoxin receptor antagonist is at least one of a C5aR antagonist, a C5L2 antagonist, a C3a receptor antagonist, a functional blocking antibody of an anaphylatoxin or a combination thereof.

In certain embodiments, the anaphylatoxin receptor antagonist is at least one of PMX-53 (PepTech Corp, Bedform, MA, USA), PMX-205 (PepTech Corp, Bedform, MA, USA), JPE-1375 (Jerini, Berlin, Germany), JSM-7717 (Jerini, Berlin, Germany), rhMBL (Enzon Pharmaceuticals, Cranford, NJ, USA) or a combination thereof.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

FIGS. 2A, 2B, 2C, and 2D. Nucleotide and amino acid alignments for c.149_150delAAinsCCTT (A), c.109delG (B), c.287-1G>A (C), c.800G>C (D) to wild-type CD55 sequences (CD55 genomic reference sequence NG_007465.1, SEQ ID NO: 1, CD55 mRNA reference sequence transcript NM_000574.4, SEQ ID NO: 2; and CD55 protein reference sequence NP_000565.1, SEQ ID NO: 3).

FIG. 4. Show Table 2, which shows clinical and immunological characteristics of patients with CD 55 deficiency. Symptoms present at first clinical presentation are indicated by red text.‡ The patient received colchicine for the treatment of suspected Familial Mediterranean fever (FMF). Numbers in boldface indicate values below the normal range. N/A: Not applicable (P4.2 and P4.3 were not evaluated by endoscopy). IVC: Inferior vena cava.

FIGS. 9A, 9B, 9C, 9D, 9E, 9F, 9G, 9H, 9I, 9J, 9K, 9L, 9M, 9N, 90, and 9P. Changes in inflammatory cytokine production by CD55 deficient cells promote pro-thrombotic changes in endothelial cells. Cytokine secretion in control and patient T cells following restimulation with anti-CD3 for 48 hours. Cells were either left untreated or treated with a combination of C3aR and C5aR1 inhibitors, both at 10 μM final concentration. Each patient point represents the average of at least three independent experiments. Results are for TNFα, IL10, or IFNγ (A, B, and C respectively). Anaphylatoxin receptor surface expression on proliferating $CD4^+$ T cells grown in complete RPMI supplemented with 100 u/mL IL2, isotype: filled grey line, sample: solid black line (D). C3aR expression on proliferating $CD4^+$ T cells grown in serum free X-vivo15 media supplemented with 100 u/mL IL-2 w/wo 10 nM ATRA, grey and black line respectively, isotype: filled grey line (E). IL-10 production in control and patient T cells stimulated with anti-CD3 and stimulatory antibodies directed against the indicated costimulatory molecules (F). Flow plots of thrombomodulin (TM) and Tissue Factor (TF) expression on HUVECs cultured for 24 hours w/wo 10 ng/mL TNFα (G). Quantification of the change in TM and TF expression on HUVECs in response to 24 hour culture with increasing doses of TNFα (H). Flow plots of CD46 and CD59 expression on HUVECs cultured for 24 hours w/wo 10 ng/mL TNFα (I). Quantification of CD46, CD59, and CD55 expression on HUVECs in response to 24 hour culture with increasing doses of TNFα (J, K, and L, respectively). Quantification of the change in TM and TF expression on HUVECs in response to 48 hour culture with increasing doses of ATRA (M). Quantification of CD46, CD59, and CD55 expression on HUVECs in response to 48 hour culture with increasing doses of ATRA (N, O, and P, respectively). (not significant (n.s.), * $p<0.05$,  $p<0.01$, * $p<0.001$).

FIGS. 10A, 10B, 10C, 10D, 10E, 10F, 10G, 10H, and 10I. Primary T cell stimulation, gut homing phenotype induction by ATRA, and CD55 mediated costimulation of T cell activation. Time course of TNFα secretion upon stimulation of Naïve human $CD4^+$ T cells in serum free media for P1, P2, and P4-P6 (A). Time course of IL-10 secretion upon stimulation of Naïve $CD4^+$ T cells in serum free media for P1, P2, and P4-P6 (B). Time course of IFNγ secretion upon stimulation of Naïve $CD4^+$ T cells in serum free media for P1, P2, and P4-P6 (C). Surface expression of the gut-homing integrin α4β7 in human T cells grown in serum free conditions w/wo supplementation with 10 nM ATRA (D). Surface expression of the gut-homing chemokine receptor CCR9 in Naïve human $CD4^+$ T cells grown in serum free conditions w/wo supplementation with 10 nM ATRA (E). CD69 expression after stimulation of control and patient T cells with the indicated dose of anti-CD3 antibody w/wo costimulation with anti-CD55 (F). Percent of Control and patient T cells that upregulated CD25 and CD69 expression after stimulation anti-CD3 antibody w/wo costimulation with anti-CD28 or anti-CD55 (G). CFSE dilution in control or patient T cells stimulation with 10 μg/mL anti-CD3 and the indicated co-stimulatory molecules (H). IL10 secretion of control and patient cells in response to varying stimuli (I).

Figure 11A:
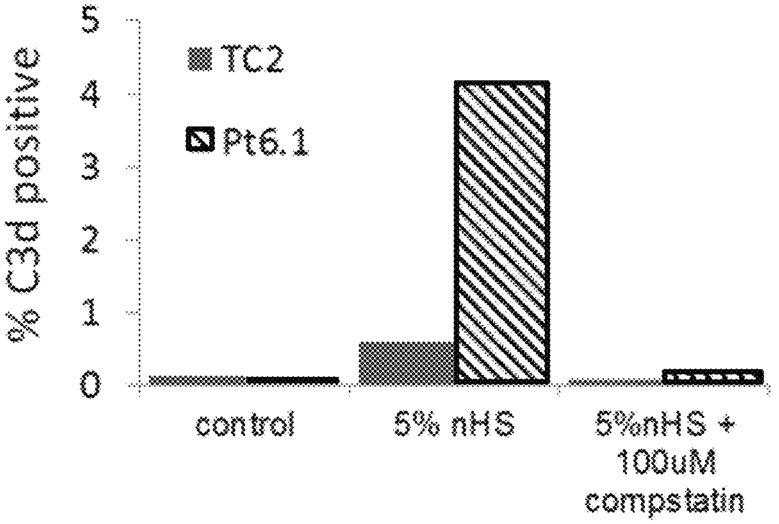
Figure 11B:
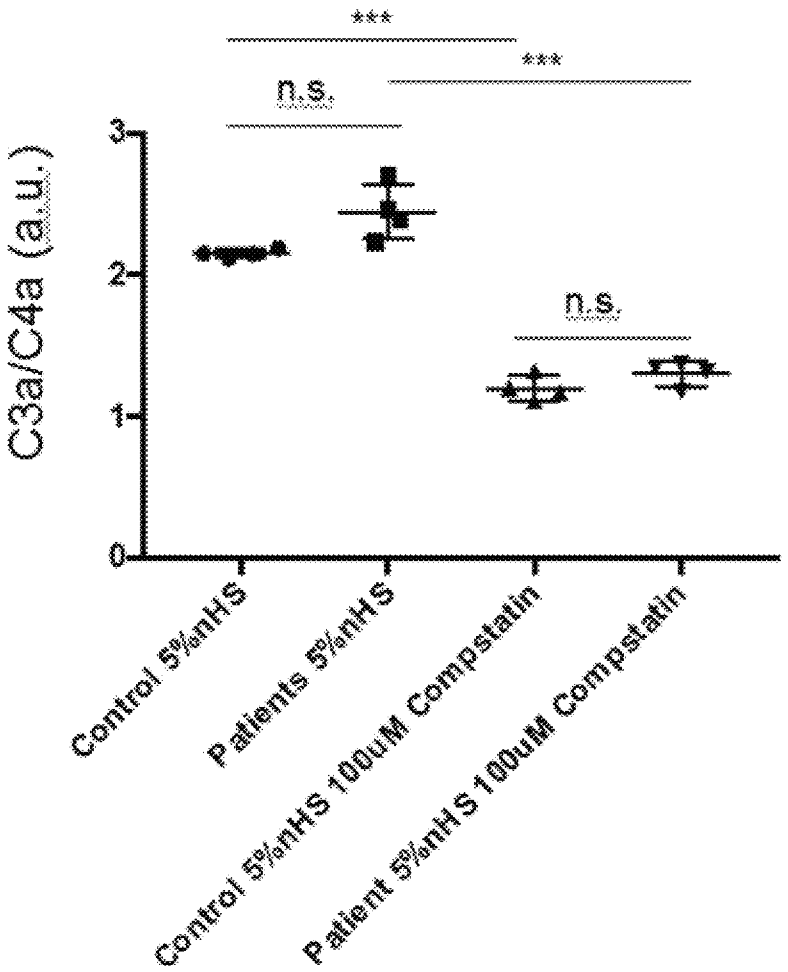
Figure 11C:
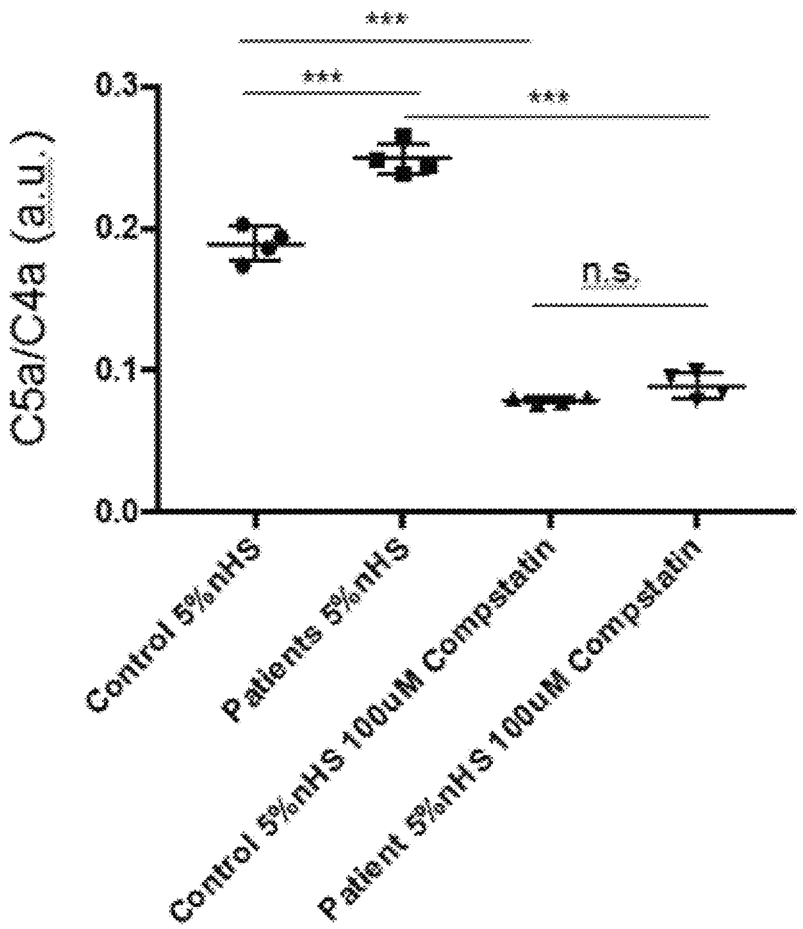

FIGS. 11A, 11B, and 11C. (A) C3d deposition on patient and control T cells were incubated in the presence or absence of 5% nHS with or without the addition of 100 μM Compstatin to block complement activation. (B) Ratio of C3a to C4a in culture supernatants after 24 hours of incubation with 5% nHS w/wo 100 μM compstatin. (C) Ratio of C5a to C4a in culture supernatants after 24 hours of incubation with 5% nHS or without 100 μM compstatin. ***= $p<0.001$.

Figure 12A:
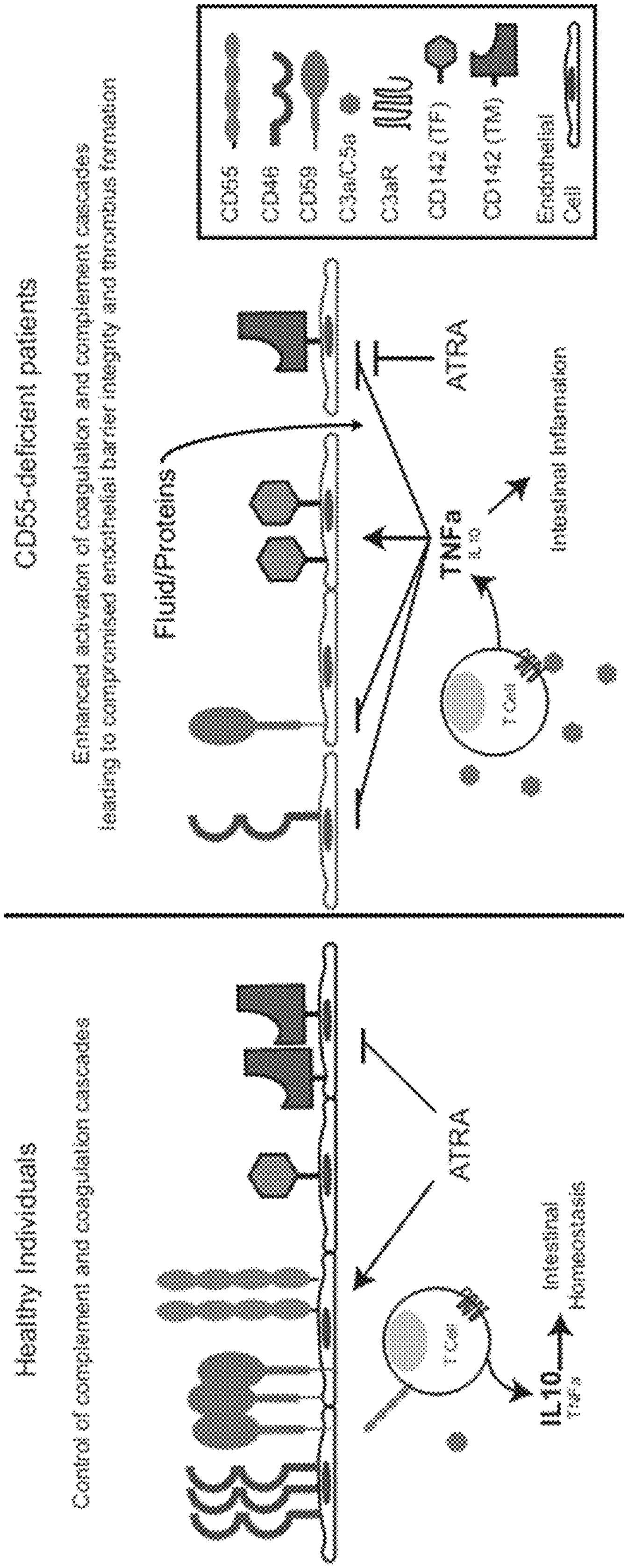
Figure 12B:
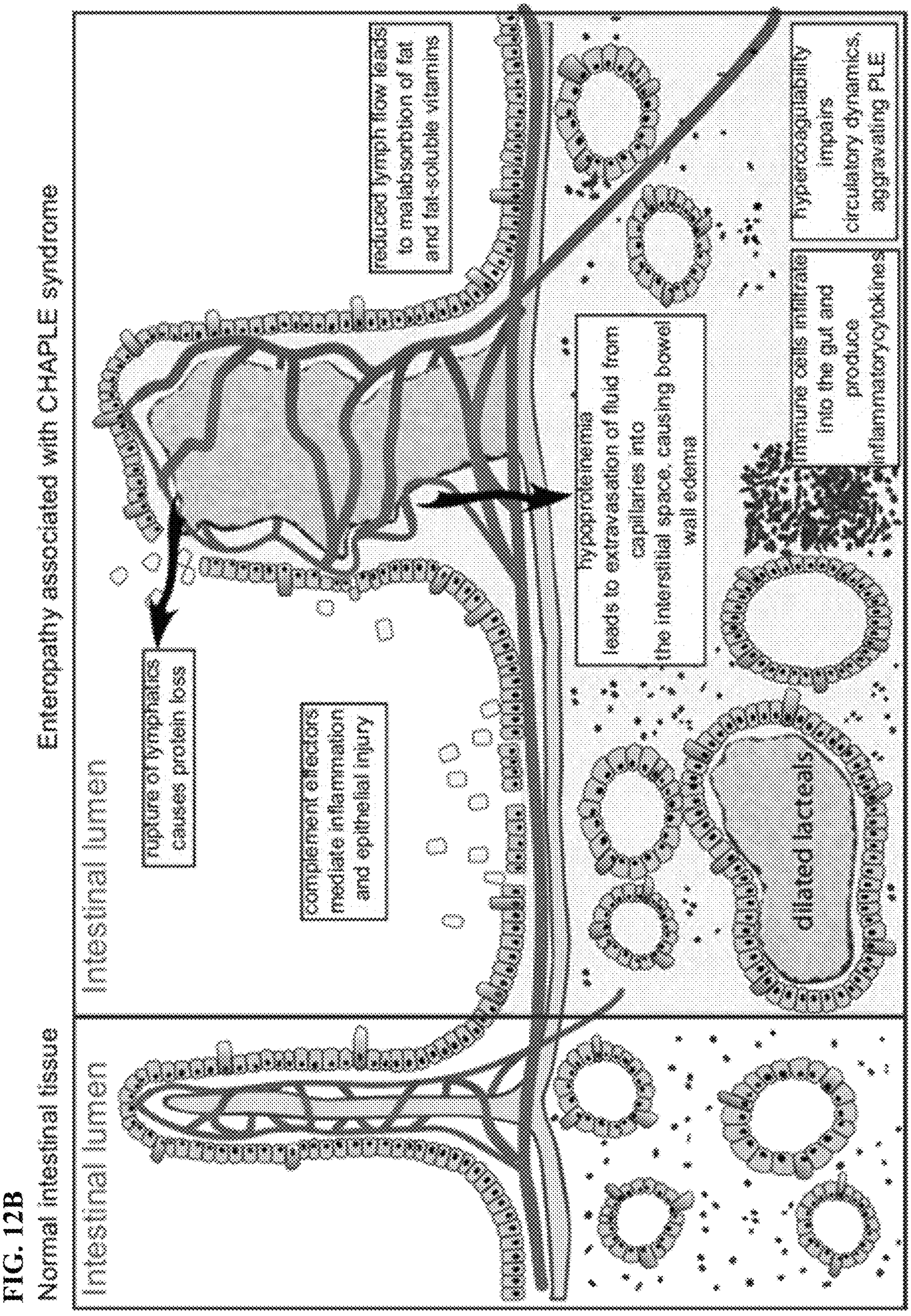

FIGS. 12A and 12B. Model of CHAPLE syndrome molecular pathogenesis leading to PLE. In healthy individuals CD55 prevents complement activation and generation of anaphylatoxins. T cells produce an inflammatory cytokine mileu that is balanced towards production of IL10 and control of intestinal immune responses. CD55 further protects from complement activation on other host cells, including prevention of complement activation on endothelial cells. CD55 deficiency associated with CHAPLE syndrome results in increased complement activation and anaphylatoxin production. The lack of CD55 and signaling by anaphylatoxins produces an inflammatory environment characterized by low IL-10 production and increased TNFα production. Lower IL-10 production likely allows for further immunological activation, while TNFα drives an inflammatory environment and endothelial cell changes characterized by the down regulation of complement regulatory proteins CD46 and CD59 and skewing of tissue factor and thrombomodulin expression towards a procoagulative state. Lack of CD55 on endothelial cells further exasperates the changes caused by TNFα production leading to uncontrolled activation of the coagulation and complement cascades on endothelial surfaces. This directly leads to endothelial barrier damage and protein/fluid loss into interstitial spaces. The presence of high concentrations of retinoic acid in intestinal tissues drives the upregulation of CD55 and down regulation of thrombomodulin, likely accounting for the predisposition to intestinal manifestations in CHAPLE syndrome (A). Proinflammatory and procoagulant changes described in A, and various pathological processes driven by excessive complement effectors generated by immune response to the gut-microbiome lead to lymph vessel distortion and compromised lymphatic flow. Ensuing lymphangiectasia results in GI protein loss and malabsorption of fat and micronutrients. Aggravation of the mucosal edema due to hypoproteinemia and the pathological inflammation drives worsening enteropathy. Intraluminal complement activation likely impacts intestinal epithelial function. This, combined with hypercoagulability within blood vessels impairs circulatory dynamics thus aggravating the PLE (B).

DETAILED DESCRIPTION

As described herein, individuals with a CD55 gene mutation are afflicted with CD55 deficiency, hyperactivation of complement, angiopathic thrombosis and protein losing enteropathy (CHAPLE), which includes debilitating symptoms such as inflammatory bowel disease, protein losing enteropathy (which can be associated with hypoalbuminemia), hypogammaglobulinemia, intestinal lymphangiectasia, and/or thrombotic events.

The present disclosure is related, in part, to the surprising and unexpected discovery individuals afflicted with the above symptoms have a CD55 deficiency due to at least one CD55 gene mutations that results in the near to complete lack of expression of CD55 protein and/or the expression of a CD55 protein that has substantially diminished functional activity or that is devoid of functional activity.

Unless otherwise defined, all technical and scientific terms used herein have the same meaning as commonly understood by one of ordinary skill in the art to which this disclosure belongs. All publications, patent applications, patents, and other references mentioned herein are incorporated by reference in their entireties. In the case of conflict, the present specification, including definitions, will control. In addition, the examples are illustrative only and not intended to be limiting.

Where a range of values is provided, it is understood that each intervening value, to the tenth of the unit of the lower limit unless the context clearly dictates otherwise (such as in the case of a group containing a number of amino acids in which case each amino acid number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The phrases "pharmaceutically or pharmacologically acceptable" refer to molecular entities and compositions that do not preclude use in a human or animal.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "polypeptide" encompasses two or more naturally occurring or synthetic amino acids linked by a covalent bond (e.g., an amide bond). Polypeptides as described herein include full length proteins (e.g., fully processed proteins such as antibodies) as well as shorter amino acids sequences (e.g., fragments of naturally occurring proteins or synthetic polypeptide fragments such as antigen-binding fragments of antibodies).

The term "patient" or "subject" is used throughout the specification to describe an animal, preferably a human or a domesticated animal, to whom treatment, including prophylactic treatment, with the compositions according to the present disclosure is provided. For treatment of those conditions or disease states which are specific for a specific animal such as a human patient, the term patient refers to that specific animal. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

The term "inflammatory bowel disease" refers to

The term "lymphangiectasia" refers to a pathologic dilation of lymph nodes, which causes a disease known as "intestinal lymphagiectasia."

The term "intestinal lymphangiectasia" refers to a disease characterized by lymphatic vessel dilation, chronic diarrhea, and loss of proteins, such as serum albumin and globulin. Considered to be the cause of a chronic form of protein-losing enteropathy.

The term "enteropathy" refers to any pathology of the intestine.

The term "protein losing enteropathy" (PLE) refers to any condition of the gastrointestinal tract (e.g., damage to the gut wall) that results in a net loss of protein from the body. Symptoms include, e.g., diarrhea, fever, general abdominal discomfort, hypoproteinemia, and/or edema. See, also, the discussion of PLE above.

The term "thrombosis" refers to the formation of a blood clot inside a blood vessel, thereby obstructing blood flow through the circulatory system.

The term "thrombotic events" refers to the formation of a blood clot inside a blood vessel, thereby obstructing blood flow through the circulatory system The term "thromboembolism" refers to the obstruction of a blood vessel by a blood clot that has become dislodged from another site in the circulatory system.

The term "hypoproteinemia" refers to a condition in which there is an abnormally low level of protein in the blood and is often accompanied with edema.

The term "angiopathic thrombosis" (or microangiopathic hemolytic anemia) refers to the pathology that relates from thrombosis in small blood vessels (such as capillaries and arterioles). The thrombosis is usually a consequence of endothelial cell injury, which results in fibrin exudation, fibrinoid necrosis, platelet aggregation, and thus, the thrombosis of small blood vessels The term "hypogammaglobulinemia" refers to a type of hypoproteinemia, in which the level of gamma globulins is abnormally low, which results in primary immune deficiency disease.

The term "hypoalbuminemia" refers to a type of hypoproteinemia in which the level of albumin in the blood is abnormally low.

The term "hyperactivation of complement" refers to a medical sign in which the complement pathway is overly active.

The term "disease" refers to any condition that impairs the normal functioning of the body. As such, diseases are associated with dysfunctioning of the body's normal homeostatic processes.

The term "syndrome" refers to the association of several medical signs, symptoms, and/or other characteristics that often occur together, which may have a single or a multifactorial cause.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments" (i.e., an antigen-binding fragment of an antibody), as defined for the purpose of the present disclosure, comprise a portion of an intact antibody, generally including the antigen binding or variable region of the intact antibody and optionally the Fc region of an antibody. Examples of antibody fragments include linear antibodies, single-chain antibody molecules (e.g., scFv), $F(ab')_2$ fragments, Fab' fragments, and multi-specific antibodies formed from antibody fragments. The antibody fragments may retain at least part of the hinge and optionally the $C_H1$ region of an IgG heavy chain. The antibody fragments may retain the entire constant region of an IgG heavy chain, and include an IgG light chain.

The term "Fc region" is used to define a C-terminal region of an immunoglobulin heavy chain. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin generally comprises two constant domains, $C_H2$ and $C_H3$.

The term "F(ab) fragment" is defined as a fragment of an immunoglobulin molecule that comprises the variable regions of a light chain and a heavy chain. That is, a Fab fragment is a monovalent antigen binding structure of an immunoglobulin without the Fc portion, and which results from the treatment of an immunoglobulin with papain.

The term "F(ab)' fragment" is defined as a fragment of an immunoglobulin molecule that comprises the variable regions of a light chain and a heavy chain. That is, the fragment is monovalent and most of the Fc portion is removed, which can be achieved through the treatment of an immunoglobulin molecule with pepsin and β-mercaptoethanol.

The term "$F(ab')_2$ fragment" is defined as a fragment of an immunoglobulin molecule that comprises two F(ab) fragments and a portion of the hinge region. That is, most of the Fc portion is removed, which can be achieved through the treatment of an immunoglobulin molecule with pepsin.

The term "single-chain variable fragments" (scFvs) is defined as a polypeptide engineered to comprise the variable regions (i.e., the antigen-binding domains) of a light immunoglobulin chain and a heavy immunoglobulin chain. The light chain and heavy chain can be joined by a flexible linker sequence.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler and Milstein 1975 *Nature* 256:495, or may be made by recombinant DNA methods. The "monoclonal antibodies" may also be isolated from phage antibody libraries.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The term "hypervariable region" when used herein refers to the amino acid residues of an antibody that are responsible for antigen-binding. The hypervariable region comprises amino acid residues from a "complementarity determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain). "Framework" or "FR" residues are those variable domain residues other than the hypervariable region residues as herein defined.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptides will be prepared by at least one purification step.

In an aspect, the disclosure provides a method of diagnosing a patient or subject with CD55 deficiency, hyperactivation of complement, angiopathic thrombosis and protein losing enteropathy (CHAPLE). The method comprises: providing a sample from a patient; performing an assay to detect at least one of: at least one mutation in a DNA sequence of a CD55 gene, at least one mutation in a RNA sequence of a CD55 transcript as compared to wild-type, at least one mutation in a DNA sequence of a CD55 complementary DNA (cDNA), decay-accelerating factor (DAF) or CD55 protein, complement deposition, or a combination thereof; and diagnosing the patient with CHAPLE. In an embodiment, the mutations in the DNA sequence of the CD55 gene or cDNA or the mutation in the RNA sequence of the CD55 RNA/transcript results in diminished CD55 protein expression (e.g., substantially diminished or devoice of CD55 expression) or diminished or non-functional CD55 protein function (e.g., a CD55 that has diminished or that is incapable of binding C3b and/or C4b).

In an embodiment, the patient is diagnosed with CHAPLE when at least one of the following is detected: (i) at least one mutation in a DNA sequence, an RNA sequence or a cDNA sequence of CD55 that results in a CD55 protein with substantially diminished functional activity, a CD55 protein with no functional activity, a lack of expression of CD55 protein (i.e., no CD55 protein expression), or a substantially diminished expression of CD55 protein; (ii) a CD55 protein with substantially diminished functional activity; (iii) a CD55 protein with no functional activity; (iv) a lack of expression of CD55 protein (i.e., no CD55 protein expression); (v) a substantially diminished expression of CD55 protein; or (vi) a combination thereof.

In another embodiment, the patient is diagnosed with CHAPLE when the patient has at least one CHAPLE related symptom and at least one of the following is detected: (i) at least one mutation in a DNA sequence, an RNA sequence or a cDNA sequence of CD55 that results in a CD55 protein with substantially diminished functional activity, a CD55 protein with no functional activity, a lack of expression of CD55 protein (i.e., no CD55 protein expression), or a substantially diminished expression of CD55 protein; (ii) a CD55 protein with substantially diminished functional activity; (iii) a CD55 protein with no functional activity; (iv) a lack of expression of CD55 protein (i.e., no CD55 protein expression); (v) a substantially diminished expression of CD55 protein; or (vi) a combination thereof.

The sample can be any sample that would contain genome DNA (gDNA) or that normally contains CD55 (i.e., a sample in which CD55 is found/expressed in an individual without CHAPLE). For example, the sample may be a blood sample, such as peripheral blood mononuclear cells (PBMC). Providing a sample can comprise at least one of: obtaining a sample from a patient (e.g., at least one PBMC), isolating gDNA from a patient sample, isolating (and/or purifying) protein from a patient sample or a combination thereof.

The CHAPLE associated symptom can include at least one of the following symptoms: inflammatory bowel disease, enteropathy, protein losing enteropathy, protein losing enteropathy associated with hypoalbuminemia, hypoalbuminemia, hypogammaglobulinemia, intestinal lymphangiectasia, lymphangiectasia, thrombotic events, thromboembolism, hyperactivation of complement, angiopathic thrombosis, hypoproteinemia, or a combination thereof. For example, the patient may have at least one, at least two, at least three, at least four, at least five, at least six, at least seven, at least eight, at least nine, at least ten, at least eleven, at least twelve or all thirteen of the symptoms. In particular embodiments, the patient may have at least one of the following symptoms: inflammatory bowel disease, protein losing enteropathy associated with hypoalbuminemia, hypogammaglobulinemia, intestinal lymphangiectasia, thrombotic events or a combination thereof. For example, the patient can have at least two of the symptoms, at least three of the symptoms, at least four of the symptoms, or all five of the symptoms. That is, in certain embodiments, the patient has inflammatory bowel disease, protein losing enteropathy associated with hypoalbuminemia, hypogammaglobulinemia, intestinal lymphangiectasia, and thrombotic events.

The method can further comprise administering an effective amount of a composition of the present disclosure to the subject with CHAPLE, wherein the composition is effective in treating or preventing at least one symptom of CHAPLE. For example, the composition may comprise at least one complement inhibitor. The complement inhibitor can be selected from the group consisting of at least one serine protease inhibitor, at least one soluble complement regulator, at least one therapeutic antibody or antigen-binding fragment thereof, at least one complement component inhibitor, and at least one anaphylatoxin receptor antagonist.

In a further embodiment, the method further includes administering at least one additional agent selected from the group consisting of an anticoagulant or a thrombolytic agent, somatostatin analogues (e.g., octreotide), glucocorticoids, mesalizine, another immunosuppressive agent (e.g., TNF-α blocker), an albumin transfusion, intravenous immunoglobulins or a combination thereof. The additional agent can be included within the composition where appropriate or co-administered, as discussed above.

In an embodiment, the method of diagnosing a patient with CHAPLE can further comprise confirming the diagnosis by administering the composition of the present disclosure, thereby treating at least one symptom of CHAPLE (i.e., a CHAPLE related symptom) or preventing the reoccurrence of at least one symptom of CHAPLE.

The mutation of the present disclosure, i.e., mutations in the DNA sequence of the CD55 gene (which can be determined or detected by a mutation in the RNA sequence of the CD55 transcript (e.g., mRNA) or the DNA sequence of CD55 cDNA), can result in a near to complete absence of CD55 protein expression or the expression of CD55 protein with substantially diminished function or that is non-functional. That is, the mutant CD55 protein can have diminished (or decreased) function relative to wild-type CD55. For example, mutant CD55 may bind C4b and/or C3b with lesser (or decreased) affinity and/or avidity, or not at all. In certain embodiments, CD55 is not present or substantially not present in patients with CHAPLE syndrome/disease.

As discussed above, the mutation in the DNA sequence of the CD55 gene (and therefore, the RNA sequence of the transcript and the DNA sequence of the cDNA of the CD55 gene) can be any mutation that results in: (i) the expression of CD55 protein with decreased function relative to wild-type CD55 (e.g., CD55 protein with substantially no ability to bind C3b and/or C4b); and/or (ii) a decreased amount of CD55 expression relative to wild-type CD55 (e.g., no expression of CD 55 protein). For example, the mutation in the DNA sequence of the CD55 gene (which one skilled in the art would appreciate that these mutations can be detected in the RNA and DNA sequences of CD55 transcripts and cDNA, respectively) can be at least one of c.149-150delAA, c.149-150insCCTT, c.109delC, c.800G>C, c.287-1G>C, c.149-150delAAinsCCTT or a combination thereof. That is, in an embodiment, the DNA sequence of the CD55 gene has at least one, at least two, at least three, or all four of the above-mentioned mutations in the DNA sequence of the CD55 gene, or the related transcript or cDNA.

In further embodiments, detecting can include at least one of: (i) sequencing at least a portion of the CD55 gene or the CD55 transcript or the CD55 cDNA (or amplicons produced from the CD55 gene, transcript, or cDNA); or (ii) contacting a labeled nucleic acid probe (e.g., 1, 2, 3, 4, 5, 6, 7, 8, 9, 10, or more probes) to at least a portion of the CD55 gene or the CD55 transcript or the CD55 cDNA (or amplicons produced from the CD55 gene, transcript, or cDNA); or (iii) contacting at least a portion of the CD55 gene or CD55 transcripts or the CD55 cDNA (or amplicons produced from the CD55 gene, transcript, or cDNA) with a microarray; or (iv) a combination thereof.

Hybridization of the labeled nucleic acid probe brought into contact with CD55 gDNA, RNA transcripts, or cDNA (or amplicons produced from the CD55 gene, transcript, or cDNA) from the patient's sample can be indicative of a mutation in the portion of the CD55 gene or CD55 transcript or the CD55 cDNA. Alternatively, hybridization of the labeled nucleic acid probe that was brought into contact with CD55 gDNA, RNA transcripts, or cDNA (or amplicons produced from the CD55 gene, transcript, or cDNA) from the patient's sample can be indicative of the portion of the CD55 gene or CD55 transcript or the CD55 cDNA having a wild-type sequence at (or lacking CD55 associated mutations in the portion hybridized) the location of hybridization.

Sequencing at least a portion of the CD55 gene (or the CD55 transcript or CD55 cDNA that is produced from the CD55 transcripts) can include amplifying at least one region of interest for sequencing. The region of interest for sequencing can include any coding sequence (exon) of the CD55 gene or any CD55 exon and portions that flank the exons. For example, in a particular embodiment, at least one polymerase chain reaction (PCR) is performed with at least one of the following primer sets to produce amplicons of the CD55 gene, mRNA (e.g., transcripts), and/or cDNA: (i) CTACTCCACCCGTCTTGTTTGT (SEQ ID NO.4) and TTTGGGGGTTAAGGATACAGTC (SEQ ID NO.5) (Exon 1); (ii) CAGGTGTGGCATTTCAAGG (SEQ ID NO.6) and ACCCTGGGGTTTAGTAACGC (SEQ ID NO.7) (Exon 2); (iii) AAGTACTAAATATGCGCAAAGCAG (SEQ ID NO.8) and ATGGTCCTATCAAGAAACATCC (SEQ ID NO.9) (Exon 3); (iv) GTTACCTTCTTTGTGTGTATGCC (SEQ ID NO.10) and GCTGTGAATACCAGTCATGAAAC (SEQ ID NO.11) (Exon 4); (v) AACCTGGAGAATTTGAGGAAAG (SEQ ID NO.12) and TGTGCTAATATTCTTAAGGGGC (SEQ ID NO.13) (Exon 5); (vi) GCATTTATAAGCATCTCTTGTTGG (SEQ ID NO.14) and TCATTGAATGTCTGCAACCC (SEQ ID NO.15) (Exon 6); (vii) CTAGGTGTTTGTGGGGAGAGAG (SEQ ID NO.16) and TCTGGTGGGTTTCTGAAGAGTT (SEQ ID NO.17) (Exon 7); (viii) TTTACGCAGAGTCCTTCAGC (SEQ ID NO.18) and CCATTTAATCCTGCAATCTTGG (SEQ ID NO.19) (Exon 8); (ix) TGGAAATTTGAGTTGCTTTCG (SEQ ID NO.20) and TCTCCCAGGAATATGGATTG (SEQ ID NO.21) (Exon 9); (x) GCACCCCAAATTAACTGATTC (SEQ ID NO.22) and ATGTGATTCCAGGACTGCC (SEQ ID NO.23) (Exon 10); or (xi) a combination thereof.

Contacting a labeled nucleic acid probe to at least a portion of the CD55 gene (or the CD55 transcript or the CD55 cDNA produced from the CD55 transcript, or amplicons produced from the CD55 gene, transcript, or cDNA) can be performed or accomplished with real-time PCR. Hybridization of a real-time PCR probe can be indicative of a mutation in the portion of the CD55 gene or CD55 transcript or CD55 cDNA (or amplicons produced from the CD55 gene, transcript, or cDNA). Alternatively, hybridization of a real-time PCR probe can be indicative of the portion of the CD55 gene or CD55 transcript or CD55 cDNA (or amplicons produced from the CD55 gene, transcript, or cDNA) having a wild-type sequence at the location of hybridization (or amplicons produced from the CD55 gene, transcript, or cDNA). Furthermore, contacting a labeled nucleic acid probe to at least a portion of the CD55 cDNA (or amplicons produced from the CD55 transcripts or cDNA) may comprise: isolating CD55 transcripts; reverse transcribing at least a portion of the CD55 transcripts; and contacting the cDNA with the labeled nucleic acid probe. This may further comprise amplifying a portion or region of interest via PCR (see discussion above) prior to contacting the amplicons produced from CD55 cDNA with the labeled nucleic acid probe.

The microarray can include probes (e.g., immobilized probes) designed or configured to detect or bind CD55 gene (i.e., the sense and/or antisense DNA stand(s)), transcripts (i.e., mRNA), or cDNA sequence (or amplicons produced from the CD55 gene, transcript, or cDNA) of a patient with at least one mutation that result in the complete absence in CD55 protein or a CD55 protein with substantially diminished or devoid of function, as described above. Alternatively, the microarray can include probes (e.g., immobilized probes) designed or configured to detect or bind a wild-type CD55 DNA, transcript (i.e., RNA), or cDNA sequence (or amplicons produced from the CD55 gene, transcript, or cDNA) of a patient or subject. In a further embodiment, the microarray may include probes designed or configured to individually detect (i.e., separately detect) both CD55 mutations and wild-type CD55.

As used herein, the terms "probe(s)" and "primer(s)" refers to oligonucleotide sequences that may readily be prepared based on the CD55 nucleic acids described herein. A probe may comprise an isolated nucleic acid attached to a detectable label or reporter molecule. In any aspect or embodiment described herein, the detectable label or label is selected from the group consisting of an enzyme, a chemiluminescent agent, a ligand, biotin, streptavidin, a radioactive molecule, and an immunofluorescent protein or dye. Methods for labeling and guidance in the choice of labels appropriate for various purposes are discussed, e.g., in Sambrook et al. (1989) and Ausubel et al. (1987). "Primers" are short nucleic acids, such as DNA oligonucleotides 15 nucleotides or more in length (e.g., 12, 13, 14, 15, 16, 17, 18, 19, 20, 21, 22, 23, 24, 25, 26, 27, 28, 29, or 30 nucleotides in length). Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, 1991, Whitehead Institute for Biomedical Research, Cambridge, MA). One of skill in the art will appreciate that the specificity of a particular probe or primer increases with its length. Thus, for example, a primer comprising 20 consecutive nucleotides of the human CD55 cDNA, RNA, or gene will anneal to a-target sequence such as a CD55 gene within a genomic DNA sample with a higher specificity than a corresponding primer of only 15 nucleotides. Thus, in order to obtain greater specificity, probes and primers may be selected that comprise 20, 25, 30, 35, 40, 50 or more consecutive nucleotides that are complementary to the nucleotide sequence at the site of a mutation as described herein or the wild-type sequence at the same location.

Thus, the probe or probes of the present disclosure can include a nucleic acid sequence that is complementary (e.g., hybridizes under stringent conditions) to the site of a mutation as described herein or the wild-type nucleic acid sequence at the same location. The probe can include complementary bases 5' and 3' of the site of mutation. For example, the probe includes complementary bases 5' of the site of mutation by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50 nucleotides (e.g., the probe include complementary bases 5' of the site of mutation by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50 nucleotides). For example, the probe includes complementary bases 3' of the site of mutation by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50 nucleotides (e.g., the probe include complementary bases 3' of the site of mutation by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50 nucleotides). As described above, in certain embodiments, the probe is complementary to the wild-type sequence, wherein no hybridization is indicative of a mutation and/or hybridization is indicative of no mutation. In other embodiments, the probe is complementary to a mutation as described herein, wherein hydridization is indicative of a mutation and/or no hybridization is indicative of no mutation. As described above, the probe can be complementary to the mRNA, the DNA sense strand, the DNA anti sense strand, and/or cDNA.

In any aspect or embodiments described herein, the nucleic acid probes and/or primes of the disclosure hybridize specifically to target polynucleotides of interest (i.e., a wild-type nucleic acid sequence or a mutation containing nucleic acid sequence as described herein) under stringent conditions. Two molecules hybridizing to each other under stringent conditions is an indication that the two nucleic acid sequences are substantially identical. Stringent conditions are sequence dependent and different under different environmental parameters and for different assays. As used herein, "stringent conditions" or astringent hybridization conditions means any conditions in which hybridization will occur when there is at least about 95%, at least 96%, at least 97%, at least 98%, or at least 99% nucleotide complementarity or identity (e.g., about 95% to about 100% or about 97 to about 100%, such as about 95%, about 96%, about 97%, about 98%, about 99%, or about 100%) between the nucleic acids (e.g., a polynucleotide of interest and a nucleic acid probe). For example, stringent conditions for may be selected to be about 5T to 20° C. lower than the thermal melting point ($T_m$) the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993) and are otherwise known in the art.

For example, appropriate high stringent hybridization conditions for microarray may include, e.g., hybridization in a buffer, such as 6×SSPE-T (0.9 M NaCl, 60 mM $NaH_2PO_4$, 6 mM EDTA and 0.05% Triton X-100) for between about 10 minutes and about at least 3 hours (e.g., at least about 15 minutes) at a temperature ranging from about 4° C. to about 37° C. In an embodiment, hybridization under high stringent conditions is carried out in 5×SSC, 50% dionized Formamide, 0.1% SDS at 42T overnight.

Hybridization specificity can be evaluated by comparing the hybridization of specificity-control nucleic acid probes to specificity-control target polynucleotides that are added to a sample in a known amount. The specificity-control target polynucleotides may have one or more sequence mismatches compared with the corresponding nucleic acid probes. In this manner, whether only complementary target polynucleotides are hybridizing to the nucleic acid probes or whether mismatched hybrid duplexes are forming is determined.

Hybridization reactions can be performed in absolute or differential hybridization formats. In the absolute hybridization format, target polynucleotides from one sample are hybridized to the probes in an array (e.g., in a microarray format) and signals detected after hybridization complex formation correlate to target polynucleotide levels in a sample. In the differential hybridization format, the differential expression of a set of genes in two biological samples is analyzed. For differential hybridization, target polynucleotides from both biological samples are prepared and labeled with different labeling moieties. A mixture of the two labeled target polynucleotides is added to an array (e.g., a microarray). The array is then examined under conditions in which the emissions from the two different labels are individually detectable. Probes in the array that are hybridized to substantially equal numbers of target polynucleotides derived from both biological samples give a distinct combined fluorescence (Shalon et al. PCT publication WO95/35505). In a preferred embodiment, the labels are fluorescent labels with distinguishable emission spectra.

After hybridization, the array (e.g., microarray) is washed to remove nonhybridized polynucleotides and complex formation between the hybridizable array elements and the target polynucleotides is detected. Methods for detecting complex formation are well known to those skilled in the art. In a preferred embodiment, the target polynucleotides are labeled with a fluorescent label and levels and patterns of fluorescence indicative of complex formation are measured. In one embodiment, the measurement is accomplished by fluorescence microscopy, preferably confocal fluorescence microscopy. An argon ion laser excites the fluorescent label, emissions are directed to a photomultiplier and the amount of emitted light detected and quantitated. The detected signal should be proportional to the amount of probe/target polynucleotide complex at each position of the microarray. The fluorescence microscope can be associated with a computer-driven scanner device to generate a quantitative two-dimensional image of hybridization intensity. The scanned image is examined to determine the abundance/expression level of each hybridized target polynucleotide. In another embodiment, the measurement of levels and patterns of fluorescence is accomplished with a fluorescent imaging device, such as a microarray scanner (e.g., Axon scanner with GenePix Pro software). As with the previous measurement method, the measurements can be used to determine the abundance/expression level of each hybridized target polynucleotide, thereby determining whether there is a mutation as described herein and/or the expression level of CD55 depending upon the technique utilized.

Detecting CD55 protein can be performed via any known protein detection technique, e.g., western blot, flow cytometry, an immunoassay, microscopy, protein immunostaining, immunoelectrophoresis, spectrophotometry, etc. For example, detecting CD55 protein can comprise: contacting the sample with at least one CD55 binding polypeptide. The CD55-binding polypeptide can be an anti-CD55 antibody or a CD55-binding fragment thereof. The CD55-binding polypeptide may be used in any assay that can detect either a wild-type CD55 protein or a mutant CD55 protein that has substantially diminished functional activity, for example, the CD55 has decreased or no binding activity for C3b and/or C4b (discussed in greater detail above), or both. The CD55 binding polypeptides can include a detectable label. For example, the labelled CD55 binding polypeptide can include a fluorescent label or an enzyme, which facilitates the detection of the CD55 protein (mutant and/or wild-type, as discussed above) via flow cytometry or ELISA/western blot, respectively. One skilled in the art would appreciate that the CD55-binding polypeptide may be utilized in numerous other techniques, e.g., see above and below, to detect mutant CD55 protein, wild-type CD55 protein, or both mutant and wild-type CD55 protein.

Detecting CD55 protein can further comprise contacting the sample or a CD55-CD55-binding polypeptide complex with at least one secondary polypeptide that binds specifically to the CD55 binding polypeptide. The secondary polypeptide can include a detectable label. The secondary polypeptide can be an antibody or fragment thereof that binds the CD55 binding polypeptide. For example, the labelled secondary polypeptide can include a fluorescent label or an enzyme, which facilitates the detection of the CD55 protein (mutant and/or wild-type, as discussed herein) via flow cytometry or ELISA/western blot, respectively.

The present disclosure contemplates the use of any suitable detection assay, which is known or becomes known to those skilled in the art. As would be appreciated by the skilled artisan in view of the present disclosure, any particular detection assay could be employed with no more than routine experimentation. In certain embodiments, the step of detecting CD55 protein is performed using at least one of a western blot, flow cytometry, an immunoassay, or a combination thereof. For example, the immunoassay can be at least one assay selected from the group consisting of enzyme-linked immunosorbent assay (ELISA), flow cytometry, radioimmunoassay, magnetic immunoassay, enzyme-linked immunospot (ELISPOT), and immunofluorescence. For example, detecting CD55 protein can be performed using a western blot of protein isolated from (e.g., a crude or purified protein isolate) the patient sample (e.g., PBMCs) or flow cytometry performed on, e.g., PBMCs, in which CD55 is detected with a CD55-binding polypeptide, which includes a detectable label (or marker) or via at least one secondary polypeptide that includes a detectable label (or marker). Alternatively, a sandwich (or capture) ELISA could be utilized, in which the PBMCs are captured by, e.g., an antibody known to bind the surface of a PBMC (or a CD55 binding protein) thereby capturing the PBMCs, and detecting CD55 protein through the binding of a CD55-binding polypeptide. The CD55-binding polypeptide can include a detectable label or a secondary polypeptide with a detectable label may be used, as discussed herein.

In another embodiment, the detecting of CD55 binding function includes examining at least one of C3b affinity, C3b avidity, C4b affinity, C4b avidity or a combination thereof. That is, CD55 binding to C3b and/or C4b may be assessed by determining the affinity and/or avidity of the CD55-C3b or CD55-C4b interaction/binding. Examination of this function interaction (e.g., affinity and/or avidity) can be performed by methods well-known in the art with routine experimentation for one skilled in the art.

In a particular embodiment, detecting complement deposition includes detecting C3d deposition. For example, the patient sample (e.g., PBMCs) may be contacted with a C3d binding polypeptide. The Cd3 bound Cd3 binding polypeptide can include a detectable label (or marker) or the complex may be detected with a secondary polypeptide that is specific for the Cd3 binding polypeptides and has a detectable label. As such, Cd3 may be detected by any of the methods articulated for detecting CD55, such as flow cytometry or ELISA.

In a further aspect, the disclosure provides a method of treating a patient having CD55 deficiency, hyperactivation of complement, angiopathic thrombosis and protein losing enteropathy (CHAPLE) or preventing at least one symptom of CHAPLE in a patient at risk of developing the same. The method comprises administering an effective amount of a composition comprising at least one (e.g., at least two, at least three, at least four, or at least five) complement inhibitor (e.g., one, two, three, four, five, six, seven, eight, nine, or ten complement inhibitors) to a subject in need thereof, wherein the composition is effective in treating and/or preventing at least one symptom of CHAPLE.

In some embodiments, the complement inhibitor is at least one of a serine protease inhibitor, a soluble complement regulator, a therapeutic antibody or an antigen-binding fragment thereof, a complement component inhibitor (e.g., a small molecule), an anaphylatoxin receptor antagonist, or a combination thereof.

In certain embodiments, the serine protease inhibitors is at least one of a C3 convertase inhibitor, a C5 convertase inhibitor, a C1 inhibitor, a C1r inhibitor, a C1s inhibitor, a C2a inhibitor, a MASP-1 inhibitor, a MASP-2 inhibitor, a factor D inhibitor, a factor B inhibitor, a factor I inhibitor or a combination thereof. For example, the serine protease inhibitor can be at least one of the metBCX-1470 (BioCryst, Birmingham, AL, USA), C1s-INH-248 (Knoll/Abbott, Abbott Park, IL, USA), compstatin, Cetor® (Sanquin, Amsterdam, Netherlands), Berinert® (CSL Behring, King of Prussia, PA, USA), Cinryze™ (ViroPharma, Exton, PA, USA), rhC1INH (Pharming Group N.V., Leiden, Netherlands), Ruconest® (Salix Pharmaceuticals, Inc., Raleigh, NC, USA) or a combination thereof. Eculizumab is a recombinant humanized monoclonal antibody to C5, which inhibits the cleavage of C5 to C5a and C5b by the C5 convertase. As such, eculizumab is a terminal complement inhibitor that prevents C5b-9 formation (see, e.g., U.S. Pat. No. 9,409,980). Eculizumab was approved by the US Food and Drug Administration (FDA) in 2007 for the treatment of PNH and in 2011 for the treatment of aHUS.

In other embodiments, the soluble complement regulator is at least one of a soluble form of a membrane cofactor protein (MCP or CD46), a soluble form of a decay-accelerating factor (DAF or CD55), a soluble form of a membrane attack complex-inhibitor protein (MAC-IP or CD59), a soluble form of complement receptor 1 (CD35) or a combination thereof. For example, the soluble complement regulator can be at least one of sCR1 (TP10; Advant Immunotherapeutics, Needham, MA, USA), sCR1-sL$^{ex}$ (TP10; Advant Immunotherapeutics, Needham, MA, USA), sDAG-sMCP hybrid (MLN-2222, Millennium, Cambridge, MA, USA), a membrane-tethered sCD59 (Mirococept or APT070; Inflazyme Pharmaceuticals, Vancouver, British Columbia, Canada) or a combination thereof.

In further embodiments, the therapeutic antibody or the antigen-binding fragment thereof is at least one polypeptide that binds C3, C3a, C3b, C3 convertase, C5, C5a, C5b, C5 convertase, C7, C8, or C9, factor B, factor D, C4, C2, C1, properdin, a functional blocking antibody of an anaphylatoxin or a combination thereof. The binding can inhibit complement activation by at least one of blocking association/binding with other complement proteins, blocking association/binding with receptor proteins, blocking serine protease activity or a combination thereof. For example, the therapeutic antibody or the antigen-binding fragment thereof can be at least one of eculizumab (Soliris®; Alexion Pharmaceuticals Inc., New Haven, CT, USA), ALXN1007 (Alexion Pharmaceuticals Inc., New Haven, CT, USA), neutrazumab (G2 Therapies, Darlinghurst, NSW, Australia), Pexelizumab (Alexion Pharmaceuticals Inc., New Haven, CT, USA), ofatumumab (Genmab A/S, Copenhagen, Denmark), HuMax-CD38 (Benmab A/S, Copenhagen, Denmark), TNX-558 (Tanox, South San Francisco, CA, USA), TNX-234 (Tanox, South San Francisco, CA, USA), TA106 (Taligen, Aurora, CO, USA), anti-properdin (Novelmed, Cleveland, OH, USA) or a combination thereof. The therapeutic antibody or antigen-binding fragment thereof, may be a linear antibodies, single-chain antibody molecules (e.g., scFv), $F(ab')_2$ fragments, Fab' fragments, or multi-specific antibodies formed from antibody fragments. Furthermore, the antibody or antigen-binding fragment thereof may be a humanized antibody, e.g. a humanized anti-05 antibody. Additionally, the antibody may be a monoclonal antibody, such as an anti-C5 monoclonal antibody. For example, the antibody may be a monoclonal, humanized anti-05 antibody.

In yet other embodiments, the complement component inhibitor is a peptide, nucleic acids, a synthetic molecule or a combination thereof that disrupts protein functions by steric hindrance or the induction of conformational changes. For example, the complement component inhibitor can be at least one of compstatin, anti-C5 RNA aptamer (ARC1905; Archemix, Cambridge, MA, USA), or analogs or derivatives thereof, or a combination thereof.

In another embodiment, the anaphylatoxin receptor antagonist is at least one of a C5aR antagonist, a C5L2 antagonist, a C3a receptor antagonist, a functional blocking antibody of an anaphylatoxin or a combination thereof. For example, the anaphylatoxin receptor antagonist is at least one of PMX-53 (PepTech Corp, Bedform, MA, USA), PMX-205 (PepTech Corp, Bedform, MA, USA), JPE-1375 (Jerini, Berlin, Germany), JSM-7717 (Jerini, Berlin, Germany), rhMBL (Enzon Pharmaceuticals, Cranford, NJ, USA) or a combination thereof.

In another aspect, the disclosure provides a composition for treating or preventing at least one symptom of CD55 deficiency, hyperactivation of complement, angiopathic thrombosis and protein losing enteropathy (CHAPLE). The composition comprises an effective amount of two or more agents, wherein at least one of the agents is a complement inhibitor to a subject in need thereof, and the composition is effective in treating or preventing at least one symptom of CHAPLE. In an embodiment, the least two of the agents are a complement inhibitor, e.g., a C3 convertase inhibitor and a C5 convertase inhibitor. In another embodiment, the effective amount is a synergistically effective amount. In another embodiment, the composition is a therapeutic composition further comprising a pharmaceutically acceptable carrier.

In an additional embodiment, the complement inhibitor is selected from the group consisting of a serine protease inhibitor, a soluble complement regulator, a therapeutic antibody or an antigen-binding fragment thereof, a complement component inhibitor, and an anaphylatoxin receptor antagonist, each as described herein.

In further embodiments, the complement inhibitors include a C3 convertase inhibitor and a C5 convertase inhibitor. In other embodiments the complement inhibitors include a soluble form of a CD55 and at least one of a C3 convertase inhibitor, a C5 convertase inhibitor or a combination thereof.

In certain embodiments, the serine protease inhibitors is at least one of a C3 convertase inhibitor, a C5 convertase inhibitor, a C1 inhibitor, a C1r inhibitor, a C1s inhibitor, a C2a inhibitor, a MASP-1 inhibitor, a MASP-2 inhibitor, a factor D inhibitor, a factor B inhibitor, a factor I inhibitor or a combination thereof.

In a particular embodiment, the serine protease inhibitor is at least one of BCX-1470 (BioCryst, Birmingham, AL, USA), C1s-INH-248 (Knoll/Abbott, Abbott Park, IL, USA), compstatin, Cetor® (Sanquin, Amsterdam, Netherlands), Berinert® (CSL Behring, King of Prussia, PA, USA), Cinryze™ (ViroPharma, Exton, PA, USA), rhC1INH (Pharming Group N.V., Leiden, Netherlands), Ruconest® (Salix Pharmaceuticals, Inc., Raleigh, NC, USA) or a combination thereof.

In other embodiments, the soluble complement regulator is at least one of a soluble form of a membrane cofactor protein (MCP or CD46), a soluble form of a decay-accelerating factor (DAF or CD55), a soluble form of a membrane attack complex-inhibitor protein (MAC-IP or CD59), a soluble form of complement receptor 1 (CD35) or a combination thereof.

In an embodiment, the soluble complement regulator is at least one of sCR1 (TP10; Advant Immunotherapeutics, Needham, MA, USA), sCR1-sL$^{ex}$ (TP10; Advant Immunotherapeutics, Needham, MA, USA), sDAG-sMCP hybrid (MLN-2222, Millennium, Cambridge, MA, USA), a membrane-tethered sCD59 (Mirococept or APT070; Inflazyme Pharmaceuticals, Vancouver, British Columbia, Canada) or a combination thereof.

In other embodiments, the therapeutic antibody or the antigen-binding fragment thereof is at least one polypeptide that binds C3, C3a, C3b, C3 convertase, C5, C5a, C5b, C5 convertase, C7, C8, or C9, factor B, factor D, C4, C2, C1, properdin, a functional blocking antibody of an anaphylatoxin or a combination thereof, wherein said binding inhibits complement activation by at least one of blocking association/binding with other complement proteins, blocking association/binding with receptor proteins, blocking serine protease activity or a combination thereof.

In certain embodiments, the therapeutic antibody or the antigen-binding fragment thereof is at least one of eculizumab (Soliris®; Alexion Pharmaceuticals Inc., New Haven, CT, USA), ALXN1007 (Alexion Pharmaceuticals Inc., New Haven, CT, USA), neutrazumab (G2 Therapies, Darlinghurst, NSW, Australia), Pexelizumab (Alexion Pharmaceuticals Inc., New Haven, CT, USA), ofatumumab (Genmab A/S, Copenhagen, Denmark), HuMax-CD38 (Benmab A/S, Copenhagen, Denmark), TNX-558 (Tanox, South San Francisco, CA, USA), TNX-234 (Tanox, South San Francisco, CA, USA), TA106 (Taligen, Aurora, CO, USA), anti-properdin (Novelmed, Cleveland, OH, USA) or a combination thereof.

In yet other embodiments, the complement component inhibitor is a peptide, nucleic acids, a synthetic molecule or a combination thereof that disrupts protein functions by steric hindrance or the induction of conformational changes.

In a particular embodiment, the complement component inhibitor is at least one of compstatin, anti-C5 RNA aptamer (ARC1905; Archemix, Cambridge, MA, USA), or analogs or derivatives thereof, or a combination thereof.

In additional embodiments, the anaphylatoxin receptor antagonist is at least one of a C5aR antagonist, a C5L2 antagonist, a C3a receptor antagonist, a functional blocking antibody of an anaphylatoxin or a combination thereof.

In certain embodiments, the anaphylatoxin receptor antagonist is at least one of PMX-53 (PepTech Corp, Bedform, MA, USA), PMX-205 (PepTech Corp, Bedform, MA, USA), JPE-1375 (Jerini, Berlin, Germany), JSM-7717 (Jerini, Berlin, Germany), rhMBL (Enzon Pharmaceuticals, Cranford, NJ, USA) or a combination thereof Therapeutic Compositions Pharmaceutical compositions comprising combinations of an effective amount of at least two agents (e.g., therapeutic agents), wherein one or more of the agents is a complement inhibitor, all in effective amounts (e.g., synergistically effective amounts), in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of the compounds (e.g., agents and/or complement inhibitors) of the composition described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of the active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action. In certain preferred aspects of the disclosure, one or more compounds according to the present disclosure are coadministered with another bioactive agent including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The present disclosure also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the present disclosure can potentially localize the drug, for example, in certain tissue types, such as the tissues of the reticular endothelial system (RES). A liposome formulation which can facilitate the association of drug with the surface of cells, such as, lymphocytes and macrophages is also useful.

The present disclosure also features the use of the composition comprising surface-modified liposomes containing poly (ethylene glycol) lipids (PEG-modified, or long-circulating liposomes or stealth liposomes). Polypeptides and compositions of the present disclosure can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present disclosure also includes compositions prepared for storage or administration which include a pharmaceutically effective amount of the desired compounds (e.g., agents and/or complement inhibitors) in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

An effective amount, pharmaceutically effective dose, therapeutically effective amount, or pharmaceutically effective amount is that dose required to prevent, inhibit the occurrence, or treat (alleviate a symptom to some extent, preferably all of the symptoms) of a disease state or pathological condition. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the negatively charged polymer. In addition, effective amounts of the compositions of the disclosure encompass those amounts utilized in the examples to facilitate the intended or desired biological effect.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds (e.g., agents and/or complement inhibitors) that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising at least two agents, wherein at least one is a complement inhibitor, and a pharmaceutically acceptable carrier. For example, two or more complement inhibitors can be present in association with one or more non-toxic pharmaceutically acceptable carriers and/or diluents and/or adjuvants, and if desired other active ingredients. The pharmaceutical compositions of the present disclosure can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the present disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water. The composition can also be administered to a subject in combination with other therapeutic compounds to increase the overall therapeutic effect. The use of multiple compounds to treat an indication can increase the beneficial effects while reducing the presence of side effects.

A further object of the present disclosure is to provide a kit comprising a suitable container, the therapeutic of the present disclosure in a pharmaceutically acceptable form disposed therein, and instructions for its use.

Preparations for administration of the therapeutic of the present disclosure include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The compounds or peptides (e.g., agent, agents, and/or complement inhibitors; also referred to herein as "active compounds") of the disclosure, and derivatives, fragments, analogs and homologs thereof, can be incorporated into pharmaceutical compositions suitable for administration. Such compositions typically comprise the compound or protein and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the present disclosure is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™. (BASF, Parsippany, NJ) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated to give controlled release of the active compound. For buccal administration the compositions may take the form of tablets or lozenges formulated in conventional manner. For administration by inhalation, the compounds for use according to the present disclosure are conveniently delivered in the form of an aerosol spray presentation from pressurized packs or a nebuliser, with the use of a suitable propellant, e.g., dichlorodifluoromethane, trichlorofluoromethane, dichlorotetrafluoroethan-e, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

Additional objects and advantages of the present disclosure will be appreciated by one of ordinary skill in the art in light of the current description and examples of the preferred embodiments, and are expressly included within the scope of the present disclosure.

EXAMPLES

Materials and Methods.

Figure 1A:
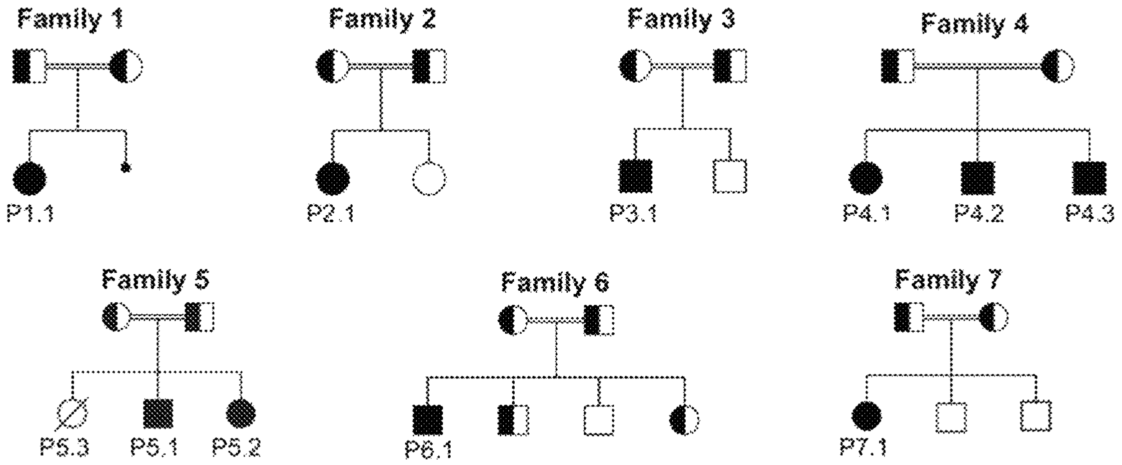
FIGS. 1A, 1B, 1C, 1D, 1E, 1F, 1G, and 1H. Clinical presentation of 7 families with familial early onset PLE. Pedigrees of seven families with affected individuals homozygous for alternative allele indicated by solid symbols, heterozygous individuals indicated by half solid symbols, and affected individuals with an unknown genotype indicated by open symbols with a slash through it. The double line between parents in each family indicates presence of consanguinity (A). Serum levels of immunoglobulin G (IgG, left Y axis) in relation to serum albumin (right Y axis) concentrations as a function of age in years. Age-specific lower cutoff value for IgG is denoted by the red dotted curve, whereas the reference for albumin level is >3.5 g/dl (indicated by hatched line on right Y axis). Each arrow denotes an episode of pneumonia. Presented data for Patients 1.1, 2.1, 3.1, and 4.1 (B). Radiological exams showing bowel wall edema/thickening in Patient 6.1. Double arrows indicate diffuse target-water small bowel wall enhancement and single arrow indicates scattered area of dilatation (C). The hematoxylin and eosin stained histological section from the resection specimen from P2.1 shows lymphangiectasia (D). Immunohistochemical stains for PROX-1 and D2-40 (Podoplanin) (inset). Radiographs showing large occlusive thrombi in the inferior vena cava (IVC) and right atrium (arrows in E, left). Radiograph showing pulmonary embolus and lack of vascular flow in right pulmonary artery branches (arrows in E, center). Radiograph showing irregular peripheral arteriovenous malformations (ovals in E, right). Colonoscopy photographs of Patient 1.1 showing exudate formation (upper, arrow) and a mucosal ulcer (lower, arrow) in the terminal ileum (F). Histopathology of colon biopsy specimen taken from hematoxylin and eosin sections of ileum of Patient 2.1 demonstrating prominent lymphoid nodules evident within both the mucosa and beneath the muscularis mucosa; and immunohistochemistry showing infiltrates of B cells (CD20) and T cells (CD3) within lymphoid nodules (G). Abdominal CT image from Patient 2.1 with intestinal obstruction showing mucosal thickening of the distal ileal segments and luminal narrowing (the lead pipe sign, arrow) (H).

Study Participants. Three initial patients, their unaffected parents, and then seven additional patients presenting with a similar clinical presentation were evaluated (FIGS. 1A and 3). The patients were followed in Marmara University, Istanbul, Turkey; Cerraphasa University, Istanbul, Turkey; Baskent University, Ankara, Turkey; Gazi University, Ankara, Turkey, and Sami Ulus Hospital, Ankara, Turkey. All of the patients were enrolled in a clinical protocol which had been approved by the institutional review boards of the respective institutions and NIH. All study participants or their parents provided written informed consent.

Genetic and Functional Analysis. Whole exome DNA sequencing (WES) was performed on the initial three patients and their unaffected parents and siblings followed by specific CD55 DNA sequencing in the other patients and family members. Complement deposition assays, cytokine secretion and T-cell stimulation assays were performed on patient samples and healthy controls. Complement deposition was verified using lentiviral and clustered regularly-interspaced short palindromic repeats (CRISPR) mediated CD55 knockdown/knockout in Jurkat T cells and HT29 epithelial cells.

Human Subjects. All human subjects (or their legal guardians) in this study provided written informed consent in accordance with Helsinki principles for enrollment in research protocols that were approved by the Institutional Review Boards of the National Institute of Allergy and Infectious Diseases, National Institutes of Health (NIH) or the CeMM Research Center for Molecular Medicine of the Austrian Academy of Sciences. Patient and healthy control blood was obtained at the respective Turkish institutions overseeing patient care under approved protocols, and shipped to either the NIH or the CeMM Research Center for Molecular Medicine of the Austrian Academy of Sciences. Additional healthy control blood was obtained at the NIH clinical center under approved protocols. Mutations will be archived by Online Mendelian inheritance in Man (OMIM), and whole-exome data will be submitted in dbGaP. A webpage through the National Center for Biotechnology Information (NCBI) will also be created to accumulate patient mutation data in the format of the Leiden Online Variant Database (LOVD) as patients are identified.

Genetic Analysis Methods. Genomic DNA (gDNA) was obtained from probands and family members by isolation and purification from peripheral blood mononuclear cells (PBMCs) using DNeasy® Blood and Tissue Kit (QIAGEN®, Hilden, Germany). DNA was then submitted for Whole Exome Sequencing (WES) or targeting sequencing of the CD55 gene. For whole exome sequencing, the Human All Exon 50 Mb kit (Agilent Technologies, Santa Clara, CA, USA) coupled with massively parallel sequencing by Illumina® HiSeg™ Sequencing System (Illumina, Inc., San Diego, CA, USA) was performed using the collected DNA. For individual samples, WES produced approximately 50-100× sequence coverage for targeted regions. WES was performed on patients 1.1, 2.1 along with 3.1 and 5.1 in which WES was combined with homozygosity mapping. As described previously, all sequenced DNA reads were mapped to the hg19 human genome reference by Burrows-Wheeler Aligner with default parameters. Single nucleotide variant and indel calling were performed using the Genome Analysis Toolkit (Broad Institute, Cambridge, MA, USA). All SNVs/indels were annotated by SeattleSeq Annotation and an in-house custom analysis pipeline was used to filter and prioritize for autosomal recessive or de novo disease-causal variants based on the clinical pedigree for Patients 1.1 and 2.1, the mutations were identified by targeted gene screening of the WES data based on the similarity of clinical phenotype in the cohort (Lucas C L, et al. Heterozygous splice mutation in PIK3R1 causes human immunodeficiency with lymphoproliferation due to dominant activation of PI3K. J Exp Med 2014; 211: 2537-47).

For targeted sequencing, CD55/DAF exons 1 through 10 were PCR amplified, purified, or gel extracted using QIAGEN's MinElute® PCR Purification Kit (QIAGEN®, Hilden, Germany) or QIAquick® Gel Extraction Kit (QIAGEN®, Hilden, Germany), respectively. Samples were submitted to the National Institute of Allergy and Infectious Disease Research Technologies Branch Core Sequencing facility for Sanger sequencing. DNA sequences were analyzed using SEQUENCHER® V.5.3 (Gene Codes Corporation, Ann Arbor, MI, USA). The primers used for Sanger sequencing and the amplicons produced therefrom are shown in Table 1, below.

TABLE 1

Primer Sequences for mutation detection in CD55

| Exon # | Forward Primer Sequence | SEQ ID NO | Reverse Primer sequence | SEQ ID NO |
|---|---|---|---|---|
| Exon 1 | CTACTCCACCCGTCTTGTTTGT | 4 | TTTGGGGGTTAAGGATACAGTC | 5 |
| Exon 2 | CAGGTGTGGCATTTCAAGG | 6 | ACCCTGGGGTTTAGTAACGC | 7 |

TABLE 1-continued

Primer Sequences for mutation detection in CD55

| Exon # | Forward Primer Sequence | SEQ ID NO | Reverse Primer sequence | SEQ ID NO |
|---|---|---|---|---|
| Exon 3 | AAGTACTAAATATGCGCAAAGCAG | 8 | ATGGTCCTATCAAGAAACATCC | 9 |
| Exon 4 | GTTACCTTCTTTGTGTGTATGCC | 10 | GCTGTGAATACCAGTCATGAAAG | 11 |
| Exon 5 | AACCTGGAGAATTTGAGGAAAG | 12 | TGTGCTAATATTCTTAAGGGGC | 13 |
| Exon 6 | GCATTTATAAGCATCTCTTGTTGG | 14 | TCATTGAATGTCTGCAACCC | 15 |
| Exon 7 | CTAGGTGTTTGTGGGGAGAGAG | 16 | TCTGGTGGGTTTCTGAAGAGTT | 17 |
| Exon 8 | TTTACGCAGAGTCCTTCAGC | 18 | CCATTTAATCCTGCAATCTTGG | 19 |
| Exon 9 | TGGAAATTTGAGTTGCTTTCG | 20 | TCTCCCAGGAATATGGATTG | 21 |
| Exon 10 | GCACCCCAAATTAACTGATTC | 22 | ATGTGATTCCAGGACTGCC | 23 |

Primary Cells and Cell Lines. Patient or control blood was subjected to a ficoll density gradient centrifugation, after which peripheral blood mononuclear cells (PBMCs) were collected from the interface. Naïve or total $CD4^+$ T cells were then isolated by negative selection using the Naïve $CD4^+$ T Cell Isolation Kit II or the human $CD4^+$ T cell isolation kit, respectively (Miltenyi Biotec Inc., Auburn, CA, USA). Jurkat E6, HEK 293T, HT29 and Caco-2 cells were purchased from the American Type Culture Collection (ATCC®; Manassas, VA, USA). Pooled Human Umbilical Vein Endothelial Cells (HUVECs) were from Lonza® (Walkersville, MD, USA).

Media. Human T cells and Jurkat T cells were either grown in either RPMI 1640 (Gibco™/ThermoFisher Scientific, Waltham, MA, USA) supplemented with 10% heat-shocked FBS (Gibco™/ThermoFisher Scientific, Waltham, MA, USA), 1% Penicillin/Streptomycin, 1% L-Glutamine and 100 units/mL IL-2 (complete RPMI) or X-Vivo 15 (Lonza) supplemented with 1% Penicillin/Streptomycin, 1% L-Glutamine and 100units/mL IL-2 (complete X-vivo 15). HT29 and HEK293T cells were grown in DMEM media (Gibco™/ThermoFisher Scientific, Waltham, MA, USA) supplemented with 10% heat-shocked FBS (Gibco™/Thermo Fisher Scientific, Waltham, MA, USA), 1% Penicillin/Streptomycin, and 1% L-Glutamine. HUVECS were cultured in Endothelial Cell Basal Medium (Lonza®, Walkersville, MD, USA) supplemented with the contents of EGM™ SingleQuot™ Kit Suppl. & Growth Factors kit (Lonza, Walkersville, MD, USA). Caco-2 cells were cultured in Minimum Essential Media (Gibco™, Waltham, MA, USA) supplemented with 20% non-heat inactivated FBS (Sigma), 1% Penicillin/Streptomycin, 1% L-Glutamine, and 10 mM HEPES.

Antibodies and Inhibitors. Anti-CD25 FITC, Anti-CD69 APC, Anti-CD4 PE, Anti-CD55 FITC, anti-CD59 FITC, anti-CD46 APC, anti-CD141/Thrombomodulin APC, anti-CD142/Thrombin PE, anti-CCR9 APC, anti-integrin α4 PE, anti-integrin β7, anti-C5aR FITC, anti-C5L2 PE, and anti-C3aR APC were purchased from BioLegend® (San Diego, CA, USA) or eBisociences, Inc. (San Diego, CA, USA). The anti-C3d antibody used in complement deposition experiments was purchased from Hycult® Biotech (Plymouth Meeting, PA, USA). LIVE/DEAD™ Fixable Near-IR Dead Cell Stain Kit used for cell viability assay was purchased from ThermoFisher Scientific (Waltham, MA, USA) and APC labeled Annexin-V was from BioLegend® (San Diego, CA, USA). The anti-CD3 antibody HIT3α used in T cell re-stimulation experiments was purchased from BioLegend® (San Diego, CA, USA). The anti-CD55 antibody (clone BRIC 216) used to costimulate T cells was from EMD Millipore (Billerica, MA, USA) or International Blood Group Reference Laboratory (IBGRL) (Filton, UK). Human CD97-fc recombinant protein used for T cell costimulation was purchased from Creative BioMart® (Shirley, NY, USA). The C3aR inhibitor, SB 290157, was purchased from Calbiochem® (San Diego, CA, USA). The C5aR1 inhibitor, NDT 9513727, was purchased from Tocris Bioscience (Bristol, UK). Anti-CD55 used for western blotting was from Sigma-Aldrich® (St. Louis, MO, USA).

Flow Cytometry. Adherent cells were treated with 0.05% trypsin EDTA to lift them from the surface followed by addition of 5% FBS to inactivate the trypsin. Suspension cells were collected from culture following mixture of the culture by repeat pipetting. Cells were washed and resuspended in FACS buffer (1% FBS, 0.05% sodium azide, and 5 mM EDTA in PBS) at $2\times10^6$ cells/mL. Staining or isotype antibodies were added at 1:200 final dilutions and incubated with cells at 4° C. for 30 minutes to 1 hour. Cells were then washed 3× and resuspended in FACS buffer with 1% PFA and analyzed by flow cytometry. Flow files were analyzed on FlowJo version 9.9 or above (FlowJo, LLC, Ashland, OR, USA).

Complement Deposition. T cells (Patient $CD4^+$ T cell blasts or Jurkat T cells) were collected and washed 3× in basal RPMI. Cells were then resuspended in basal media and rested for 2-3 hours at 37° C. to allow any deposited complement components to be cleared from the cell surface. Rested cells were then collected and resupended in basal RPMI or basal RPMI that had been adjusted to pH 6.5 (acidified media) to a final concentration of $1\times10^6$ cells/mL. Non-heat shocked pooled normal human serum was then added to cell suspension for the indicated amount of time. Human serum that had been heat shocked at 56° C. for 30 minutes was used as a negative control for complement activation. At the indicated times cells were transitioned to 4° C., and kept chilled for the remainder of the experiment. Cells were stained with a 1:300 dilution of anti-C3d antibody for 30 minutes, washed 3× and then stained with an anti-rat antibody conjugated with alexa fluor 488 at a 1:500 dilution for 30 minutes. Cells were washed 3× and resuspended in FACS buffer (PBS, 1% FBS) and analyzed for C3d deposition by flow cytometry. To analyze C3d deposition on HT29 cells, cells were either left untreated or treated overnight with 10 ng/mL TNFα to upregulate CD55 expression. Cells were then treated with trypsin/EDTA to release cells into suspension, washed, and then analyzed for C3d deposition as above.

Preparation of T cell Stimulatory Surfaces. Tissue culture treated 48, or 96 well plates were incubated with the indicated concentration of anti-CD3 in PBS for 2 hours at 37° C. Plates were then washed 3× in PBS and incubated with either anti-CD28, anti-CD55, or CD97fc for 2 hours at 37° C. Plates were again washed 3× with PBS before using in T cell stimulations.

T cell Stimulation and Cytokine Secretion. To measure T cell activation isolated CD4 T cells were either left alone or stained with 1 μM CFSE for 5 minutes at room temperature, protected from light. Labelled cells were washed 3× in complete RPMI prior to use and resupended at $1\times10^6$ cells/mL in complete RPMI. Cells were then added to stimulatory surfaces, pre-coated with the indicated concentrations of activating antibodies/proteins. To measure CD25 and CD69 upregulation, non-CFSE labeled T cells were collected after 24 hours and analyzed by flow cytometry for CD25 and CD69 expression, as detailed above. To assess T cell proliferation, CFSE labeled T cell cultures were collected after 96 hours of stimulation and analyzed by flow cytometry for CFSE dilution.

For cytokine secretion upon primary stimulation, Naïve $CD4^+$ T cells were isolated via negative selection using the Naïve $CD4^+$ T Cell Isolation Kit II, human isolation kit (Miltenyi Biotec Inc., Auburn, CA, USA). Naïve T cells were then resuspended in complete X-Vivo15 media. Dynabeads® CD3/CD28 T cell activator (Invitrogen™, Carlsbad, CA, USA) were then added to cells (1 bead/2 cells) and cells and dynabeads were centrifuged at 300×g for 5 minutes to complex beads and T cells. Cells were resuspended and added to 48 well plates at a final concentration of $5\times10^4$/mL in complete X-vivo15 media. Cell culture supernatants were collected every 24 hours starting at 96 hours post-activation for the indicated time course. Cell cultures were stored at −80° C. until analyzed. To analyze cytokine secretion upon restimulation cells were collected from day 12 to 14 of culture in complete X-Vivo15 media, washed and resuspended in basal media at 37° C. for 3 hours to rest. Cells were then collected and resuspended in complete X-Vivo15 media and stimulated for 48 hours at 37° C. with 1 μg/mL plate-bound anti-CD3. Cell supernatants were then collected and stored at −80° C. until analyzed.

Lentiviral Construction and Transfection Protocol. Lentiviral packaging constructs psPAX2 and PDM2.G were kind gifts of Dr. Nir Hacohen, Broad Institute. shRNA constructs against CD55 or empty vector were purchased from Sigma-Aldrich® (St. Louis, MO, USA). To generate lentiviral particles, $1.2\times10^6$ HEK293T cells were seeded in each well of a six well plate the day prior to transfection. Cells were then cotransfected using lipofectamine 2000 (Invitrogen™, Carlsbad, CA, USA) with 900 ng of psPAX2 and 100 ng of pDM2.G, together with 1 μg of the vector of interest (shRNA or lentiCRISPRv2). Alternatively, lentivirus was produced by the conventional calcium chloride transfection method. Supernatants were harvested 24 and 48 hours after transfection and frozen at −80° C. HT29 cells were transduced by spin infection with lentivirus. Lentivirus and 8 μg/ml Polybrene (Sigma-Aldrich®, St. Louis, MO, USA) were added to the wells of a 24-well culture plate and centrifuged at 2000 rpm and 37° C. for 2 hours. Lentivirus-containing media was then replaced with 293T media, and the cultures were maintained as described above. On day 5 of culture, puromycin (Sigma-Aldrich®, St. Louis, MO, USA) was added to a final concentration of 2 μg/ml to select for virally transduced cells. Selected cells were maintained in 2 μg/mL puromycin following initial selection.

CRISPR Materials/Methods. CRISPRs targeting CD55 were designed using an online tool (crispr.mit.edu) as previously described and cloned into a lentiCRISPRv2 vector (Ran F A et al. Genome Engineering using the CRISPR-Cas9 system. Nature Protocols 2013; 8: 2281-308; and Sanjana N E, et al. Improved vectors and genome-wide libraries for CRISPR screening. Nat Methods 2014; 11: 783-4). CRISPR lentivirus was produced according to the above protocol. Transductions were performed as above, with minor changes. For Jurkats, selection with 1 μg/mL puromycin was performed for 3 days. For Caco-2, selection with 5 μg/mL puromycin was performed for 6 days, changing the media every 2 days.

HUVEC Experiments. Huvecs grown to 80% confluency, and before passage 8, were trypsonized and replated in 24 well tissue culture plates at 200,000 cells/well in Huvec media. Twenty-four hours later the indicated concentrations of TNFα, IL10, or all trans retinoic acid (ATRA) were added. Twenty-four hours later in the cast of TNFα or IL10 treatment or 48 hours later in the case of ATRA, cells were trypsonized and stained for the indicated surface markers following the described flow cytometry staining protocol. Cells were then immediately analyzed.

Western Blotting. $CD4^+$ T cells were washed in PBS and lysed in 1% Triton X-100, 50 mM Tris-C1, pH 8, 150 mM NaCl, 2 mM EDTA, 10% glycerol, complete protease inhibitor cocktail (Roche Diagnostics, Indianapolis, IN, USA), and phosphatase inhibitor cocktails (Sigma-Aldrich®, St. Louis, MO, USA) on ice for 20 minutes. The lysates were then clarified by centrifugation at 15,000×g at 4° C. for 10 minutes. Protein concentration was determined by BCA assay (Thermo Fisher Scientific®, Waltham, MA, USA). Lysates were then diluted with 2× SDS sample buffer (quality biologicals) supplemented with 5% BME to make reducing sample buffer. Approximately 5 μg of total protein was separated by SDS-PAGE on 4-20% precast gels (Invitrogen™, Carlsbad, CA, USA) and transferred to a nitrocellulose membrane (Bio-Rad Laboratories, Philadelphia, PA, USA). Membranes were blocked with 5% nonfat dry milk in Tris-buffered saline (TBS) with 0.01% Tween-20 (TBST) for 30 minutes at room temperature before incubating with primary antibody overnight at 4° C. After three 5 minute washes with TBST at room temperature with rocking, HRP-conjugated secondary antibody was added for an additional hour at room temperature. After five 5 minute washes, HRP substrate (Luminata Forte; EMD Millipore, Billerica, MA, USA) was added to the membranes, which were then exposed to autoradiography film and developed.

Statistical Analysis. Statistics were computed using the analysis options in Prism (Graphpad Software, Inc., La Jolla, CA, USA). Either the Mann-Whitney U test or a two-tailed unpaired T test with Welch's correction was used to compare sample means. *=$p<0.05$, =$p<0.01$, *=$p<0.001$.

Patient Clinical Histories.

Figure 1B:
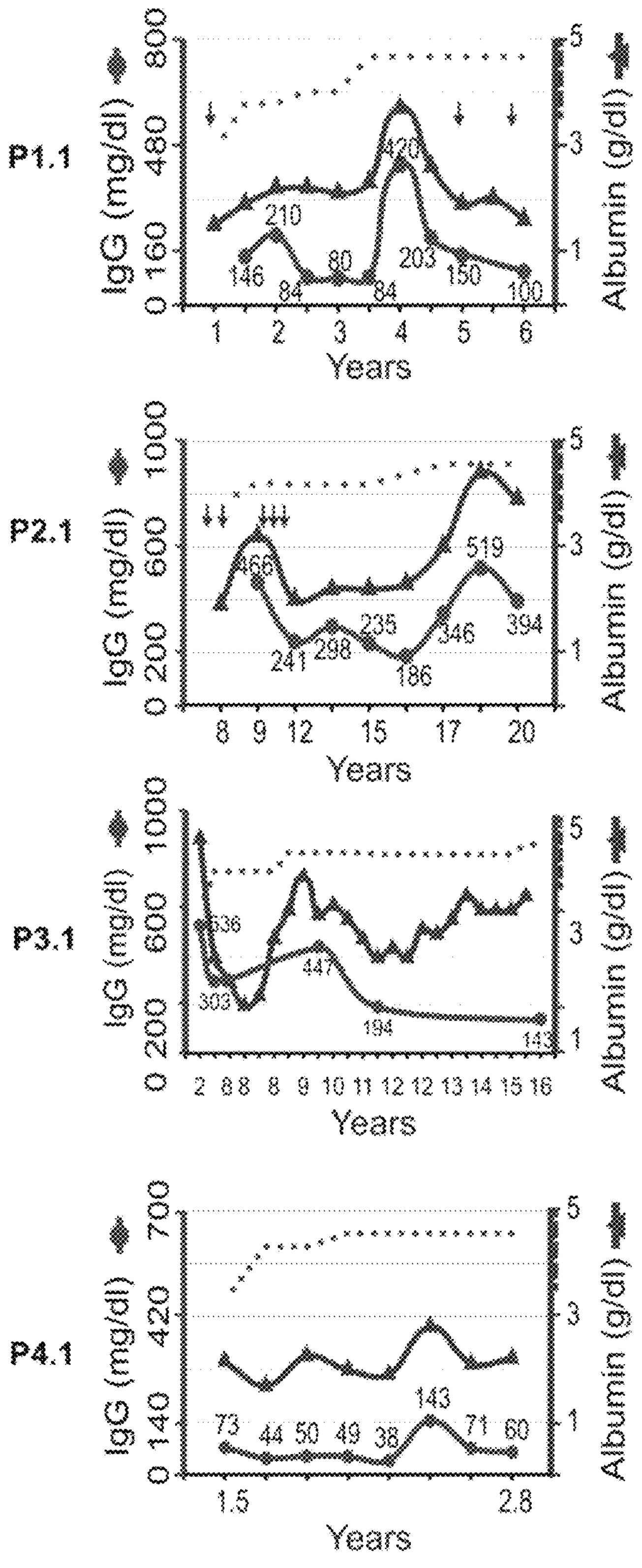

Patient 1.1, a 7 year-old girl born to consanguineous Turkish parents, presented with bloody diarrhea and vomiting at 4 weeks of age, and continued with episodes throughout childhood. At 6 months of age, she was admitted to hospital with persistent diarrhea, pneumonia, and facial/extremity edema, for which she received antibiotics and albumin replacement therapy. Endoscopic examination revealed ulcers, exudate formation and nodularity in the colon. Although the patient's gastrointestinal (GI) symptoms improved with treatment and she subsequently gained weight, long-term remission could not be achieved. The patient was placed on infliximab therapy at 6 years of age to deal with ongoing GI symptoms. Apart from GI symptoms she experienced recurrent respiratory infections at an unusually high frequency from 6 months of age. Immunologic evaluation revealed pan-hypogammaglobulinemia and she was treated with intravenous immunoglobulin (IVIG), leading to a decrease in the frequency of infections. To determine the specific antibody production we tested isohemagglutin levels, with normal Anti-A and Anti-B titers. Despite IVIG, trough levels of IgG remained below the desired range, and tracked well with levels of serum albumin (FIG. 1B). Fecal excretion of alpha-1 antitrypsin was found to be elevated, implying the role of protein losing enteropathy in refractory hypogammaglobulinemia. In addition to the biallelic loss of function in CD55, this patient was additionally positive for a homozygous LOF mutation in CD21 that resulted in loss of protein expression (data not shown).

Figure 1C:
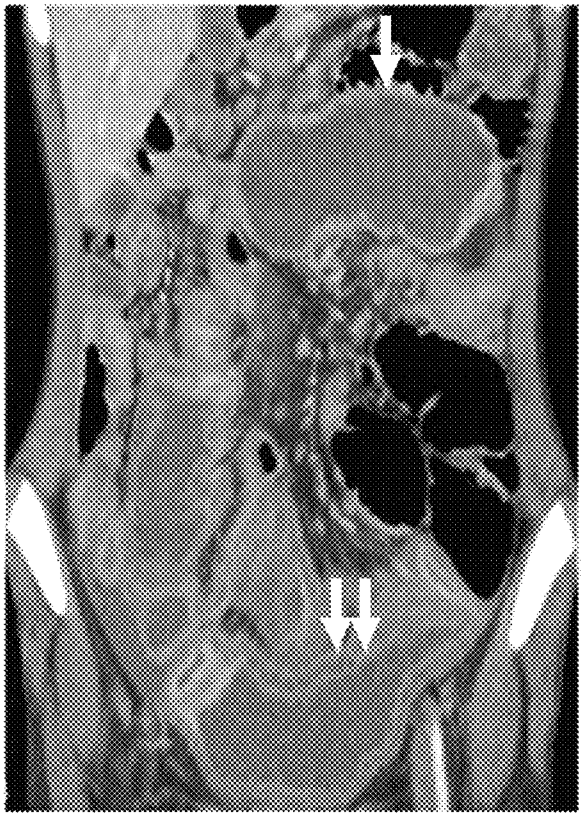
Figure 1D:
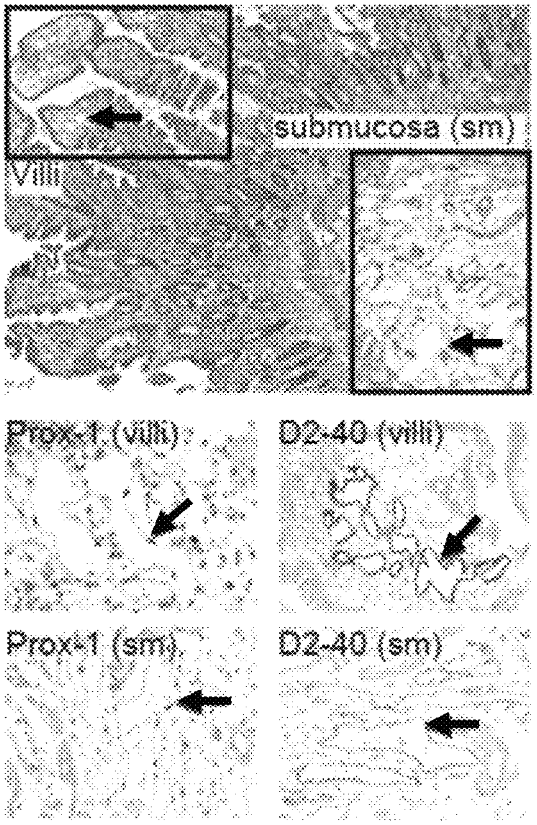
Figure 1E:
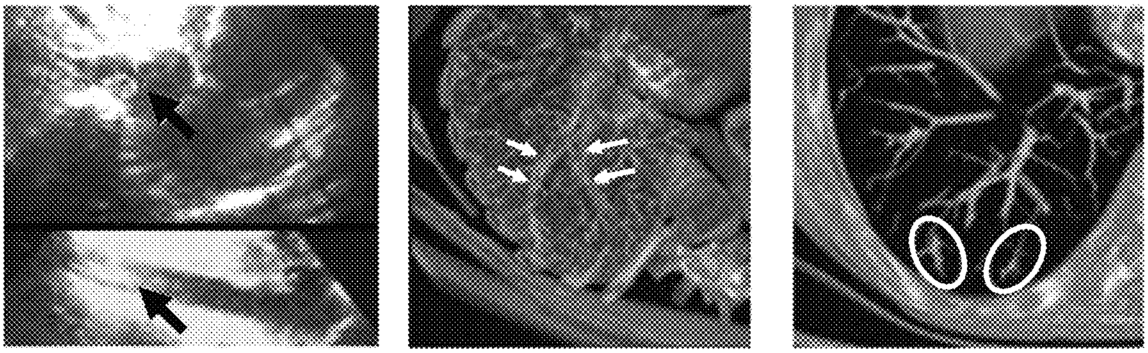
Figure 1F:
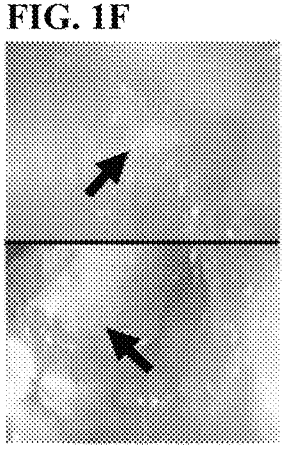
Figure 1G:
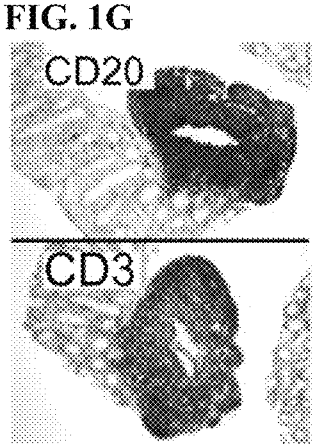
Figure 1H:
Figure 3A:
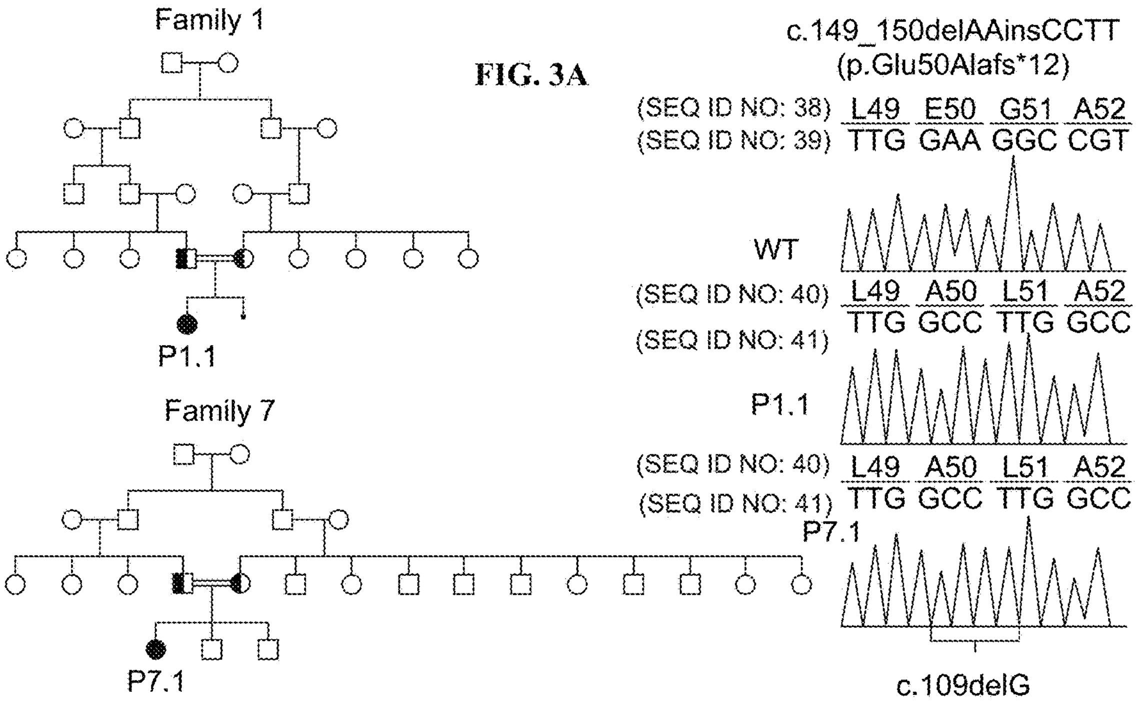
FIGS. 3A, 3B, 3C, and 3D. Pedigrees and chromatograms for families 1 and 7, families 2, 3, and 5, family 4, and family 6 are shown in 3A, 3B, 3C, and 3D respectively. Extended pedigrees for patient families, with affected individuals homozygous for alternative allele indicated by solid symbols, heterozygous individuals indicated by half solid symbols, and affected individuals with an unknown genotype indicated by open symbols with a slash. The double line between parents in each family indicates presence of consanguinity. Chromatograms showing the specific nucleotide mutations in the CD55 gene in patients relative to the reference sequence. Families are grouped by unique mutation status.
Figure 3B:
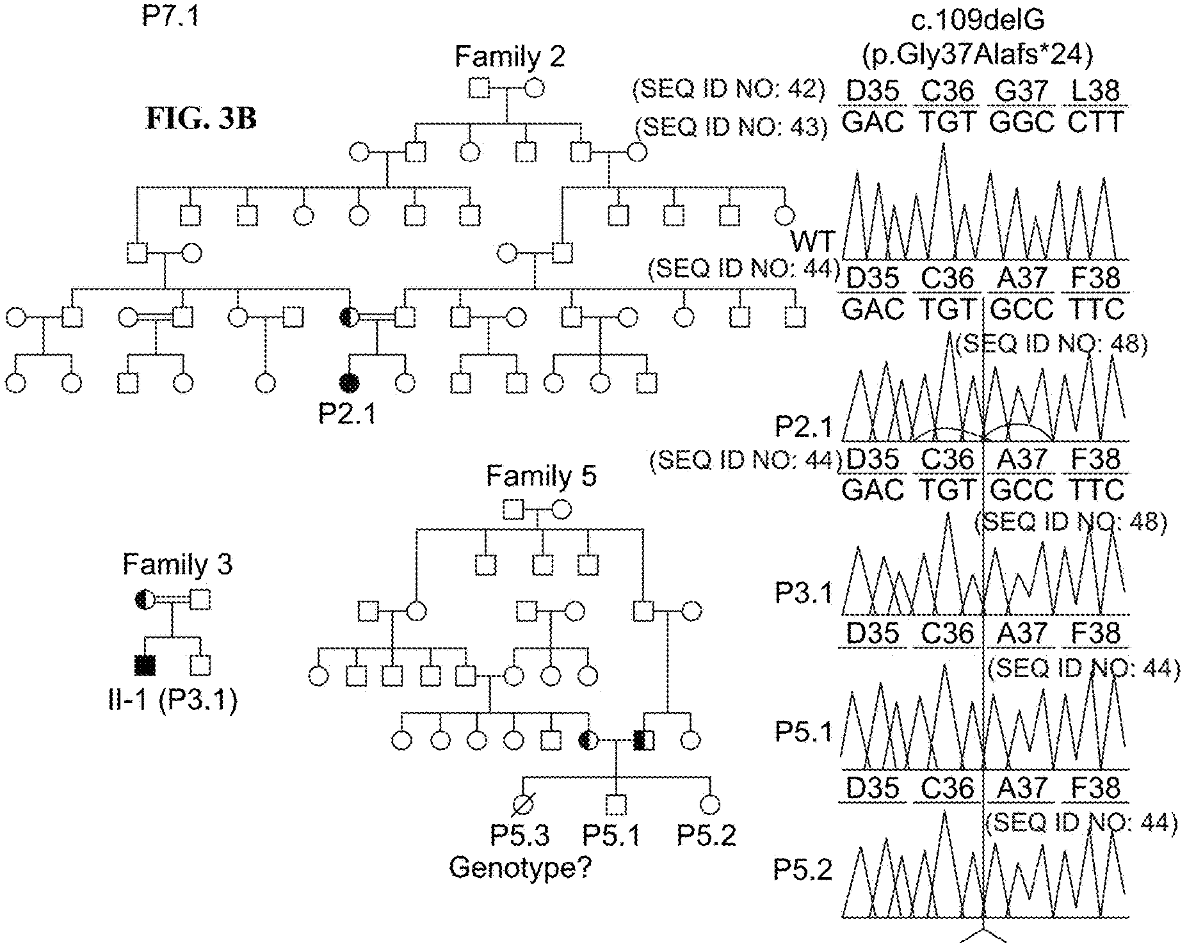
Figure 3C:
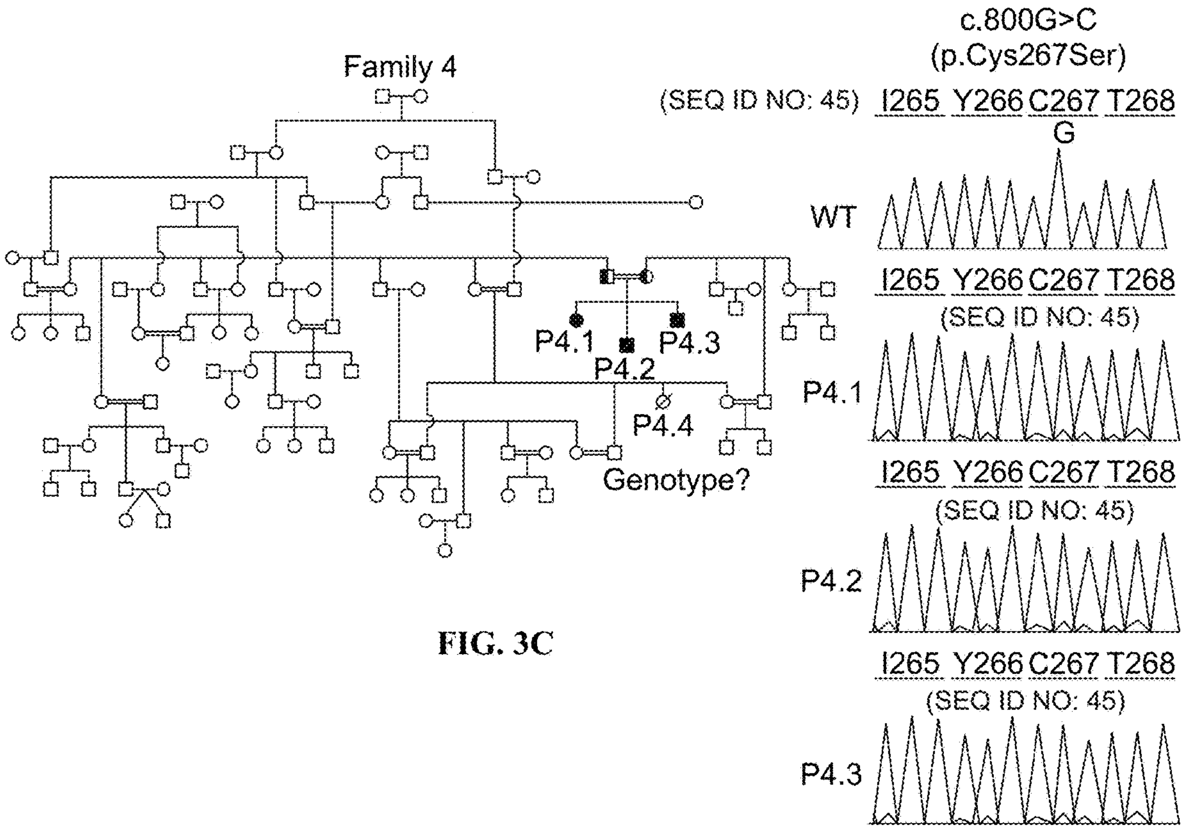
Figure 3D:
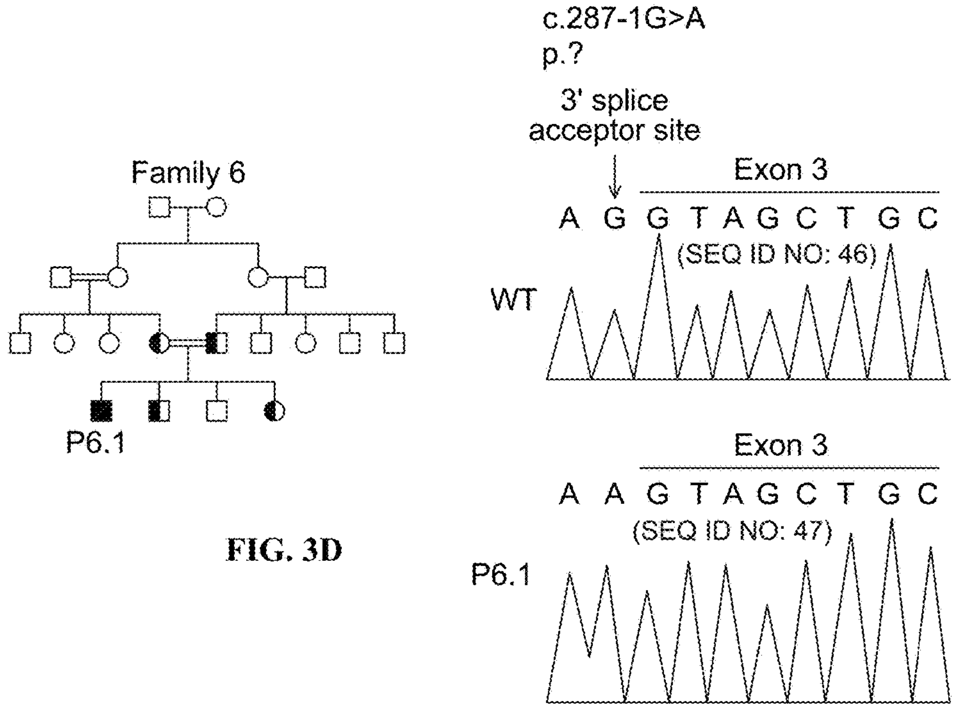

Patient 2.1, a 22-year-old female born to consanguineous Turkish parents, presented with fever, productive coughing and hemoptysis at the age of 6 years when she was diagnosed with pneumonia. She continued to have recurring respiratory symptoms with breathing difficulty, wheezing, chronic coughing, and multiple attacks of pneumonia leading to the development of bronchiectasis and finger clubbing. Following the onset of respiratory illness, she developed GI complaints, with abdominal pain and distention, diarrhea, and, eventually, cessation of growth. Clinical presentation included vomiting, diarrhea, periorbital and pretibial edema and she was found to have hypoalbuminemia and decreased serum levels of Vitamin B12, folate, iron, and hypothyroxinemia. When she was 11 years old her serum immunoglobulins levels were determined due to suspected immunodeficiency. These tests revealed hypogammaglobulinemia and she was started on IVIG replacement therapy. While on IVIG the frequency of infections decreased substantially, leading to the recovery of bronchiectasis. Despite IVIG, serum immunoglobulin G levels remained within the lower range and correlated with the serum albumin levels over time, suggesting the loss of immunoglobulins through the GI tract (FIG. 1B). In order to assess the patient's capacity to produce specific antibodies, we evaluated isohemaglutinin titers and antibody response to pneumococcal vaccine, with normal results. After several years of loss to follow up, she presented to the gastroenterology clinic with persisting symptoms and received treatment for IBD. Despite treatment, she experienced symptoms of intestinal obstruction at the age of 22 years and underwent surgery for the resection of the narrowed intestinal segment (FIG. 1H). The resection material showed fissuring ulcers, cryptitis and crypt abscesses, villous blunting, diffuse epithelial regeneration, and dramatic lymphangiectasis.

Patient 3.1, a 16-year-old boy born to consanguineous Turkish parents, presented with edema due to hypoalbuminemia at 27 months of age. Serial colonoscopies revealed progressive macroscopic hyperemic lesions with ulcers, cryptitis, crypt abcess, and lymphoid cell infiltration that did not respond to steroids and azathioprine treatment alone. Over time, addition of mesalazine to treat IBD and supplementation therapy with calcium, vitamin B12 and folic acid led to clinical improvement. Of note, the patient did not present with classical VEO-IBD symptoms such as bloody stools at the beginning of the disease. The patient presented with protein losing enteropathy with hypoalbuminemia and serial serum immunoglobulin investigation revealed reduced levels of IgG. Lymphocyte counts were also reported as normal. This patient has not, as of yet, presented with recurrent/severe lower respiratory tract infections despite hypogammaglobulinemia. In addition, no infectious trigger was found throughout GI episodes indicated by normal C-reactive protein (C-RP) levels, as well as a normal erythrocyte sedimentation rate (ESR).

Patient 4.1, a 3-year-old girl born to consanguineous parents, presented with puffy eyes, diarrhea and vomiting at 1 year of age. She continued to have recurrent episodes of periorbital and pretibial edema, mostly triggered by the bouts of bloody and mucous diarrhea. She was found to have persistent hypoalbuminemia, for which she received intermittent albumin infusions. Evaluation for other serum proteins revealed hypogammaglobulinemia, with low IgG, IgA and IgM levels. At presentation, anthropometric indices revealed wasting with weight within the $3^{rd}$ to $10^{th}$ percentile and height within the $50^{th}$ percentile for her age. The patient currently receives supplementation therapy for the deficiency of vitamin B12. Despite low immunoglobulin levels she has not experienced any significant or recurrent infections as of yet. Evaluation for infectious etiology during attacks of diarrhea and vomiting proved negative, along with normal levels of inflammatory markers such as C-reactive protein (CRP) and erythrocyte sedimentation rate (ESR). Evaluation for the differential diagnoses including food allergy and cystic fibrosis or celiac disease was also negative.

Patient 4.2, a 17 year-old boy and brother of Patient 4.1 and 4.3, has a history of occasional and self-limiting presentations with facial and extremity edema, for which no medical intervention was required. Despite testing positive for hypogammaglobulinemia, he denied any history of infections of unusual severity or frequency. The patient has not experienced any significant GI symptoms thus far.

Patient 4.3, an 18-year-old boy and brother of patient 4.1 and 4.2, has been mostly asymptomatic. Laboratory evaluation revealed low-normal levels of serum proteins and vitamin B12. The patient has not experienced any significant GI symptoms thus far, and has not reported any history of edema.

Patient 4.4 was an affected female cousin of patients 4.1-4.3 with an unknown genotype. Clinically, this patient presented with recurrent facial and extremity edema, chronic bloody diarrhea, chronic malnutrition, low serum protein levels, with hypoalbuminemia (albumin: 1.9 g/dl) and hypogammaglobulinemia. Histopathology revealed the presence of dramatic lymphangiectasis in the small intestine. The patient was treated with immunosuppressive treatment including steroids and azathioprine due to suspected IBD. Interestingly, she had a history of thrombosis and cerebral vascular disease with hypodense brain lesion in the lateral ventricule and received anticoagulation therapy with low molecular weight heparin. Angiographic studies demonstrated various vascular pathologies at the intra-abdominal and cerebral vessels including: (1) narrowed superior mesenteric vein with multiple collateral veins, suggestive of chronic thrombosis, and (2) decreased blood flow in internal carotid arteries, particularly in cavernous and intracranial segments and undetectable middle cerebral artery. She eventually developed an intestinal obstruction and underwent intestinal resection surgery to remove the narrow segments. Histopathological evaluation of the resection material revealed lymphangiectasia, a focus of ulceration, and abundant ectatic vascular elements with vessel wall thickening. At 33 years of age, this patient died of thrombosis, cardiac arrhythmia, and respiratory distress syndrome developing after surgical resection to remove a severe intestinal obstruction. We were unable to successfully obtain a genetic analysis of this patient due to not having access to patient tissue.

Patient 5.1 is a 10-year-old boy and the sibling of Patient 5.2 born to consanguineous Turkish parents. The patient was first admitted to a hospital at the age of one year with diarrhea and vomiting. He was diagnosed with intestinal lymphangiectasia with severe hypoproteinemia, with low albumin and immunoglobulin levels. The patient required frequent albumin infusions and was put on a protein rich diet with medium-chain triglyceride (MCT) supplements. At the age of 7 years old, Patient 5.1 underwent abdominal surgery for the resection of lymphangiectatic segments, which led to a temporary recovery of his symptoms. He has had multiple recurrent thrombotic events in mesenteric and hepatic veins, as well as in the vena cava inferior, atrial and ventricular thrombosis. He received anticoagulation treatment with warfarin following cardiac surgery for atrial thrombosis. He also presented with intracranial bleeding and underwent neurosurgical operations. Currently, the patient is prescribed octreotide irregularly. The patient is not reported to have an increased rate of respiratory infection despite low immunoglobulin levels. There was no evidence of gastrointestinal infection, and sweat chloride test, celiac markers, and lipid profiling were normal. Colonic biopsy revealed edema and eosinophilic infiltrates, from which a diagnosis of eosinophilic colitis was made. The patient is in poor condition and requires frequent hospital admissions.

Patient 5.2, is the 12-year-old affected sister of Patient 5.1. The patient presented with frequent abdominal pain, and a similar manifestation of hypogammaglobulinemia and hypoalbuminemia as Patient 5.1, which required frequent albumin transfusions. Due to episodes of intestinal obstruction, she underwent resection of edematous small bowel segments to remove lymphangiectatic segments, upon which she experienced some clinical remission. Of note, this patient did not present with any thrombotic events, infectious history, or bloody diarrhea.

Patient 5.3, an affected sister of patients 5.1 and 5.2 of unknown genotype, was admitted at 15 months old with complains of eyelid and extremity edema and diarrhea. The patient presented with hypoalbuminemia, hypogammaglobulinemia, thrombocytosis and anemia. Endoscopy and histopathological examination of the duodenum revealed intestinal lymphangiectasis. The patient had severe malnutrition, with reduced levels of calcium, magnesium, and phosphorus and various vitamins. The patient was treated with intravenous calcium, albumin, vitamin, and mineral supplements on top of medium chain triglyceride supplements and octreotide. These treatments led to temporary clinical improvement. Small bowel resection was performed three times over a period of 2 years with only transient clinical improvement. Parenteral nutrition efforts were interrupted by *Candida* and *S. Aureus* infections along with sepsis. She developed a thrombus in the vena cava superior leading to vena cava superior syndrome and anti-thrombotic treatment with low molecular weight heparin and tissue plasminogen activator was initiated. The patient developed ascites, pleural effusion, and pulmonary infection and died when she was 4.5 years old.

Patient 6.1, a 15-year-old boy born to consanguineous Turkish parents, presented with facial and extremity edema at 1.5 years of age and was found to have hypoalbuminemia. He had frequent hospital admissions due to vomiting, diarrhea and abdominal pain. Endoscopic examination revealed intestinal lymphangiectasia and he was put on steroid treatment. Evaluation for common causes of secondary lymphangiectasia including heart diseases and abdominal mass lesions was negative. Upon persistence of his symptoms he was started on octreotide treatment and prescribed a diet low in fat and high in high quality protein along with MCT supplements. Along with chronic gastrointestinal symptoms he developed deficiencies in the major micronutrients and vitamins such as iron, calcium, magnesium and vitamin D leading to growth retardation. Frequent exacerbations of facial and extremity edema and abdominal symptoms in relation to severe intestinal wall edema (FIG. 1C) required repeated albumin transfusions. In line with the low albumin levels, serum immunoglobulins were also decreased (Table 2, shown as FIG. 4). Apart from chronic gastrointestinal symptoms he experienced frequent respiratory symptoms with chronic cough and finger clubbing. Computed tomography of the chest revealed fibrotic changes in the posterobasal lung segments. When he was 14 years of age, he suffered severe thrombotic events, with a thrombus originating from a stalk 2 cm distal to the inferior vena cava (IVC) extending into the right atrium, which was impairing the venous blood flow. He also had thrombi in the pulmonary arteries. He underwent thoracic surgery for thrombectomy and was commenced on anticoagulation treatment with low molecular weight heparin and low dose aspirin. Despite prophylactic anticoagulation treatment, during the follow up he experienced recurrence of thrombosis with reformation of the clot in the right atrium. Screening for common congenital hypercoagulable states such as Factor V Leiden or prothrombin G20210A mutations that lead to over activity of coagulation factors, or arising from a deficiency of the natural anticoagulants Protein C, S and anti-thrombin III was negative. The patient was found heterozygous for the thermolabile variant of the methylenetetrahydrofolate reductase (MTHFR) gene, C677T and no A1298C mutation was observed in this gene along with normal plasma homocystein level, suggesting no increased risk of thrombosis attributable to hyperhomocysteinemia. The patient was also tested for anticardiolipin and anti-phospholipid antibodies and for paroxysmal nocturnal hemoglobinuria through Fluorescein-labeled proaerolysin (FLAER) flow cytometry assay, with negative results. The patient currently suffers a debilitating disease with frequent hospital admissions.

Patient 7.1, a 4-year-old girl born to consanguineous Syrian parents, presented with facial and extremity edema at 1 year of age, with continued relapses thereafter. She has experienced recurrent gastrointestinal symptoms, with chronic diarrhea and was found to have hypoalbuminemia. She was diagnosed with suspected intestinal lymphangiectasia and commenced on octreotide treatment. She has growth retardation, with height for age below the 3rd percentile. Due to micronutrient deficiencies she received supplementation therapy with vitamin D, vitamin B12, multivitamins, and was transfused with erythrocyte suspension due to anemia. She was prescribed a diet low in fat and high in high quality proteins, MCT supplements, and further supplementation by enteral feeding and albumin transfusion as required. Measurement of serum immunoglobulins revealed low IgG, IgA and IgM (Table 2). Immunologic evaluation revealed normal isohemaglutinin titers and the proportion of the lymphocyte subsets was within normal limits. She has experienced recurrent lower respiratory infections and received parenteral antibiotics and was put on prophylactic antibiotic treatment with co-trimoxazole.

Clinical Phenotype. Demographic data and the clinical presentations of the 10 patients in the study are shown in Table 2 (FIG. 4), and patient descriptions were described above. Patients 1.1-3.1 were born to unaffected consanguineous parents with a distinct PLE syndrome comprising severe hypoalbuminemia, hypogammaglobulinemia and chronic diarrhea. After gene discovery in these initial cases, additional patients were found by evaluating early-onset PLE patients.

Overall, patients presented with facial and extremity edema accompanied by chronic persistent bloody diarrhea with remissions and exacerbations in disease severity (Table 3). Individual patients had additional disease manifestations, some with multiple thrombotic events and vascular alterations and others having a history of recurrent respiratory infections.

Figure 5A:
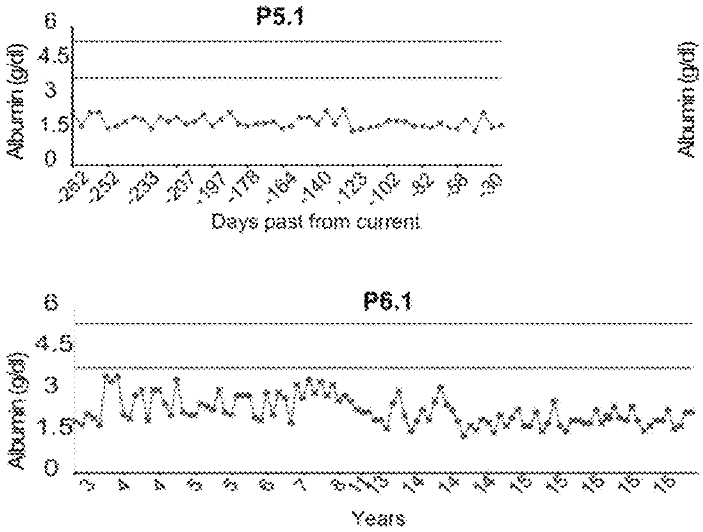
FIGS. 5A, 5B, and 5C. Albumin levels and weight/height curves. Serum albumin levels from P5.1 and 5.2 on a weekly basis and from P6.1 over years. Periodic abrupt rises represent partial albumin restoration following transfusion (A). Height and weight curves for Patients 1.1, 2.1, 6.1, and 7.1 relative to the normal range (B and C). Supplementation therapy with vitamins and dietary intervention led to a variable benefit on patients' growth. Whereas Patient 2.1 was within the third and tenth weight and height percentiles at presentation, she reached the $25^{th}$ and $50^{th}$ percentiles for weight and height, respectively. On the other hand Patient 1.1 had only partial recovery, with persistent stunting despite weight gain. Patient 6.1 demonstrated significant growth retardation, worsening after age 14 when the patient developed severe thrombosis. Patient 7.1 has a current height for age value below $3^{rd}$ percentile.

All patients exhibited persistent hypoproteinemia, with reductions both in albumin and gammaglobulins (FIG. 1B and FIG. 5A). The degree of hypoproteinemia and the severity of symptoms varied among individual cases. Patients 4.2 and 4.3 had mild disease with occasional facial and extremity edema whereas others had profound hypoalbuminemia and a severe progressive disease course (Table 2). Radiological exams, taken from patients in the presence of acute GI symptoms, showed that the patients had bowel wall edema/thickening (FIG. 1C, arrows) sometimes together with partial intestinal obstruction, which responded favorably to albumin replacement therapy. The hypoproteinemia was attributed to GI protein loss because the nadir of albumin levels correlated with the flares of bloody and mucous diarrhea and increased excretion of $\alpha$-1 antitrypsin was detected in feces in Patient 1.1. Other causes of hypoproteinemia, including hepatic disease, decreased nutritional intake, or heavy proteinuria, were excluded in all cases. Endoscopic evaluation revealed relatively mild alterations in the mucosa given the severity of protein loss, whereas histopathology of small intestinal biopsies demonstrated dilatation of the lacteals and distension of the lymphatic vessels in Patients 2.1, 5.1, 5.2, 6.1 and 7.1 (Table 2, FIG. 1D). Evaluation for common systemic conditions that could lead to secondary lymphangiectasia, such as cancer, heart disease or obstructive lesions involving the lymphatic system, was negative, indicating a diagnosis of primary intestinal lymphangiectasia as the cause of PLE. Surgical removal of the localized lymphangiectatic segments in Patients 5.1 and 5.2 resulted in substantial, but temporary, reversal of PLE in the case of Patient 5.1, and symptom alleviation in the case of Patient 5.2.

Figure 5B:
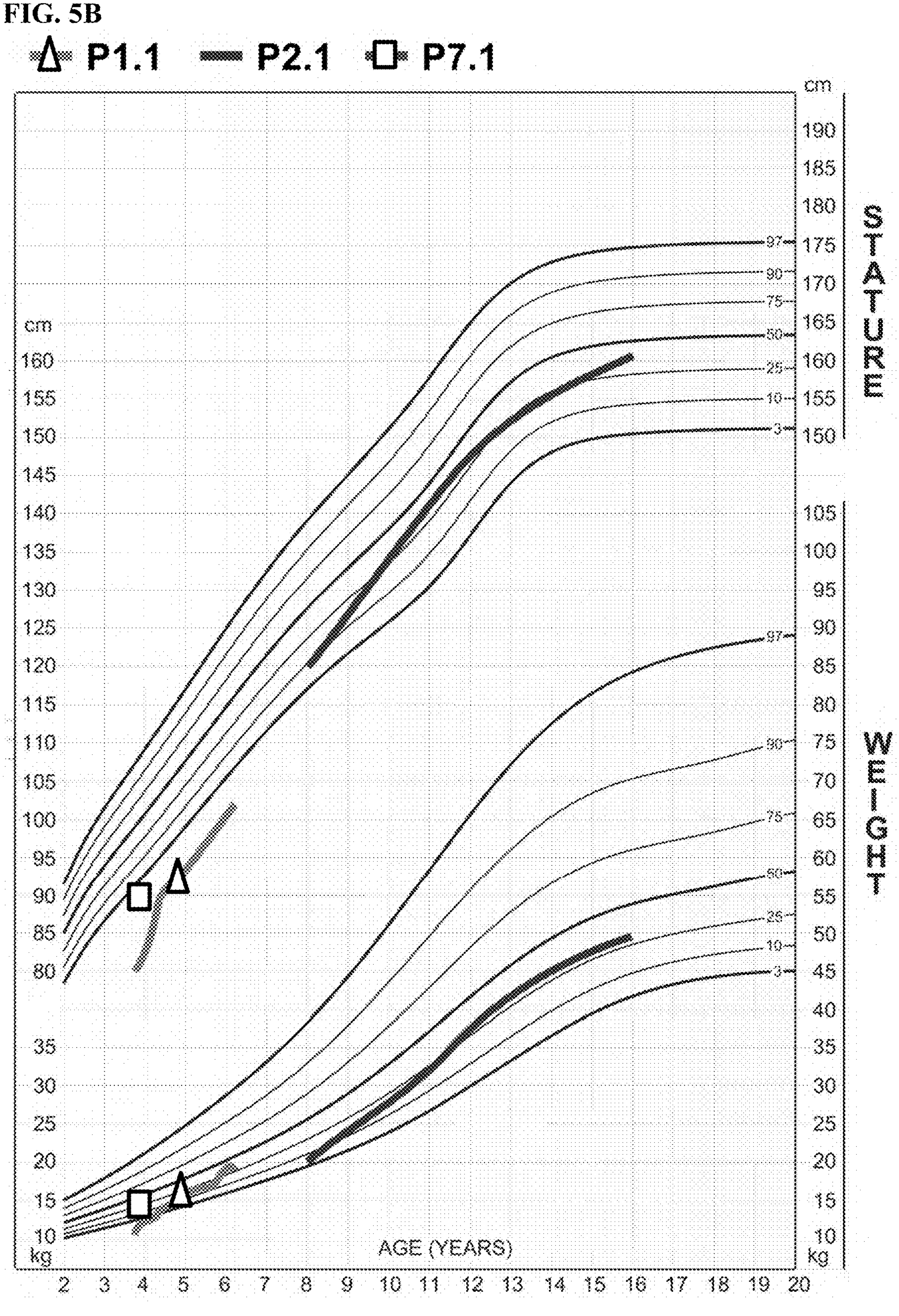
Figure 5C:
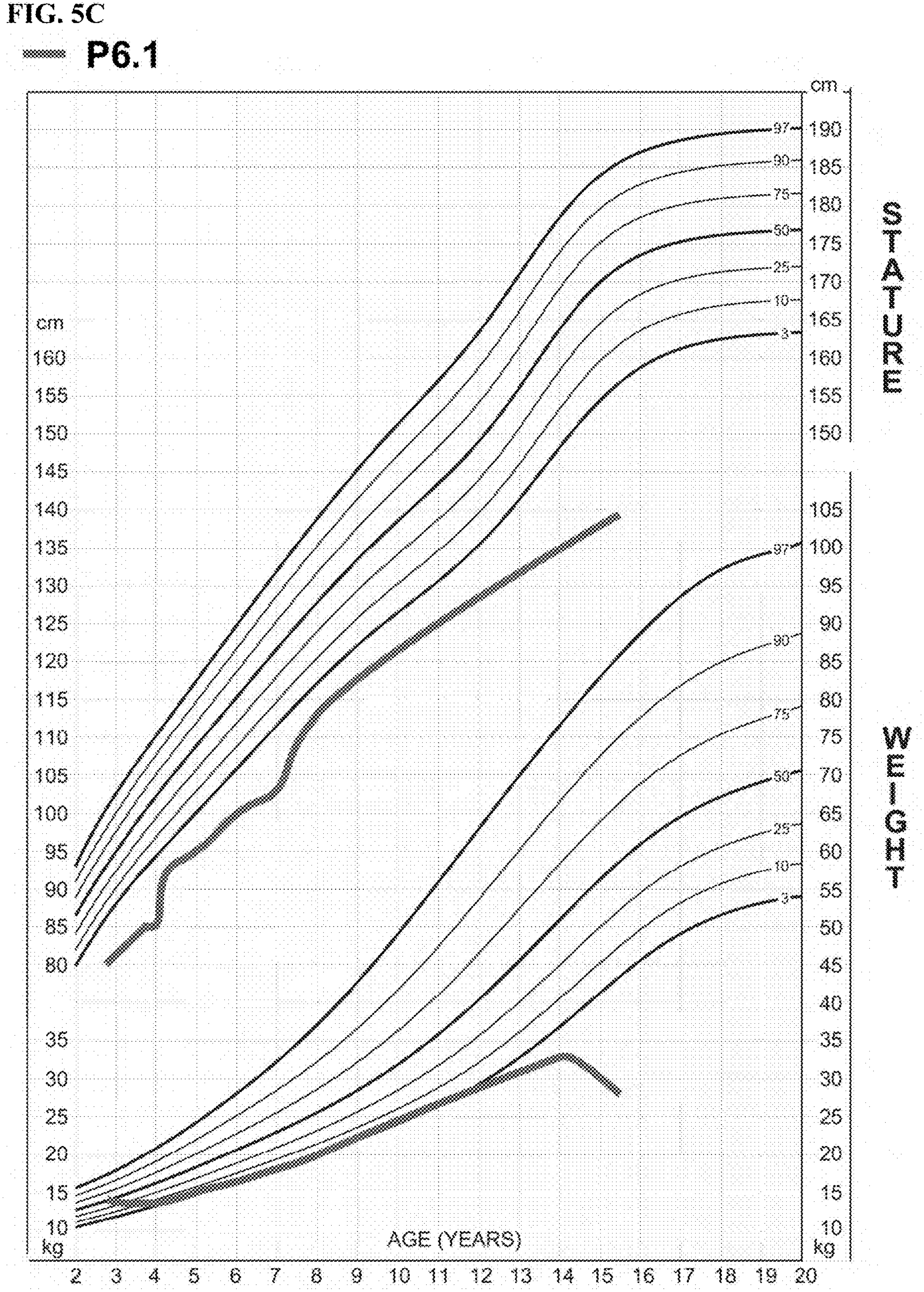

The patients eventually developed an intestinal malabsorption syndrome, with anemia and major micronutrients deficiencies including iron, calcium, magnesium, folate and vitamins D and B12, ultimately leading to retarded growth (Table 2 and FIGS. 5B and 5C). Supplementation therapy with vitamins and micronutrients along with dietary modification and albumin and blood transfusions as required led to improved growth in some of the patients, whereas others had a more refractory course with progressive malnutrition (FIG. 5).

Some of the patients had hypercoagulability with recurrent thrombosis and vascular alterations. Patient 6.1, who initially had relatively stable GI disease, developed severe thrombotic disease during follow up. Large occlusive thrombi occurred in the inferior vena cava (IVC) and right atrium together with thrombi in the pulmonary arteries (FIG. 1E, left panel), which was accompanied by arteriovenous malformations in the lung (FIG. 1E, center and right panels). Despite surgical removal of blood clots and anticoagulation therapy, continuing thrombosis caused an overall worsening of symptoms. Similarly, Patient 5.1 had multiple thrombotic events in the mesenteric and hepatic veins as well as the right atrium and ventricle, which was treated with low molecular weight heparin anticoagulation. He also had a history of intracranial hemorrhage, which required cranial surgery. Of note, a cousin of Patients 4.1-4.3 and a sibling of Patients 5.1 and 5.2 (FIG. 3), with undetermined genotypes, had a similar course of disease leading to death at 33 and 4.5 years of age respectively. These patients presented with PLE with lymphangiectasia leading to malnutrition, and a history of thrombotic events, which in Patient 4.4 led to cerebral ischemia, mesenteric vein narrowing with development of multiple collateral vessels and histopathologic evidence of ectasia of the vascular elements in the submucosa of the small intestine. Patient 4.4 died of cardiac, thrombotic, and respiratory complications following surgery to remove an intestinal obstruction, while Patient 5.3 died following development of ascites, pleural effusion, and pulmonary infection.

Some of the patients had endoscopic and histopathology features resembling Crohn's disease although without granulomas. Patients 1.1-3.1 showed mucosal ulcers and inflammatory exudate in the terminal ileum and colonic sites (FIG. 1F). In the endoscopic biopsy materials from Patients 1.1, 2.1, and 3.1, there were mixed infiltrates of T and B cells, sometimes with eosinophils (FIG. 1G). Although these three patients received recommended therapy for IBD that reduced their bowel symptoms, a sustained remission was not achieved and GI protein loss continued (Table 2, FIG. 1B, and Figure. 5). Patient 2.1, who recently developed symptoms of intestinal obstruction, underwent surgical resection of a narrowed ileal segment (FIG. 1H) which included dilated lymphatic vessels, leading to resolution of GI symptoms, weight gain and recovery of serum albumin levels during the short term follow up (not shown). None of the patients exhibited extraintestinal manifestations commonly associated with IBD, such as skin eruptions, perianal lesions, fistulas or uveitis.

Patients 1.1, 2.1, 6.1, and 7.1 experienced recurrent respiratory infections in association with hypogammaglobulinemia (Table 2, FIG. 1B (arrows)), while other patients did not report any significant or recurrent infections. As major immunological subsets and specific antibody production were largely normal in the patients (Table 3), it is believe these infections were largely due to loss of serum immunoglobulins. Clinical evaluation of patient peripheral blood immunological subsets of Table 3, provided as either (cells/$mm^3$) or % of total cells. Notably, use of intravenous immunoglobulin (IVIG) replacement therapy decreased the frequency of infections in Patients 1.1 and 2.1 and led to resolution of bronchiectasis in Patient 2.1.

TABLE 3

| Lymphocyte subset characterization in CHAPLE patient peripheral blood | | | | | | | | | | |
|---|---|---|---|---|---|---|---|---|---|---|
| Patient ID | P 1.1 | P 2.1 | P 3.1 | P4.1 | P4.2 | P4.3 | P 5.1 | P 5.2 | P 6.1 | P 7.1 |
| Lymphocyte Subsets (cells/mm$^3$) or % of total cells | | | | | | | | | | |
| CD3$^+$ | 7400 (900-4500) | 2262 (800-3500) | 78% (55-78) | 1552 (900-4500) | 1742 (800-3500) | 1748 (800-3500) | 56% (55-78) | 80% (55-78) | 75% (52-78) | 78% (43-76) |
| CD3$^+$CD4$^+$ | 3630 (500-2400) | 1222 (400-2100) | 28% (27-53) | 994 (500-2400) | 962 (400-2100) | 874 (400-2100) | 27% (27-53) | 44% (27-53) | 49% (25-48) | 37% (23-48) |
| CD3$^+$CD8$^+$ | 3080 (300-1600) | 832 (200-1200) | 39% (19-34) | 534 (300-1600) | 676 (200-1200) | 879 (200-1200) | 24% (19-34) | 21% (19-34) | 28% (9-35) | 37% (14-33) |
| CD19$^+$ | 94 (200-2100) | 156 (100-500) | 24% (10-31) | 378 (200-2100) | 364 (100-500) | 179 (100-500) | 29% (10-31) | 8% (10-(31) | 6% (8-24) | 14% (14-44) |
| CD3$^-$ CD16$^+$/CD56$^+$ | 198 (100-1000) | 78 (90-600) | 12% (4-26) | 120 (100-1000) | 390 (90-600) | 176 (90-600) | 11% (4-26) | 7% (4-26) | 1% (6-27) | 3% (4-23) |

Figure 6A:
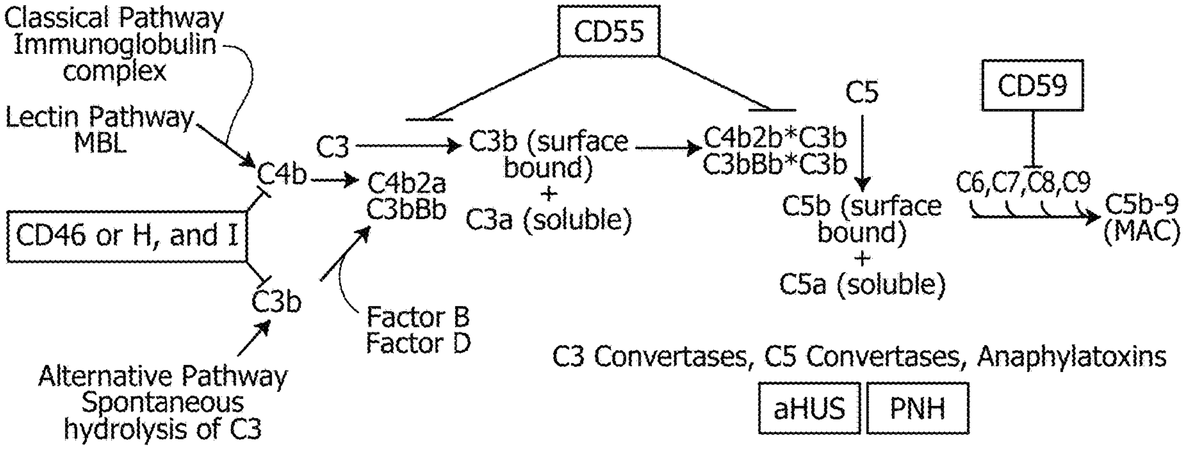
FIGS. 6A, 6B, 6C, 6D, and 6E. Mutations in CD55 lead to loss of protein expression. Schematic of the complement cascade (A). The identified mutations relative to the CD55 protein structure depicting the four short consensus repeat (SCR) domains and exon location (B). QRT-PCR determination of CD55 mRNA in cycling patient $CD4^+$ T cell blasts (C). Flow cytometry histograms of CD55 surface expression on $CD4^+$ T lymphocytes for the patients compared to healthy controls. Gray shaded histogram shows isotype control and the red histogram denotes experimental sample (D). Western blot denoting CD55 expression in activated $CD4^+$ T cells (E).
Figure 6B:
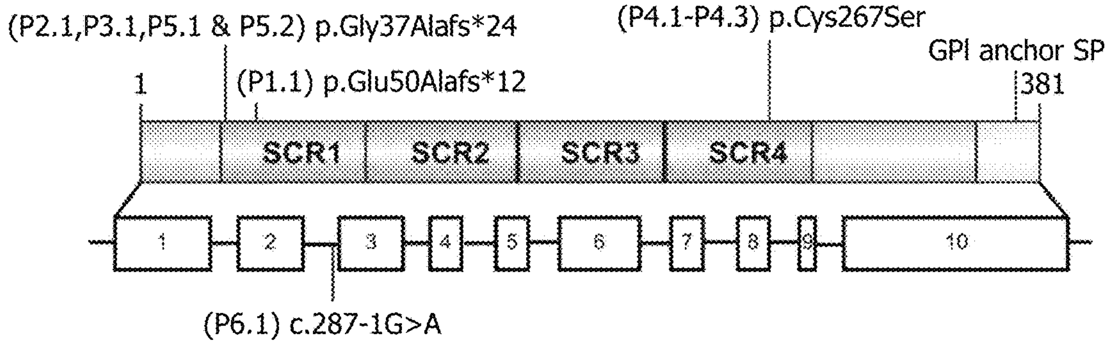

Identification of CD55 mutations. Given the consanguinity in all families under study, an autosomal recessive (AR) mode of inheritance was assumed. WES in Patients 1.1 and 2.1, and combined with homozygosity mapping in Patient 3.1 and 5.1 as described previously (Dobbs K, et al., Inherited DOCK2 Deficiency in Patients with Early-Onset Invasive Infections. The New England Journal of Medicine 2015; 372: 2409-22), revealed potentially deleterious homozygous loss-of-function (LOF) mutations in CD55/Decay Accelerating Factor (DAF), showing perfect segregation under assumption of AR inheritance. CD55 is a negative regulator of the complement cascade ubiquitously expressed on the surface of eukaryotic cells (FIG. 6A). The CD55 nucleotide variants were confirmed by Sanger DNA sequencing (FIG. 3). Additional patients were then screened with a diagnosis of PLE and identified 5 additional patients from Families 4, 6, and 7 with rare biallelic CD55 LOF nucleotide variants. Patient 1.1 and 7.1 were homozygous for dinucleotide deletion and 4 nucleotide insertions at position c.149-150 and patients 2.1, 3.1, 5.1 and 5.2 were homozygous for a single base pair deletion at position c.109, each resulting in frameshift and premature termination codons in CD55. In Family 4, a novel homozygous missense mutation was identified (c.800G>C) in CD55 resulting in a single amino acid substitution (p.Cys267Ser) in the 4th short consensus repeat (SCR) domain, predicted by computational analyses to be deleterious. In Family 6, a mutation was found in the splice acceptor site of exon 3. The locations of the identified mutations within the CD55 protein/gene are depicted in FIG. 6B, and deleterious predictions are shown in Table 4. Mutation and impact score of Table 4 were calculated from indicated predictive algorithm (either the SIFT, Polyphen2 and CADD algorithms). This scoring system was not applicable (N/A) to frameshift or splice site mutations present in majority of our patients. Predictions were based on a reference sequence from ENST00000367064, GRCh37. Altogether, we identified 4 distinct homozygous, novel rare mutations in CD55 in a total of 11 patients of Turkish (2 with unknown genotype), and 1 of Syrian origin (FIG. 6B).

TABLE 4

| Predicted impact scored for identified CD55 varients | | | | | |
|---|---|---|---|---|---|
| Mutation | Chromosome | Position | SIFT | Polyphen2 | CADD |
| c.149_150delAAinsCCTT | 1 | 207495774 | N/A | N/A | 5.585 |
| c.109delC | 1 | 207495734 | N/A | N/A | 12.37 |
| c.800G > C | 1 | 207504588 | 0 (deleterious) | 0.99 (probably damaging) | 23.1 |
| c. 287-1G > A | 1 | 207497903 | N/A | N/A | 23.9 |

Figure 6C:
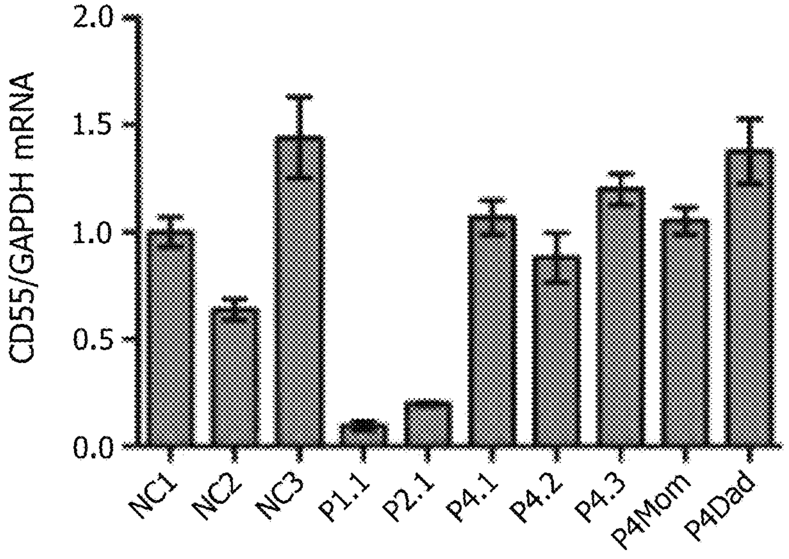
Figure 6D:
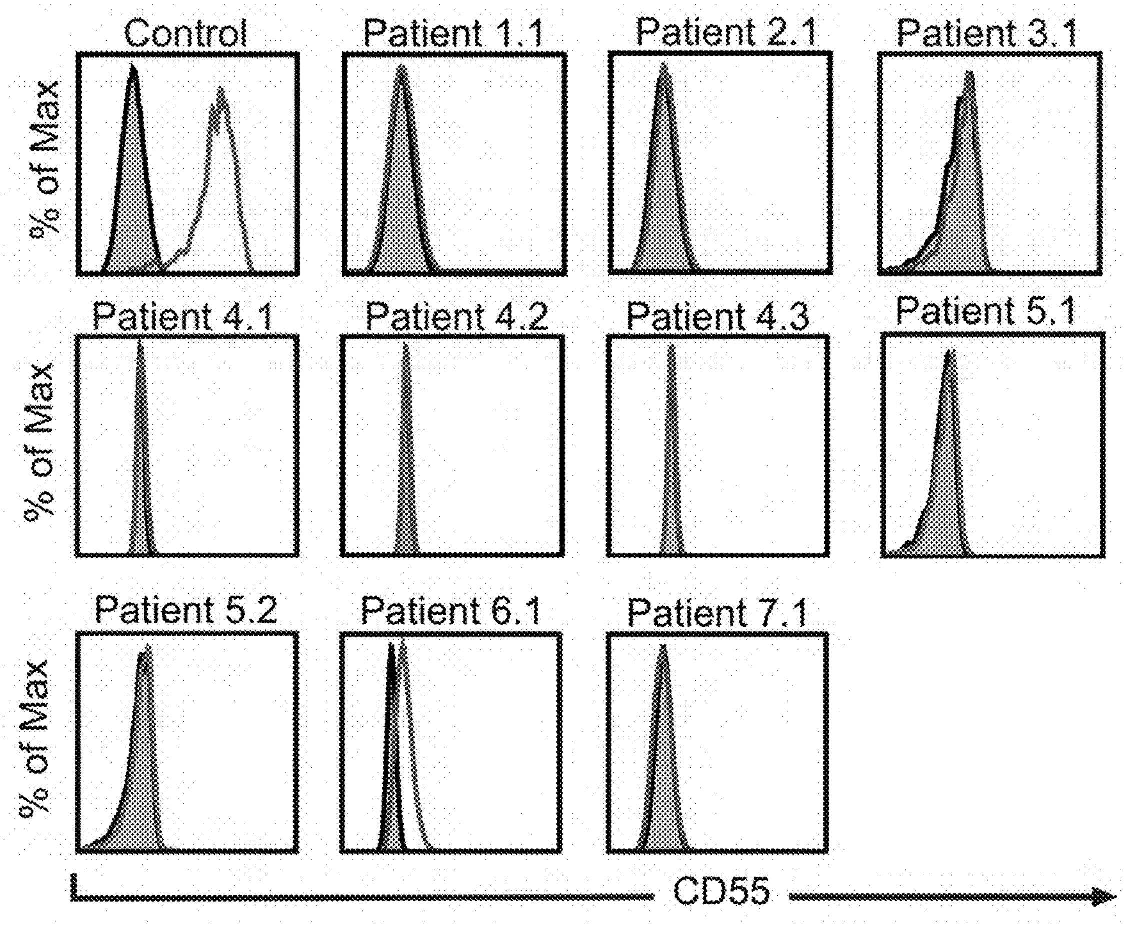
Figure 6E:
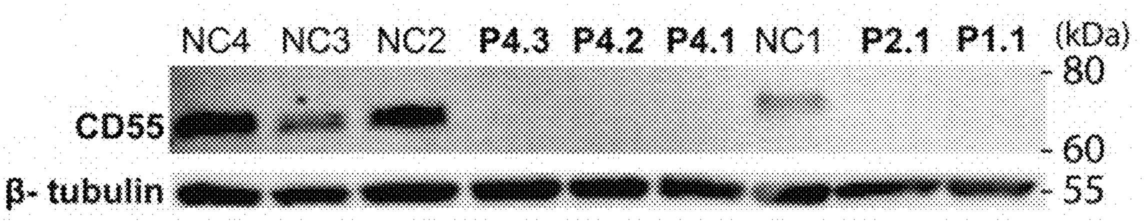
Figure 7A:
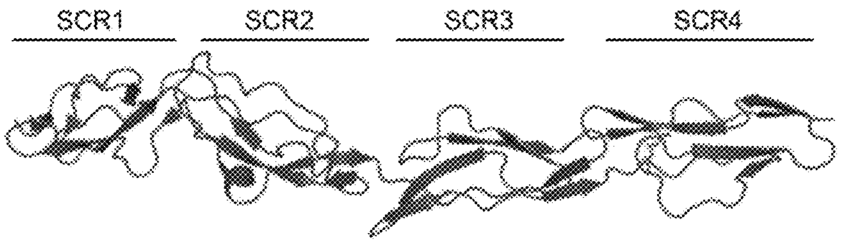
FIGS. 7A and 7B. 3D structure of CD55 showing mutation in Family 4 Location of the mutation in Family 4 within the crystal structure of CD55 (A). Close up of the affected disulfide bond in SCR4 of CD55 (B).
Figure 7B:
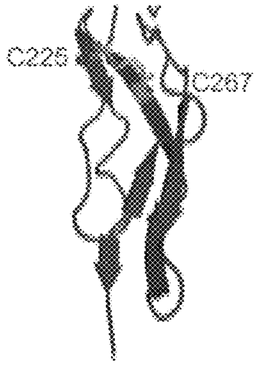

Effects of CD55 Mutations on Messenger RNA and Protein Expression. Patients 1.1, 2.1, 3.1, 5.1, and 5.2 harbored frameshift mutations that led to nonsense-mediated loss of mRNA in 1.1 and 2.1 (FIG. 6C). The mutation present in Patients 4.1, 4.2, and 4.3 is a missense mutation (p.Cys267Ser) that does not alter mRNA expression level (FIG. 6C). Cys267 participates in an intrachain disulfide bond with Cys225 and loss of this bond could lead to CD55 protein misfolding and degradation (FIGS. 7A and 7B) (Nakano Y, et al. Complete Determination of disulfide bonds localized within the short consensus repeat units of decay accelerating factor (CD55 antigen). Biochim Biophys Acta 1992; 1116: 235-40). Absent, or severely reduced, CD55 surface expression was observed by flow cytometry or western blot in all patients (FIGS. 6D and 6E). Patient 6.1, harboring a splice acceptor site mutation, is the only patient with residual protein expression by flow, possibly suggesting exon skipping.

Figure 8A:
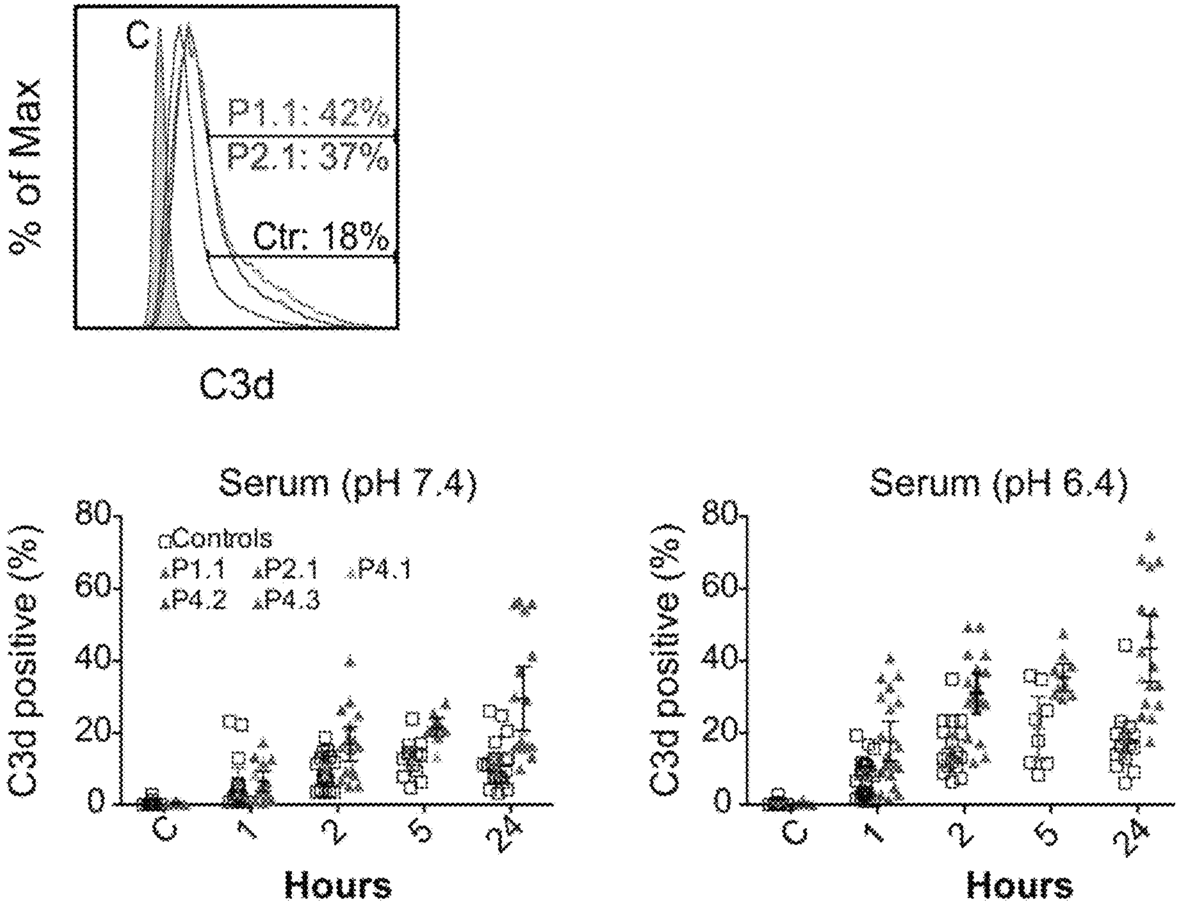
FIG. 8A, 8B, 8C, 8D, 8E. Loss of CD55 leads to spontaneous complement activation by the alternative pathway. Representative flow cytometry plots of C3d deposition on the surface of $CD4^+$ T cell blasts from P1 and P2 (A, left). Pooled analyses of C3d deposition on T cells of five CD55 deficient patients after incubation with normal or acidified (pH 6.4) media containing pooled nHS (A, right). Patient $CD4^+$ T cells were transduced with either wild type (WT) CD55 or Thy1.1 expressing lentivirus (B, top). CD55 or Thy1.1 transduced cells were incubated with acidified normal human serum and the deposition of C3d determined and plotted for the CD55 positive and negative fractions or the Thy1.1 positive or negative fractions (B, bottom left and right, respectively). CD55 expression in a CD55-deficient Jurkat cell line (C, left). C3d deposition on CD55 knock out Jurkat T cells treated with acidified nHS for the indicated amount of time. Knockout cells were a mixture of cells that had been deleted by CRISPR technology and cells that had not been. CD55 positive and negative cells were assessed for C3d deposition within this mixed population (C, right). C3d deposition on HT29 cells with CD55 knocked down using two different shRNAs. Correlation between the geometric MFI values of C3d and CD55 was assessed on scatter plot graphs. Samples were color coded as; Red: Sh-1 CD55, blue: Sh-2 CD55, green: Mock. Circles: No TNF-α pretreatment, Squares: pre-treated with TNF-α. Samples treated with acidified serum are illustrated with solid symbols and corresponding samples treated with control serum are represented with open symbols (D). C3d deposition by live/dead staining for control and patient T cells (D, left) and quantification of C3d deposition and annexin-V/live/dead staining (E).
Figure 8B:
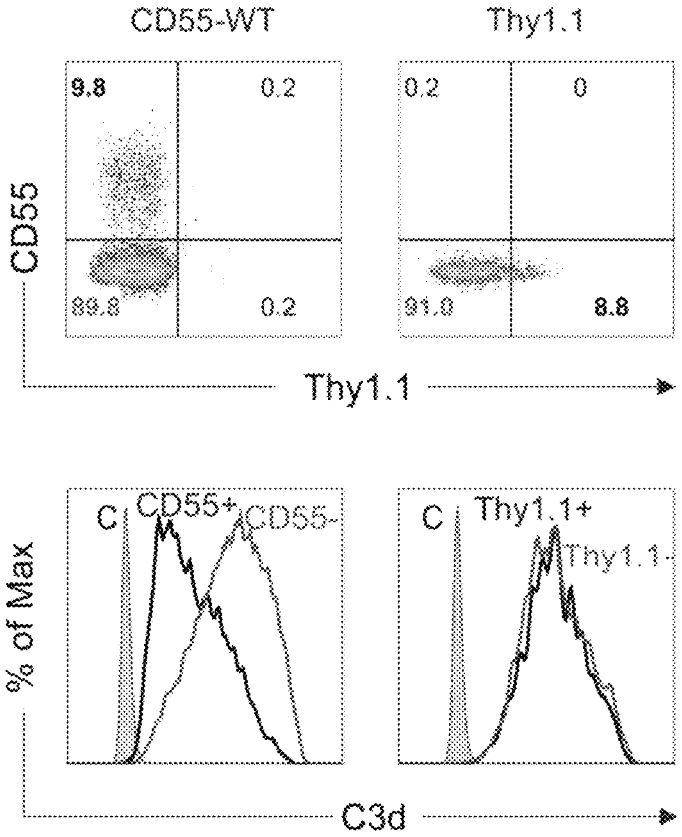
Figure 8C:
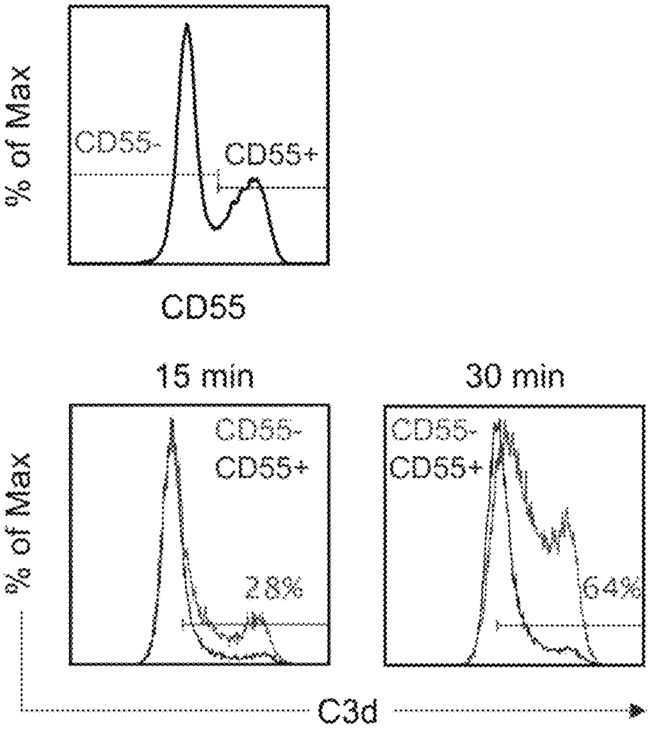
Figure 8D:
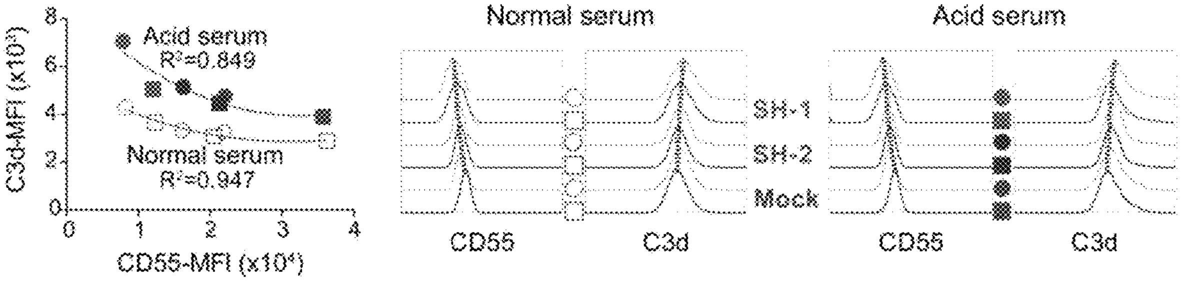
Figure 8E:
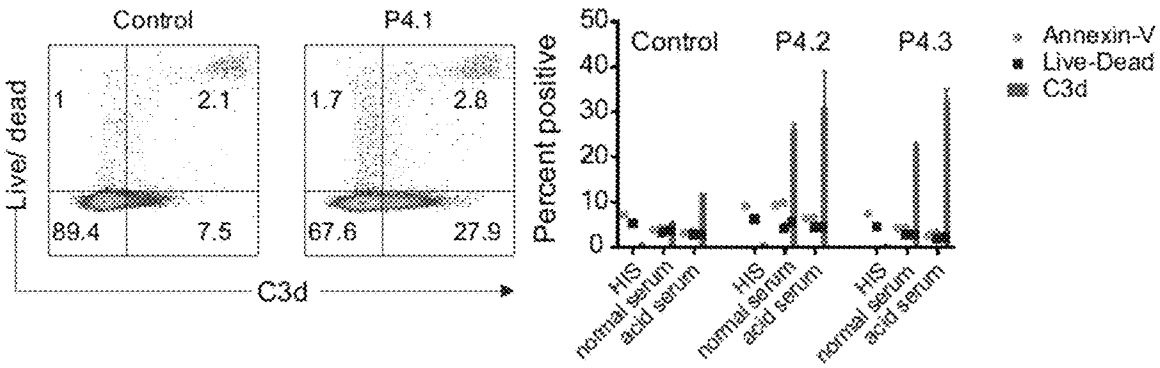

Increased Complement Deposition on CD55-deficient Cells. As CD55 is a negative regulator of the complement pathway, it was hypothesized that CD55 deficiency would lead to increased C3 cleavage and deposition on host cells. Activation of the alternative pathway, marked by C3 cleavage, can be enhanced by serum acidification, used previously for the diagnosis of paroxysmal nocturnal hemoglobinuria (PNH) (Ham T H, et al., Studies on Destruction of Red blood Cells. Li. Chronic Hemolytic Anemia with Paroxysmal Nocturnal Hemoglobinuria: Certain Immunological Aspects of the Hemolytic Mechanism with Special Reference to Serum Complement. J. Clin Invest 1939: 18: 657-72). Hence, control CD4$^+$ T-cell blasts, which highly express CD55 on their cell surface (FIG. 6D), were compared with those from patients after incubation with normal or acidified pooled normal human serum (nHS), both of which caused surface deposition of the complement split product C3d. We observed that C3d was deposited to a greater degree on T cells from multiple patients compared to controls (FIG. 8A). Increased complement activation was due to loss of CD55 as lentiviral transduction of patient T-cell blasts with CD55 protected them from complement deposition (FIG. 8B). The finding was verified on Jurkat T cells, which also constitutively express cell surface CD55, after CRISPR-mediated deletion of the CD55 gene. Increased C3d deposition was observed in the genetically deficient (CD55−) compared to CD55-expressing (CD55+) Jurkat cells (FIG. 8C). C3b (not shown) was unable to detect, suggesting that deposited C3b is rapidly degraded, possibly by serum factor I and the cofactor CD46 or factor H (FIG. 6A). It is known that human intestinal epithelial cells (IECs) express CD55, and that it is upregulated upon TNFα treatment. Thus, it was hypothesized that it may protect IECs from complement activation and damage by anaphylatoxin signaling or direct attack of the terminal complement cascade. We therefore knocked down CD55 in the human IEC line HT29 using lentiviral shRNA transduction and found that this permitted increased C3d deposition. Using various conditions, it was found that the CD55 mean fluorescent intensity (MFI) was inversely correlated with C3d staining indicating that as the level of surface CD55 decreases, the activation of complement increases (FIG. 8D). In all cell types tested, lack of CD55 in patient cells led to increased complement deposition, however, serum/complement-mediated cell death was not observed (FIG. 8E), suggesting that CD55-deficient cells allow early steps in complement activation to occur, but this does not progress to terminal formation of the "membrane attack complex" (MAC).

Figure 9A:
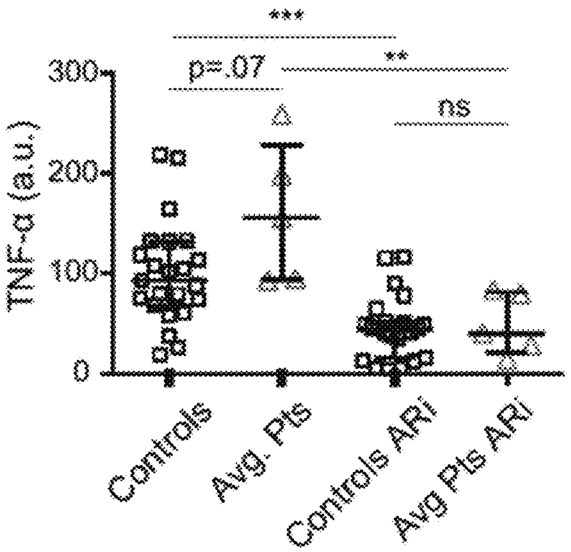
Figure 9B:
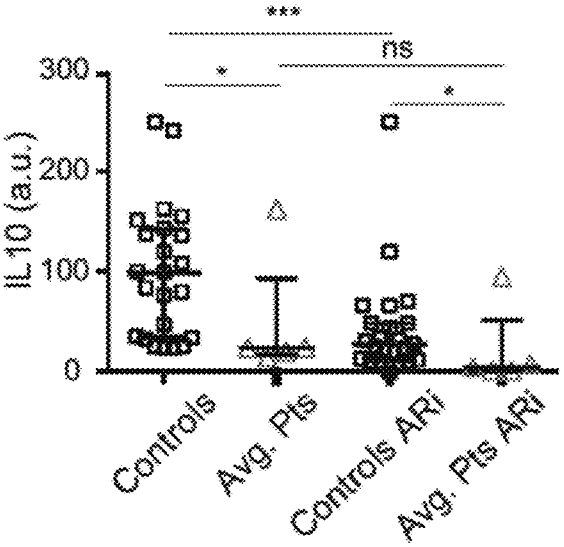
Figure 9C:
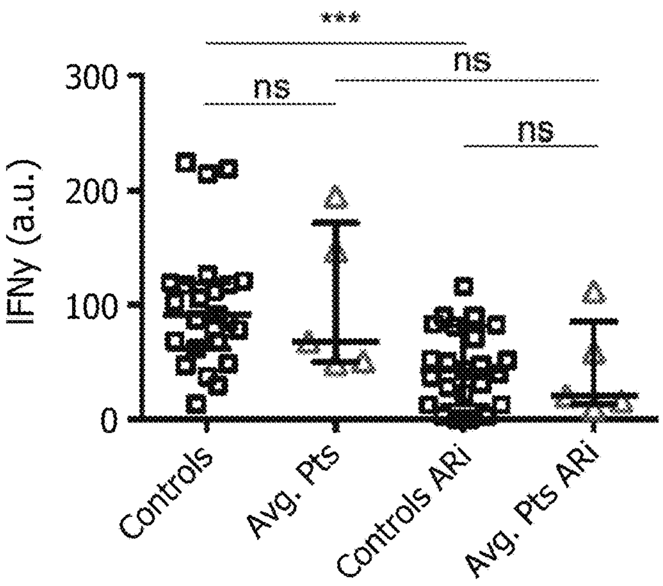
Figure 9F:
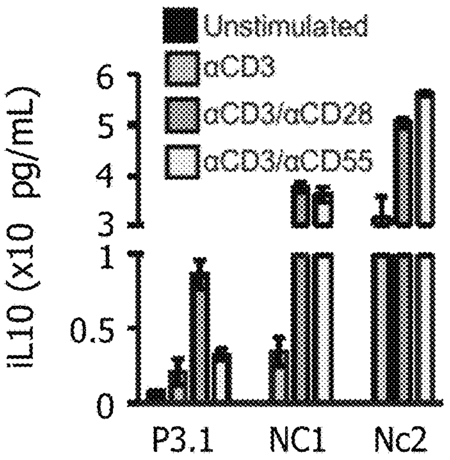
Figure 9D:
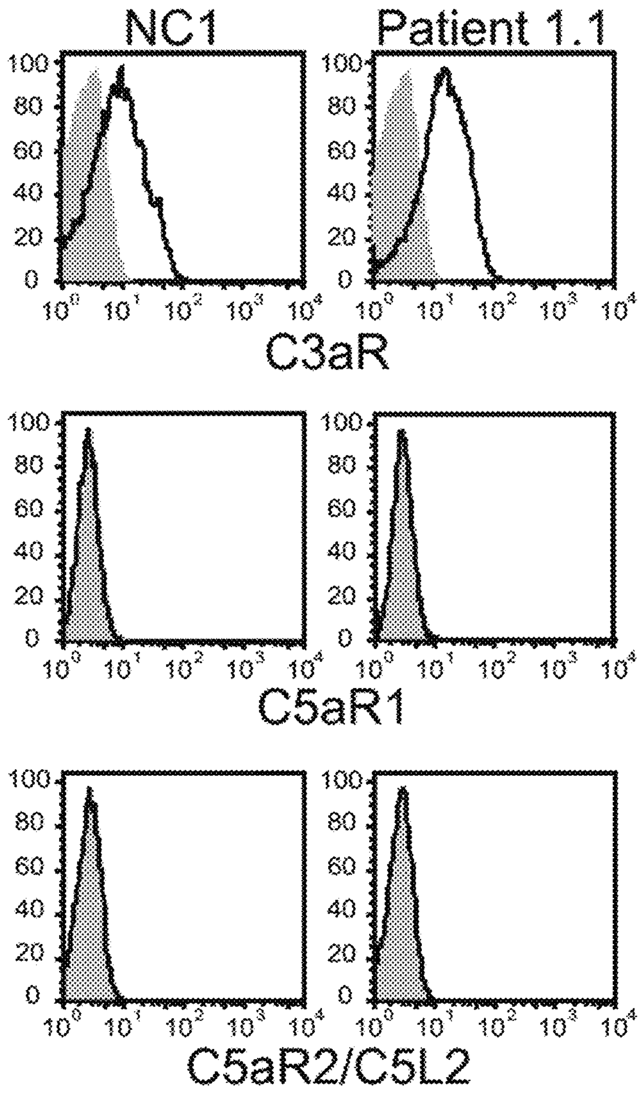
Figure 9H:
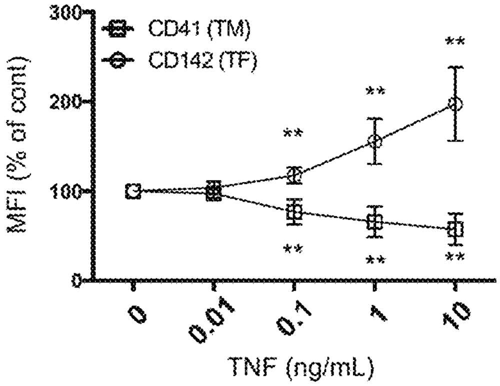
Figure 9J:
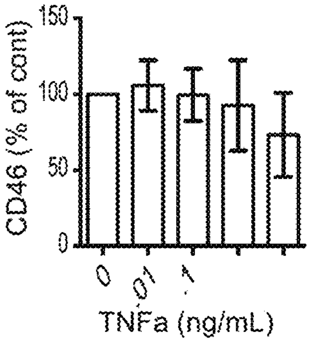
Figure 9K:
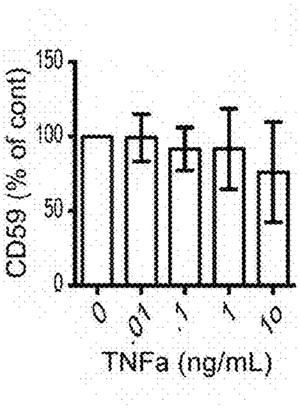
Figure 9L:
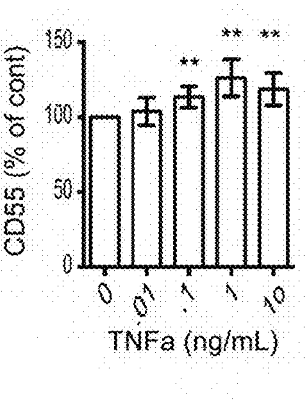
Figure 9E:
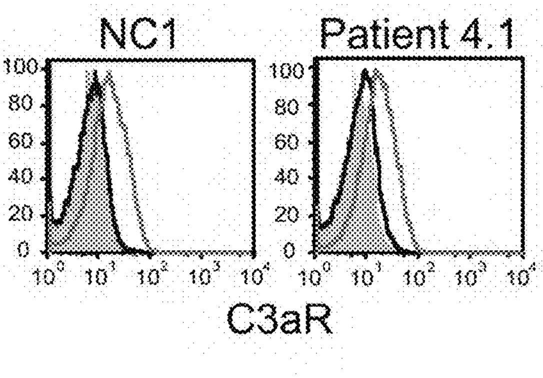
Figure 9M:
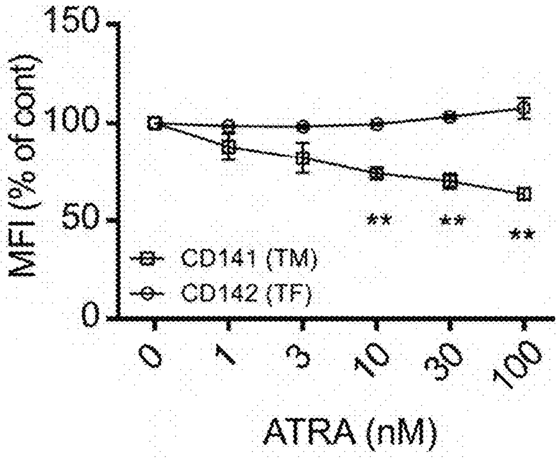
Figure 9N:
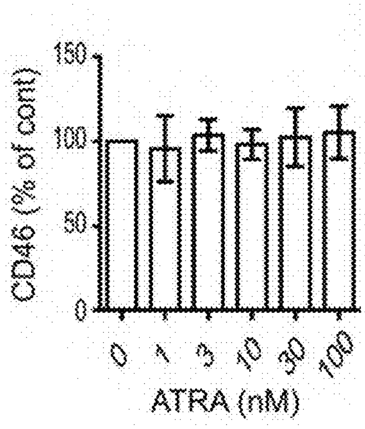
Figure 9O:
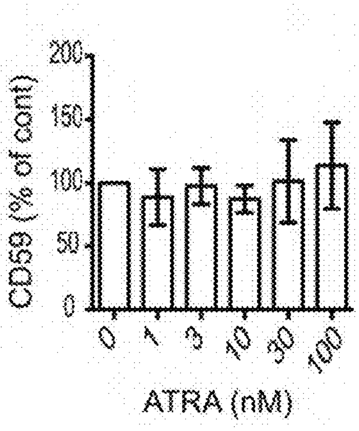
Figure 9P:
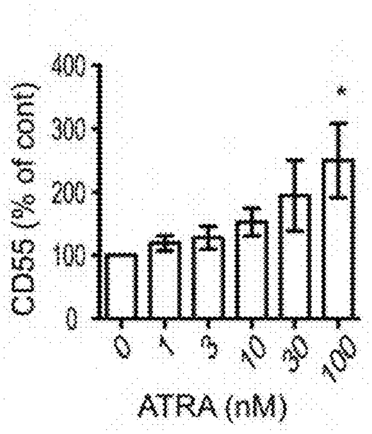
Figure 9I:
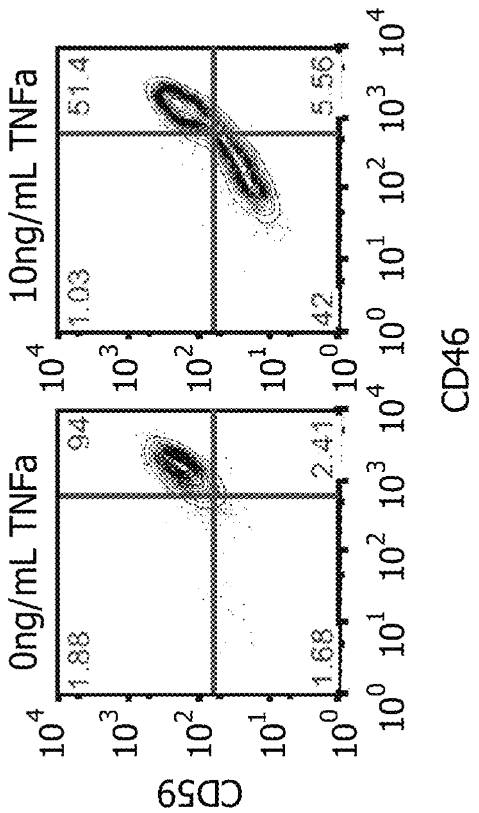
Figure 10A:
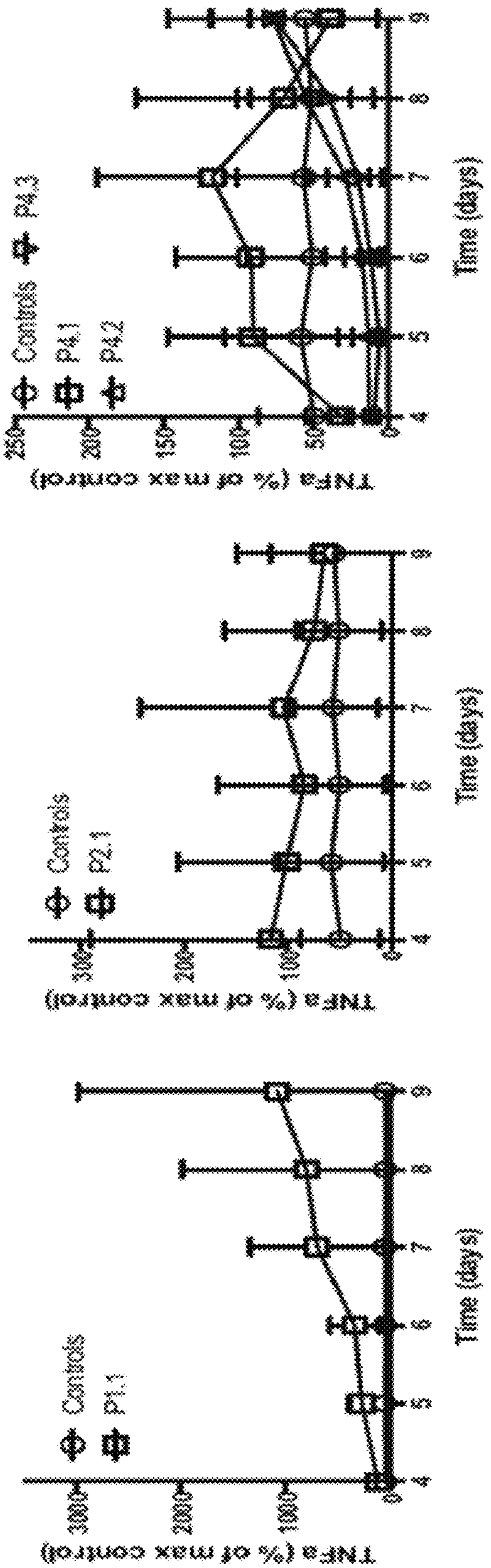
Figure 10B:
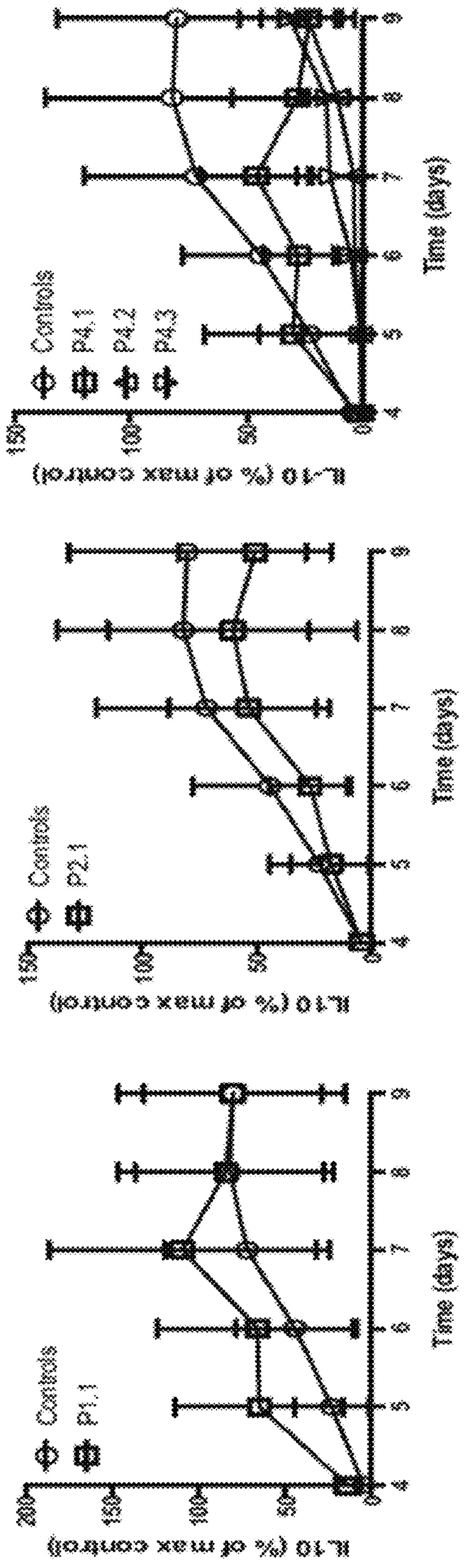
Figure 10C:
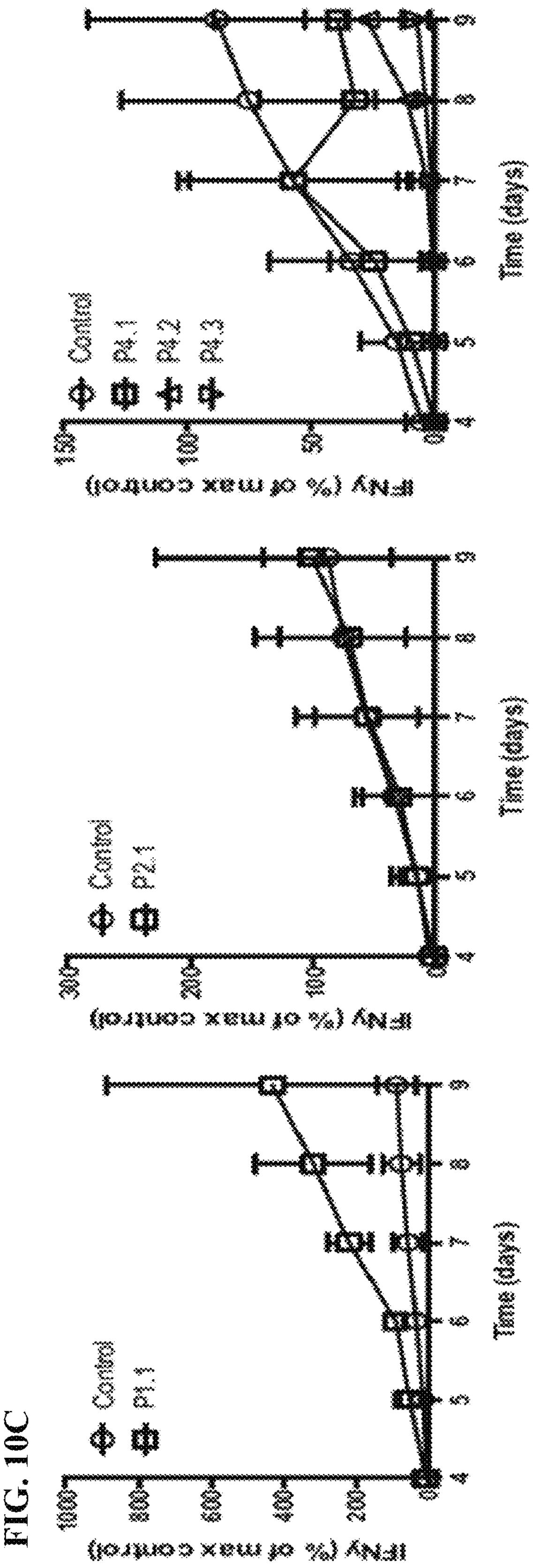
Figure 10D:
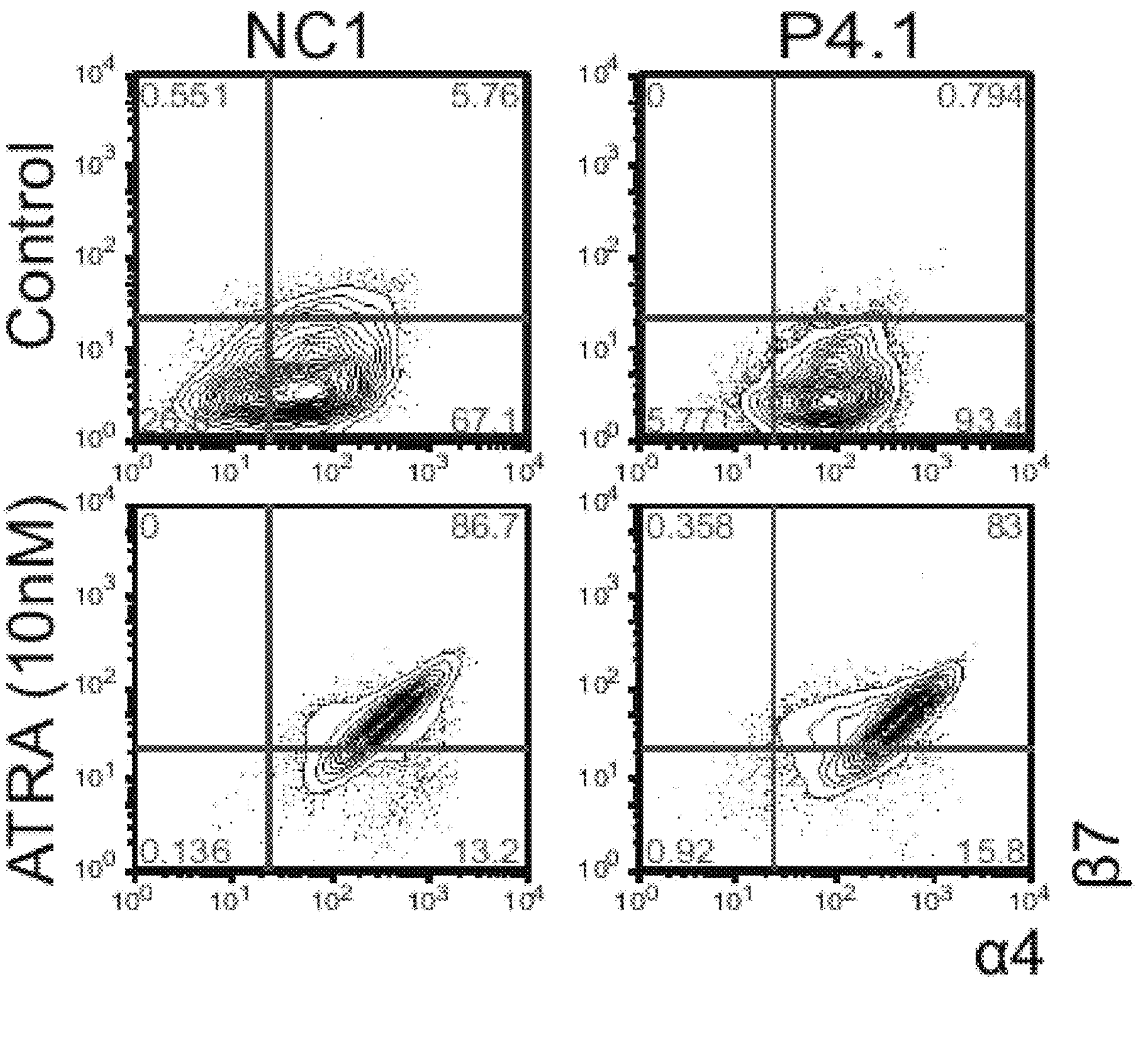
Figure 10E:
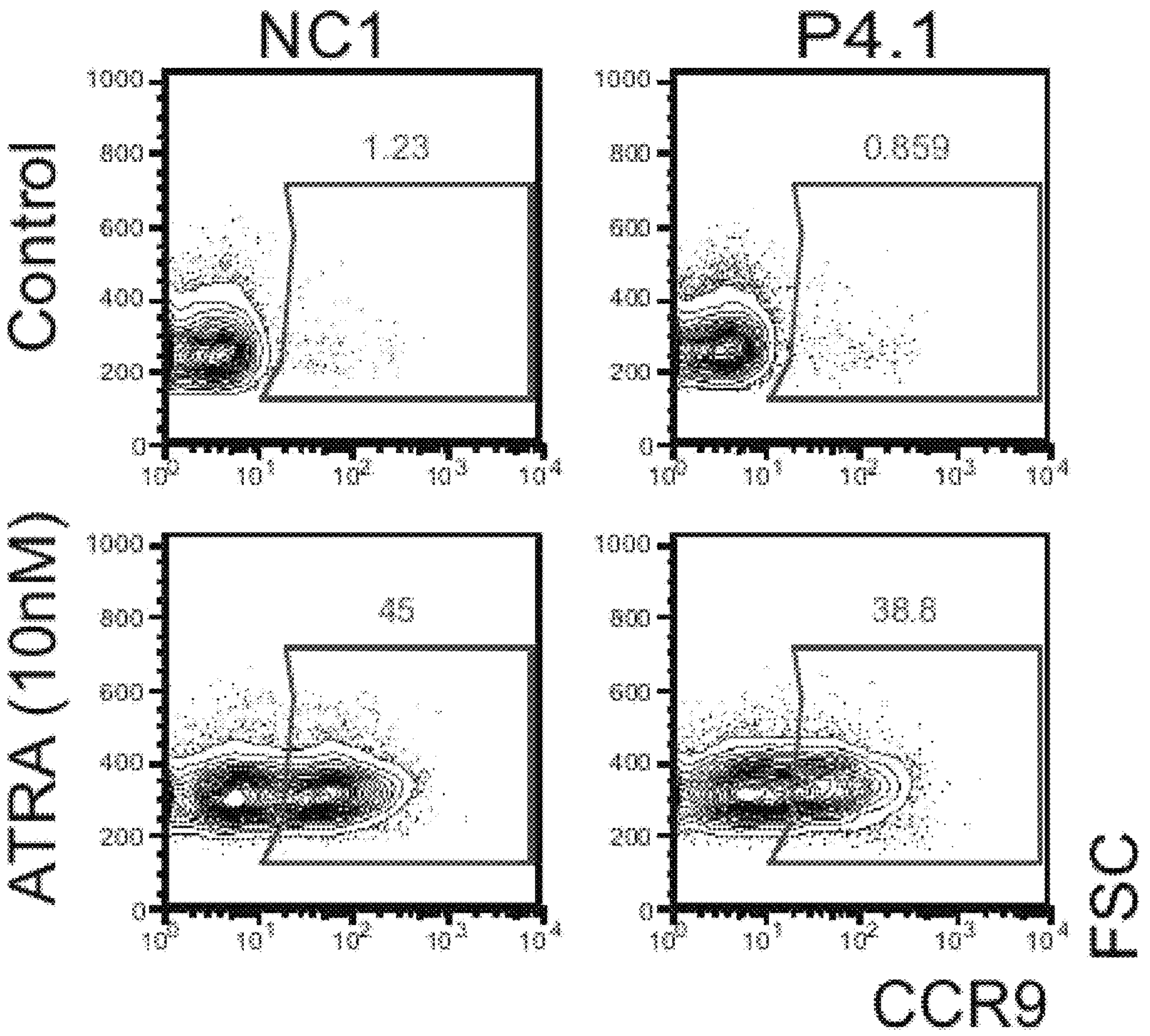

CD55-deficient T Cells have an Increased Inflammatory Cytokine Profile. Complement proteins are mainly produced in the liver, but also locally by cells of the immune system (dendritic cells and T cells). Immune cell complement can provide costimulatory and Th1 differentiation signals to T cells through either CD46-mediated sensing of deposited C3b or through the C3a/C5a anaphylatoxins signaling through the anaphylatoxin receptors (AnR) C3aR and C5aR. CD55 governs complement activation and consequent immune stimulation. Cytokine secretion by patient $CD4^+$ T cells was measured during primary and secondary stimulation with TCR agonistic antibodies and found increased TNFα and less IL-10 production compared to controls (FIGS. 9A, 9B, 10A, and 10B). No consistent differences were detected for IFNγ secretion (FIGS. 9C and 10C). To determine if the altered cytokine secretion was dependent on increased AnR signaling, small molecule inhibitors of C3aR and C5aR1 were used to block anaphylatoxin signaling. AnR inhibition decreased overall TNFα production and abrogated the difference between patient cells and controls (FIG. 9A). However, AnR inhibition did not rescue IL-10 production in patient T cells suggesting that the IL-10 secretion defect did not require AnR stimulation. Activated human $CD4^+$ T cells expressed C3aR, but not C5aR1 or C5aR2, suggesting that C3a may play a larger role than C5a in T-cell activation (FIG. 9D). Interestingly, surface expression of C3aR on T cells depended on the presence of all trans retinoic acid (ATRA) and there was comparable expression between patient and control cells (FIG. 9E). As previously demonstrated, T cells grown in the presence of ATRA expressed the chemokine receptor CCR9 and the integrin α4β7 that promote gut homing (FIGS. 10D and 10E). This suggests that gut homing T cells are also best suited to respond to anaphylatoxin products of complement activation.

Figure 10F:
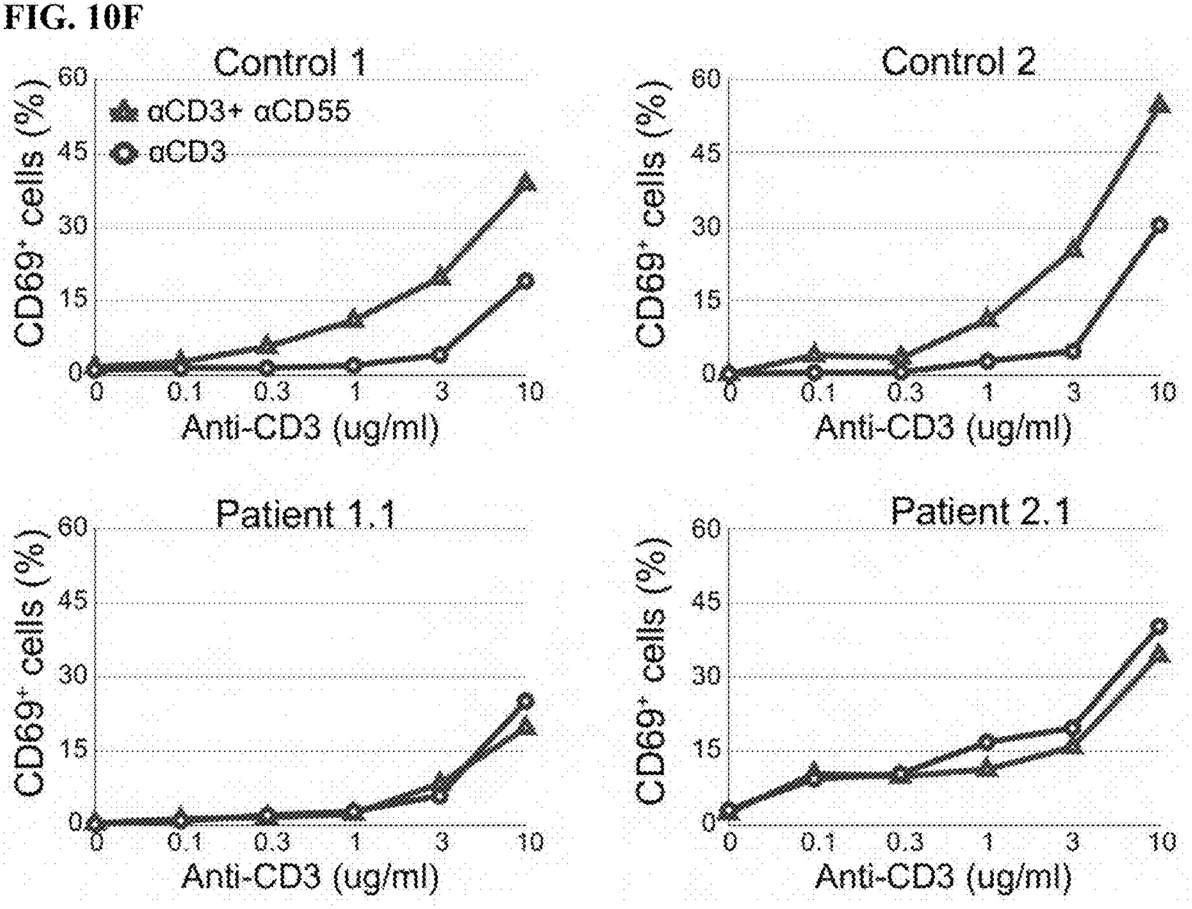
Figure 10G:
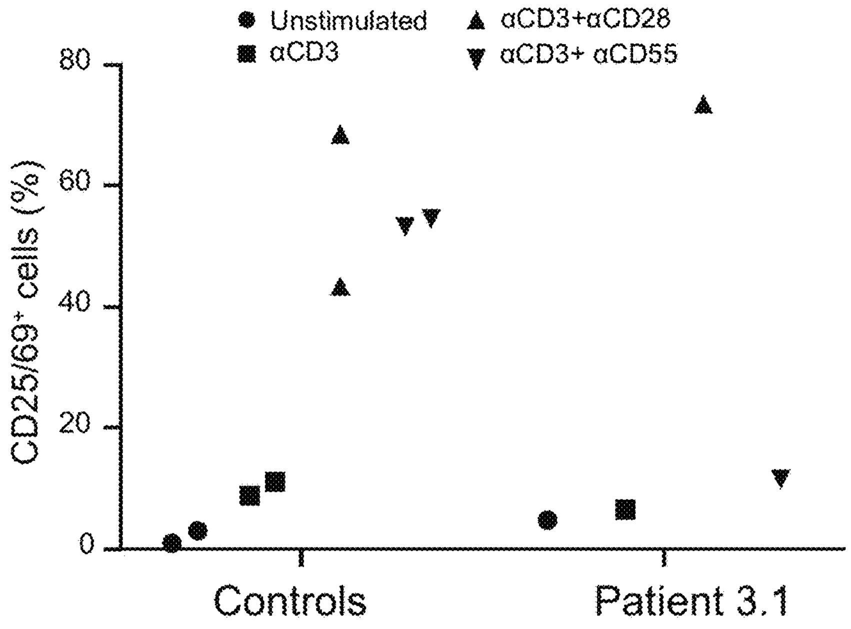
Figure 10H:
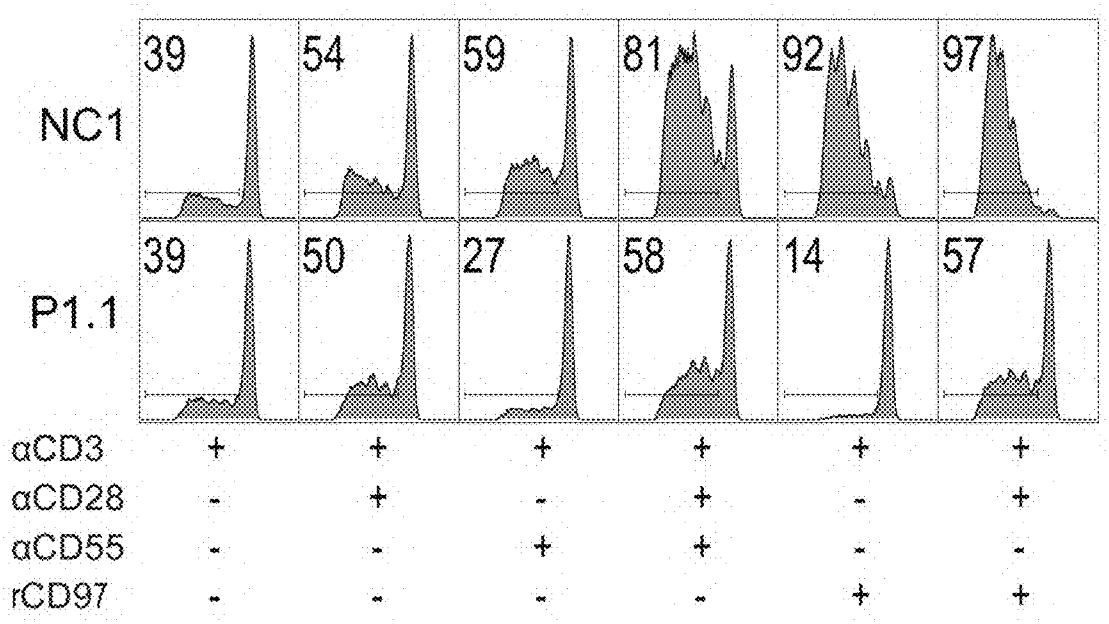
Figure 10I:
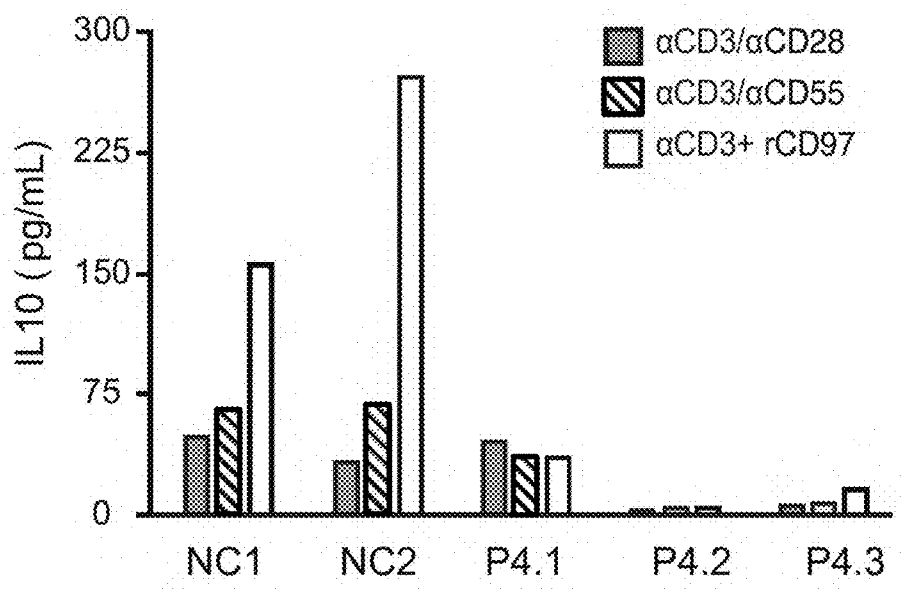

In addition to complement regulation, CD55 mediates a co-stimulatory signal through interactions with CD97 that enhances T-cell activation and the production of the anti-inflammatory cytokine IL-10. Patient cells failed to respond to anti-CD55 or CD97, the natural ligand for CD55, mediated costimulation as reflected by CD69 and CD25 upregulation and proliferation (FIG. 10F-10H). Additionally, patient T cells lacked CD55-dependent IL-10 production (FIGS. 9F and 10I). Taken together, these data demonstrate a critical role for CD55 in controlling complement and non-complement mediated production of proinflammatory and anti-inflammatory cytokines, respectively.

Figure 9G:
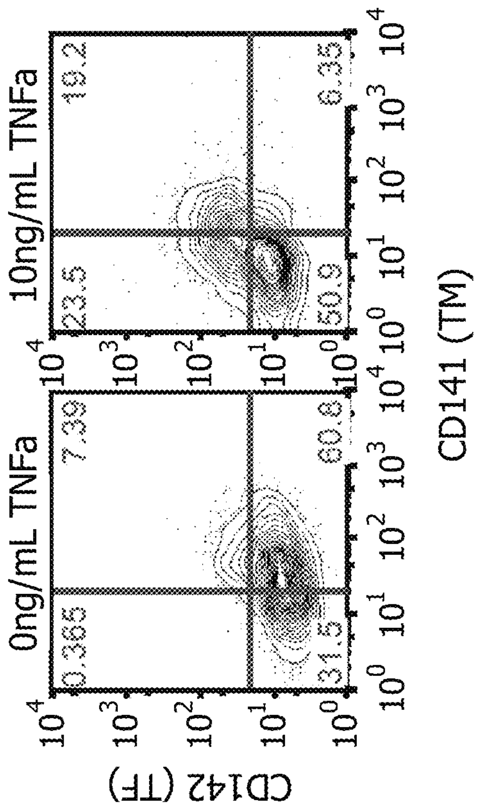

TNFα and ATRA Regulate Complement and Coagulation Regulatory Proteins on Endothelial Cells. CD55-deficient patients are susceptible to thrombotic events, suggesting an abnormality in the regulation of the coagulation cascade. Inflammatory cytokines, such as TNFα, can modulate the coagulant and thrombotic properties of endothelial cells by down regulating thrombomodulin (TM) and up regulating tissue factor (TF) expression. As T cells from the patients make more TNFα compared to controls, next it was determined how TNFα modulates complement and coagulation. As previously demonstrated, TNFα treatment induces procoagulatory TM and TF expression on the surface of treated endothelial cells (FIGS. 9G and 9H). Interestingly, inventors also found that TNFα, treatment decreased CD46 and CD59 expression, while modestly increasing CD55 expression on endothelial cells (FIG. 9I-9L). It was previously determined that ATRA increased surface expression of C3aR on human $CD4^+$ T cells and next sought to determine if ATRA similarly affected endothelial cells. While no expression of C3aR, C5aR, or C5aR2 was found on HUVEC cells either with or without ATRA addition (data not shown), ATRA treatment did result in a dose-dependent decrease in thrombomodulin expression with a concomitant increase in CD55 expression and no change in either CD46 or CD59 (FIGS. 9M-9P). Combined, these data suggest that the proinflammatory cytokines preferentially secreted by patient immune cells predispose endothelial cells to the activation of both the complement and coagulation cascades. This may be further exacerbated by high local concentrations of ATRA, which are often found in intestinal tissues due to dietary intake and absorption of retinols.

Compstatin Inhibits C3d Deposition on Human Cells. FIG. 11A illustrates that Compstatin inhibits C3d deposition on human T cells. C3d deposition was substantially increased in patient T cells treated with 5% nHS, as compared to control treatments and T cells. The increase was substantially inhibited by the addition of 100 μM Compstatin. Similarly, as shown in FIG. 11B, the ratio of C3a to C4a in culture supernatants from patient T cells after 24 hours of incubation with 5% nHS 100 μM Compstatin was considerably decreased relative to patient samples not treated with Compstatin. In FIG. 11C, the ratio of C5a to C4a in culture supernatants of patient T cells after 24 hours of incubation with 5% nHS and 100 μM Compstatin is decreased, as compared to patient T cells not treated with Compstatin. ***=$p<0.001$.

Discussion A severe chronic syndrome of inherited PLE is described with lymphangiectasia, thrombotic angiopathy, and atypical IBD caused by loss-of-function (LOF) mutations in the CD55 gene. Our results show that loss of CD55 causes dysregulated complement activation, anaphylatoxin signaling, inflammatory cytokine production, and thrombophilia via induction of the coagulation cascade. CD55 deficiency, Hyperactivation of complement, Angiopathic thrombosis and Protein Losing Enteropathy (CHAPLE) syndrome is defined herein as a heritable cause of complement-mediated lymphangiectasia. The cohort described herein shows that CHAPLE syndrome presents with variable expressivity, from subclinical to life threatening presentations, potentially explaining the variation in intestinal disease previously associated with the Inab phenotype.

Complement is a tightly regulated system of plasma and cell surface proteins that promotes the phagocytosis and destruction of microbes and modulates the local immune response through soluble anaphylatoxins. Inherited or acquired defects in complement inhibitory proteins lead to distinct syndromes in different organ systems which include paroxysmal nocturnal hemoglobinuria (PNH), atypical hemolytic uremic syndrome (aHUS), dense deposit disease, and age-related macular degeneration (FIG. 6A). PNH results from somatic mutations of the PIGA gene in hematopoietic precursors. This leads to the loss of GPI-anchored complement inhibitory proteins, including CD55 and CD59, causing terminal-complement mediated hemolysis with secondary thrombotic risk due to platelet activation. Germline LOF mutations affecting the complement regulatory proteins Factor H, Factor I, and CD46 or the anti-coagulatory protein thrombomodulin, result in the development of aHUS which is characterized by activation and damage of glomerular microvascular endothelial cells by complement intermediates and the membrane-attack complex, hemolysis due to mechanical injury, and kidney failure due to microthrombotic angiopathy. Defects in these same genes can cause age-related macular degeneration due to complement deposition in the retina. Unlike PNH and aHUS, hemolysis or kidney failure was not observed in CHAPLE patients. By contrast, CHAPLE patients, like PNH and aHUS patients, have an increased risk of thrombosis, highlighting that excessive complement activation can lead to induction of the coagulation cascade. The differences in clinical phenotype between PNH, aHUS, and CHAPLE syndrome may be due to varying cellular tropisms of the affected complement regulatory proteins or due to differences in the extent of complement activation. For instance, hemolysis or complement-dependent cell death was not detected in CHAPLE patients, suggesting little, if any, membrane-attack complex forms, differentiating this disease from PNH and aHUS.

Interestingly, it was observed that CD55 deficiency primarily manifests as an intestinal disease, occasionally complicated by life-threatening thromboembolism. The locations affected by thrombotic disease in CHAPLE patients (abdomen and brain) was similar to PNH and dissimilar to aHUS, which primarily affects the kidneys. This may reflect expression patterns of CD55 and other complement regulatory proteins. Supporting this idea, CD55 protein expression was found to be increased on endothelial cells in response to both TNFα and ATRA. During normal immune responses TNFα induction of CD55 may limit complement activation and prevent host damage. ATRA is a biologically active metabolite of Vitamin A/retinol, which is strictly acquired through diet. As such, intestinal tissues are exposed to a high amount of retinol and its metabolites and these metabolites play key roles in controlling the intestinal innate and adaptive immune response. Another possibility is that the constant microbial challenge in the intestinal tract predisposes this area to complement activation and activation of innate and adaptive immune responses, which may be hyperactivated by the absence of CD55. Additionally, TNFα and IL-10, whose production is altered in patient T cells, are critical for the regulation of universal inflammatory responses and deficiency of these cytokines preferentially causes intestinal disease, suggesting that intestinal tissues are sensitive to changes in the inflammatory cytokine milieu. Given the observation that ATRA drives both C3aR expression and a gut homing phenotype on human $CD4^+$ T cells, it is likely that T cells in the intestinal tissues are sensitized to the detection and activation by complement components. Collectively, these factors likely drive the intestinal disease associated with CD55 deficiency.

The hallmarks of CHAPLE syndrome or disease are early-onset PLE with lymphangiectasia and IBD. This is attributable to 3 relevant pathogenic mechanisms: i) impaired endothelial or epithelial barrier function due to signaling by anaphylatoxins or sub-lytic MAC deposition, ii) increased pressure due to thrombotic events, and iii) changes to the inflammatory cytokine environment. CD55-deficient mice show increased complement-dependent susceptibility to dextran sodium sulfate (DSS)-induced colitis, with complement deposition on IECs. The thrombotic events in CHAPLE patients, when localized to mesenteric tissue, may drive increased lymphatic pressure and exacerbate intestinal lymphangiectasia and chronic PLE. CD55-deficient patient T cells produce more TNFα and less IL-10, thereby creating a pro-inflammatory milieu. TNFα production was found to be dependent on anaphylatoxin signaling, while decreased IL-10 production was likely due to loss of CD55-mediated T-cell costimulation. CD55-deficient mice show similar alterations in cytokines. Taken together, these data show that complement activation is critical to disease pathogenesis (FIGS. 12A and 12B).

The patients with CHAPLE disease described herein have a chronic and severely debilitating, sometimes fatal, clinical course. As such patients with early-onset PLE should be screened for CD55 expression. CHAPLE patients have responded well to protein infusion and resection of localized lymphangiectatic intestinal segments; though albumin infusion provides only a transient palliation of symptoms and patients require ongoing treatment. Attempts to treat this disorder with conventional immunosuppressants, somatostatin analogues, or anticoagulants have been met with only a moderate degree of success in individual patients. Given the complement-mediated pathogenesis of this disorder, it is believed that agents that inhibit the complement-pathway (e.g., the complement-inhibitory monoclonal antibody Eculizumab, which has been used successfully in PNH and aHUS, or Compstatin), would be effective at treating CHAPLE patients. Eculizumab blocks C5 cleavage, thereby preventing the formation of the potent anaphylatoxin C5a and progression to the terminal complement cascade, two critical mediators of effector function in the complement cascade. While CD55 regulates the C5 convertase, making Eculizumab a good target therapy, it also regulates the C3 convertase. Furthermore, Compstatin is a peptide inhibitor (i.e., a cyclic tridecapeptide) of the complement system. In particular, Compstatin binds component C3, thereby inhibiting C3 activation/cleavage. As such, any complement-pathway inhibitors, including C3 convertase and C5 convertase inhibitors are possible therapeutic agents for treating patients with CHAPLE disease.

SPECIFIC EMBODIMENTS

An aspect provided by the present disclosure is a method of diagnosing a patient with CD55 deficiency, hyperactivation of complement, angiopathic thrombosis and protein losing enteropathy (CHAPLE) is provided. The method comprises: providing a sample from a patient; detecting at least one of: at least one mutation in a DNA sequence of a CD55 gene; at least one mutation in a RNA sequence of a CD55 transcript; at least one mutation in a DNA sequence of a CD55 complementary DNA (cDNA); CD55 protein; CD55 protein binding; complement deposition; or combinations thereof, wherein a mutation in the CD55 gene, transcript or cDNA, or absence or decrease in activity of CD55 protein is indicative of a patient at risk of developing or having CHAPLE; and diagnosing the patient as having or not having CHAPLE.

In any aspect or embodiment described herein, the patient is diagnosed with CHAPLE when at least one of the following is detected: at least one mutation in a DNA sequence, an RNA sequence or a cDNA sequence of CD55 that results in a CD55 protein with substantially diminished functional activity, a CD55 protein with no functional activity, a lack of expression of CD55 protein (i.e., no CD55 protein expression), or a substantially diminished expression of CD55 protein; a CD55 protein with substantially diminished functional activity; a CD55 protein with no functional activity; a lack of expression of CD55 protein (i.e., no CD55 protein expression); a substantially diminished expression of CD55 protein; or combinations thereof.

In any aspect or embodiment described herein, the patient is diagnosed with CHAPLE when the patient has at least one CHAPLE related symptom and at least one of the following is detected: at least one mutation in a DNA sequence, an RNA sequence or a cDNA sequence of CD55 that results in a CD55 protein with substantially diminished functional activity, a CD55 protein with no functional activity, a lack of expression of CD55 protein (i.e., no CD55 protein expression), or a substantially diminished expression of CD55 protein; a CD55 protein with substantially diminished functional activity; a CD55 protein with no functional activity; a lack of expression of CD55 protein (i.e., no CD55 protein expression); a substantially diminished expression of CD55 protein; or combinations thereof.

In any aspect or embodiment described herein, the CHAPLE related symptom is selected from the group consisting of: inflammatory bowel disease, enteropathy, protein losing enteropathy, protein losing enteropathy associated with hypoalbuminemia, hypoalbuminemia, hypogammaglobulinemia, intestinal lymphangiectasia, lymphangiectasia, thrombotic events, thromboembolism, hyperactivation of complement, angiopathic thrombosis, hypoproteinemia, or combinations thereof.

In any aspect or embodiment described herein, the method further comprises administering an effective amount of a composition comprising at least one complement inhibitor to the subject with CHAPLE, wherein the composition is effective in treating or preventing at least one symptom of CHAPLE.

In any aspect or embodiment described herein, the complement inhibitor is selected from the group consisting of a serine protease inhibitor, a soluble complement regulator, a therapeutic antibody or an antigen-binding fragment thereof, a complement component inhibitor, and an anaphylatoxin receptor antagonist.

In any aspect or embodiment described herein, the mutation in the DNA sequence of the CD55 gene or in the RNA sequence of the CD55 transcript results in a near to complete absence of CD55 protein expression or the expression of CD55 protein with substantially diminished function or that is non-functional.

In any aspect or embodiment described herein, the mutation in the DNA sequence of the CD55 gene is at least one of:_c.149-150delAA;_c.149-150insCCTT; c.109delC; c.800G>C; c.287-1G>C; c.149-150delAAinsCCTT; or combinations thereof.

In any aspect or embodiment described herein, detecting includes at least one of: sequencing at least a portion of the CD55 gene or the CD55 transcript or the CD55 cDNA; or contacting a labeled nucleic acid probe to at least a portion of the CD55 gene or the CD55 transcript or the CD55 cDNA; or contacting at least a portion of the CD55 gene or CD55 transcripts or cDNA thereof with a microarray; or combinations thereof.

In any aspect or embodiment described herein, hybridization of the labeled nucleic acid probe is indicative of a mutation in the portion of the CD55 gene or CD55 transcript.

In any aspect or embodiment described herein, hybridization of the labeled nucleic acid probe is indicative of the portion of the CD55 gene or CD55 transcript having a wild-type sequence at the location of hybridization.

In any aspect or embodiment described herein, sequencing at least a portion of the CD55 gene or CD55 transcript or cDNA thereof includes amplifying at least one region of interest for sequencing with at least one polymerase chain reaction (PCR) with at least one of the following primer sets: CTACTCCACCCGTCTTGTTTGT (SEQ ID NO.4) and TTTGGGGGTTAAGGATACAGTC (SEQ ID NO.5) (Exon 1); CAGGTGTGGCATTTCAAGG (SEQ ID NO.6) and ACCCTGGGGTTTAGTAACGC (SEQ ID NO.7) (Exon 2); AAGTACTAAATATGCGCAAAGCAG (SEQ ID NO.8) and ATGGTCCTATCAAGAAACATCC (SEQ ID NO.9) (Exon 3); GTTACCTTCTTTGTGTGTATGCC (SEQ ID NO.10) and GCTGTGAATACCAGTCATGAAAC (SEQ ID NO.11) (Exon 4); AACCTGGAGAATTTGAGGAAAG (SEQ ID NO.12) and TGTGCTAATATTCTTAAGGGGC (SEQ ID NO.13) (Exon 5); GCATTTATAAGCATCTCTTGTTGG (SEQ ID NO.14) and TCATTGAATGTCTGCAACCC (SEQ ID NO.15) (Exon 6); CTAGGTGTTTGTGGGGAGAGAG (SEQ ID NO.16) and TCTGGTGGGTTTCTGAAGAGTT (SEQ ID NO.17) (Exon 7); TTTACGCAGAGTCCTTCAGC (SEQ ID NO.18) and CCATTTAATCCTGCAATCTTGG (SEQ ID NO.19) (Exon 8); TGGAAATTTGAGTTGCTTTCG (SEQ ID NO.20) and TCTCCCAGGAATATGGATTG (SEQ ID NO.21) (Exon 9); GCACCCCAAATTAACTGATTC (SEQ ID NO.22) and ATGTGATTCCAGGACTGCC (SEQ ID NO.23) (Exon 10); or combinations thereof.

In any aspect or embodiment described herein, contacting a labeled nucleic acid probe to at least a portion of the CD55 gene or the CD55 transcript or the CD55 cDNA is performed using real-time PCR.

In any aspect or embodiment described herein, contacting a labeled nucleic acid probe to at least a portion of the CD55 transcripts or cDNA thereof comprises: isolating CD55 transcripts; reverse transcribing at least a portion of the CD55 transcripts; and contacting the cDNA with the labeled nucleic acid probe.

In any aspect or embodiment described herein, the microarray includes probes designed to detect DNA, transcript, or cDNA mutations that result in the complete absence in CD55 protein or a non-functional CD55 protein.

In any aspect or embodiment described herein, detecting CD55 protein comprises: contacting the sample with at least one CD55 binding polypeptide.

In any aspect or embodiment described herein, the CD55 binding polypeptide includes a detectable label.

In any aspect or embodiment described herein, the binding polypeptide is an anti-CD55 antibody or a CD55-binding fragment thereof.

In any aspect or embodiment described herein, detecting CD55 protein further comprises contacting the sample or a CD55-CD55 binding polypeptide complex with at least one secondary polypeptide that binds specifically to the CD55 binding polypeptide.

In any aspect or embodiment described herein, the secondary polypeptide includes a detectable label.

In any aspect or embodiment described herein, the secondary polypeptide is an antibody or fragment thereof that binds the CD55 binding polypeptide.

In any aspect or embodiment described herein, the detecting of CD55 protein is performed using at least one of a western blot, flow cytometry, an immunoassay, or combinations thereof.

In any aspect or embodiment described herein, the immunoassay is at least one assay selected from the group consisting of enzyme-linked immunosorbent assay (ELISA), radioimmunoassay, magnetic immunoassay, enzyme-linked immunospot (ELISPOT), immunofluorescence; and combinations thereof.

In any aspect or embodiment described herein, the detecting of CD55 binding function includes examining the at least one of C3b affinity, C3b avidity, C4b affinity, C4b avidity, or combinations thereof.

In any aspect or embodiment described herein, detecting complement deposition includes detecting C3d deposition.

A further aspect provided by the present disclosure is a method of treating a patient with CD55 deficiency, hyperactivation of complement, angiopathic thrombosis and protein losing enteropathy (CHAPLE) or preventing at least one symptom of CHAPLE in a patient at risk of developing the same. The method comprises: administering an effective amount of a composition comprising at least one complement inhibitor to a subject in need thereof, wherein the composition is effective in treating or preventing at least one symptom of CHAPLE.

In any aspect or embodiment described herein, the complement inhibitor is selected from the group consisting of a serine protease inhibitor, a soluble complement regulator, a therapeutic antibody or an antigen-binding fragment thereof, a complement component inhibitor, and an anaphylatoxin receptor antagonist.

In any aspect or embodiment described herein, the serine protease inhibitors is at least one of a C3 convertase inhibitor, a C5 convertase inhibitor, a C1 inhibitor, a C1r inhibitor, a C1s inhibitor, a C2a inhibitor, a MASP-1 inhibitor, a MASP-2 inhibitor, a factor D inhibitor, a factor B inhibitor, a factor I inhibitor or combinations thereof.

In any aspect or embodiment described herein, the serine protease inhibitor is at least one of BCX-1470 (BioCryst, Birmingham, AL, USA), C1s-INH-248 (Knoll/Abbott, Abbott Park, IL, USA), compstatin, Cetor® (Sanquin, Amsterdam, Netherlands), Berinert® (CSL Behring, King of Prussia, PA, USA), Cinryze™ (ViroPharma, Exton, PA, USA), rhC1INH (Pharming Group N.V., Leiden, Netherlands), Ruconest® (Salix Pharmaceuticals, Inc., Raleigh, NC, USA) or combinations thereof.

In any aspect or embodiment described herein, the soluble complement regulator is at least one of a soluble form of a membrane cofactor protein (MCP or CD46), a soluble form of a decay-accelerating factor (DAF or CD55), a soluble form of a membrane attack complex-inhibitor protein (MAC-IP or CD59), a soluble form of complement receptor 1 (CD35) or combinations thereof.

In any aspect or embodiment described herein, the soluble complement regulator is at least one of sCR1 (TP10; Advant Immunotherapeutics, Needham, MA, USA), sCR1-sL$^{ex}$ (TP10; Advant Immunotherapeutics, Needham, MA, USA), sDAG-sMCP hybrid (MLN-2222, Millennium, Cambridge, MA, USA), a membrane-tethered sCD59 (Mirococept or APT070; Inflazyme Pharmaceuticals, Vancouver, British Columbia, Canada) or combinations thereof.

In any aspect or embodiment described herein, the therapeutic antibody or the antigen-binding fragment thereof is at least one polypeptide that binds C3, C3a, C3b, C3 convertase, C5, C5a, C5b, C5 convertase, C7, C8, or C9, factor B, factor D, C4, C2, C1, properdin, a functional blocking antibody of an anaphylatoxin or combinations thereof, wherein said binding inhibits complement activation by at least one of blocking association/binding with other complement proteins, blocking association/binding with receptor proteins, blocking serine protease activity or combinations thereof.

In any aspect or embodiment described herein, the therapeutic antibody or the antigen-binding fragment thereof is at least one of eculizumab (Soliris®; Alexion Pharmaceuticals Inc., New Haven, CT, USA), ALXN1007 (Alexion Pharmaceuticals Inc., New Haven, CT, USA), neutrazumab (G2 Therapies, Darlinghurst, NSW, Australia), Pexelizumab (Alexion Pharmaceuticals Inc., New Haven, CT, USA), ofatumumab (Genmab A/S, Copenhagen, Denmark), HuMax-CD38 (Benmab A/S, Copenhagen, Denmark), TNX-558 (Tanox, South San Francisco, CA, USA), TNX-234 (Tanox, South San Francisco, CA, USA), TA106 (Taligen, Aurora, CO, USA), anti-properdin (Novelmed, Cleveland, OH, USA) or combinations thereof.

In any aspect or embodiment described herein, the complement component inhibitor is a peptide, nucleic acids, a synthetic molecule or a combination thereof that disrupts protein functions by steric hindrance or the induction of conformational changes.

In any aspect or embodiment described herein, the complement component inhibitor is at least one of compstatin, anti-C5 RNA aptamer (ARC1905; Archemix, Cambridge, MA, USA), or analogs or derivatives thereof, or combinations thereof.

In any aspect or embodiment described herein, the anaphylatoxin receptor antagonist is at least one of a C5aR antagonist, a C5L2 antagonist, a C3a receptor antagonist, a functional blocking antibody of an anaphylatoxin or combinations thereof.

In any aspect or embodiment described herein, the anaphylatoxin receptor antagonist is at least one of PMX-53 (PepTech Corp, Bedform, MA, USA), PMX-205 (PepTech Corp, Bedform, MA, USA), JPE-1375 (Jerini, Berlin, Germany), JSM-7717 (Jerini, Berlin, Germany), rhMBL (Enzon Pharmaceuticals, Cranford, NJ, USA) or combinations thereof.

An additional aspect provided by the present disclosure is a therapeutic composition for treating or preventing at least one symptom of CD55 deficiency, hyperactivation of complement, angiopathic thrombosis and protein losing enteropathy (CHAPLE). The composition comprises: an effective amount of two or more agents, wherein at least one of the agents is a complement inhibitor to a subject in need thereof; and a pharmaceutically acceptable carrier, wherein the composition is effective in treating or preventing at least one symptom of CHAPLE.

In any aspect or embodiment described herein, the complement inhibitor is selected from the group consisting of a serine protease inhibitor, a soluble complement regulator, a therapeutic antibody or an antigen-binding fragment thereof, a complement component inhibitor, and an anaphylatoxin receptor antagonist.

In any aspect or embodiment described herein, the complement inhibitors include a C3 convertase inhibitor and a C5 convertase inhibitor.

In any aspect or embodiment described herein, the serine protease inhibitors is at least one of a C3 convertase inhibitor, a C5 convertase inhibitor, a C1 inhibitor, a C1r inhibitor, a C1s inhibitor, a C2a inhibitor, a MASP-1 inhibitor, a MASP-2 inhibitor, a factor D inhibitor, a factor B inhibitor, a factor I inhibitor or combinations thereof.

In any aspect or embodiment described herein, the serine protease inhibitor is at least one of BCX-1470 (BioCryst, Birmingham, AL, USA), C1s-INH-248 (Knoll/Abbott, Abbott Park, IL, USA), compstatin, Cetor® (Sanquin, Amsterdam, Netherlands), Berinert® (CSL Behring, King of Prussia, PA, USA), Cinryze™ (ViroPharma, Exton, PA, USA), rhC1INH (Pharming Group N.V., Leiden, Netherlands), Ruconest® (Salix Pharmaceuticals, Inc., Raleigh, NC, USA) or combinations thereof.

In any aspect or embodiment described herein, the soluble complement regulator is at least one of a soluble form of a membrane cofactor protein (MCP or CD46), a soluble form of a decay-accelerating factor (DAF or CD55), a soluble form of a membrane attack complex-inhibitor protein (MAC-IP or CD59), a soluble form of complement receptor 1 (CD35) or combinations thereof.

In any aspect or embodiment described herein, the soluble complement regulator is at least one of sCR1 (TP10; Advant Immunotherapeutics, Needham, MA, USA), sCR1-sL$^{ex}$ (TP10; Advant Immunotherapeutics, Needham, MA, USA), sDAG-sMCP hybrid (MLN-2222, Millennium, Cambridge, MA, USA), a membrane-tethered sCD59 (Mirococept or APT070; Inflazyme Pharmaceuticals, Vancouver, British Columbia, Canada) or combinations thereof.

In any aspect or embodiment described herein, the therapeutic antibody or the antigen-binding fragment thereof is at least one polypeptide that binds C3, C3a, C3b, C3 convertase, C5, C5a, C5b, C5 convertase, C7, C8, or C9, factor B, factor D, C4, C2, C1, properdin, a functional blocking antibody of an anaphylatoxin or combinations thereof, wherein said binding inhibits complement activation by at least one of blocking association/binding with other complement proteins, blocking association/binding with receptor proteins, blocking serine protease activity or combinations thereof.

In any aspect or embodiment described herein, the therapeutic antibody or the antigen-binding fragment thereof is at least one of eculizumab (Soliris®; Alexion Pharmaceuticals Inc., New Haven, CT, USA), ALXN1007 (Alexion Pharmaceuticals Inc., New Haven, CT, USA), neutrazumab (G2 Therapies, Darlinghurst, NSW, Australia), Pexelizumab (Alexion Pharmaceuticals Inc., New Haven, CT, USA), ofatumumab (Genmab A/S, Copenhagen, Denmark), HuMax-CD38 (Benmab A/S, Copenhagen, Denmark), TNX-558 (Tanox, South San Francisco, CA, USA), TNX-234 (Tanox, South San Francisco, CA, USA), TA106 (Taligen, Aurora, CO, USA), anti-properdin (Novelmed, Cleveland, OH, USA) or combinations thereof.

In any aspect or embodiment described herein, the complement component inhibitor is a peptide, nucleic acids, a synthetic molecule or a combination thereof that disrupts protein functions by steric hindrance or the induction of conformational changes.

In any aspect or embodiment described herein, the complement component inhibitor is at least one of compstatin, anti-C5 RNA aptamer (ARC1905; Archemix, Cambridge, MA, USA), or analogs or derivatives thereof, or combinations thereof.

In any aspect or embodiment described herein, the anaphylatoxin receptor antagonist is at least one of a C5aR antagonist, a C5L2 antagonist, a C3a receptor antagonist, a functional blocking antibody of an anaphylatoxin or combinations thereof.

In any aspect or embodiment described herein, the anaphylatoxin receptor antagonist is at least one of PMX-53 (PepTech Corp, Bedform, MA, USA), PMX-205 (PepTech Corp, Bedform, MA, USA), JPE-1375 (Jerini, Berlin, Germany), JSM-7717 (Jerini, Berlin, Germany), rhMBL (Enzon Pharmaceuticals, Cranford, NJ, USA) or combinations thereof.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims.

REFERENCES

1. Umar S B, DiBaise J K. Protein-losing enteropathy: case illustrations and clinical review. Am J Gastroenterol 2010; 105:43-9; quiz 50.
2. Parfitt A M. Familial neonatal hypoproteinaemia with exudative enteropathy and intestinal lymphangiectasis. Arch Dis Child 1966; 41:54-62.
3. Quintana-Murci L, Alcais A, Abel L, Casanova J L. Immunology in natura: clinical, epidemiological and evolutionary genetics of infectious diseases. Nature immunology 2007; 8:1165-71.
4. de Jesus A A, Canna S W, Liu Y, Goldbach-Mansky R. Molecular mechanisms in genetically defined autoinflammatory diseases: disorders of amplified danger signaling. Annual review of immunology 2015; 33:823-74.
5. Aksentijevich I, Kastner D L. Genetics of monogenic autoinflammatory diseases: past successes, future challenges. Nature reviews Rheumatology 2011; 7:469-78.
6. Lenardo M, Lo B, Lucas C L. Genomics of Immune Diseases and New Therapies. Annual review of immunology 2015.
7. Lucas C L, Lenardo M J. Identifying genetic determinants of autoimmunity and immune dysregulation. Curr Opin Immunol 2015; 37:28-33.
8. Reuter J A, Spacek D V, Snyder M P. High-throughput sequencing technologies. Molecular cell 2015; 58:586-97.
9. Auton A, Brooks L D, Durbin R M, et al. A global reference for human genetic variation. Nature 2015; 526:68-74.
10. Lek M, Karczewski K, Minikel E, et al. Analysis of protein-coding genetic variation in 60,706 humans. bioRxiv 2015.
11. Uhlig H H, Schwerd T, Koletzko S, et al. The diagnostic approach to monogenic very early onset inflammatory bowel disease. Gastroenterology 2014; 147:990-1007 e3.

12. Elkadri A, Thoeni C, Deharvengt S J, et al. Mutations in Plasmalemma Vesicle Associated Protein Result in Sieving Protein-Losing Enteropathy Characterized by Hypoproteinemia, Hypoalbuminemia, and Hypertriglyceridemia. Cell Mol Gastroenterol Hepatol 2015; 1:381-94 e7.
13. Lublin D M, Atkinson J P. Decay-accelerating factor: biochemistry, molecular biology, and function. Annual review of immunology 1989; 7:35-58.
14. Yazer M H, Judd W J, Davenport R D, et al. Case report and literature review: transient Inab phenotype and an agglutinating anti-IFC in a patient with a gastrointestinal problem. Transfusion 2006; 46:1537-42.
15. Daniels G L, Green C A, Mallinson G, et al. Decay-accelerating factor (CD55) deficiency phenotypes in Japanese. Transfus Med 1998; 8:141-7.
16. Daniels G L, Tohyama H, Uchikawa M. A possible null phenotype in the Cromer blood group complex. Transfusion 1982; 22:362-3.
17. Lin R C, Herman J, Henry L, Daniels G L. A family showing inheritance of the Inab phenotype. Transfusion 1988; 28:427-9.
18. Dobbs K, Dominguez Conde C, Zhang S Y, et al. Inherited DOCK2 Deficiency in Patients with Early-Onset Invasive Infections. The New England journal of medicine 2015; 372:2409-22.
19. Nakano Y, Sumida K, Kikuta N, Miura N H, Tobe T, Tomita M. Complete determination of disulfide bonds localized within the short consensus repeat units of decay accelerating factor (CD55 antigen). Biochim Biophys Acta 1992; 1116:235-40.
20. Bajic G, Degn S E, Thiel S, Andersen G R. Complement activation, regulation, and molecular basis for complement-related diseases. EMBO J 2015; 34:2735-57.
21. Ham T H, Dingle J H. Studies on Destruction of Red Blood Cells. Ii. Chronic Hemolytic Anemia with Paroxysmal Nocturnal Hemoglobinuria: Certain Immunological Aspects of the Hemolytic Mechanism with Special Reference to Serum Complement. J Clin Invest 1939; 18:657-72.
22. Barilla-LaBarca M L, Liszewski M K, Lambris J D, Hourcade D, Atkinson J P. Role of membrane cofactor protein (CD46) in regulation of C4b and C3b deposited on cells. J Immunol 2002; 168:6298-304.
23. Andoh A, Kinoshita K, Rosenberg I, Podolsky D K. Intestinal trefoil factor induces decay-accelerating factor expression and enhances the protective activities against complement activation in intestinal epithelial cells. J Immunol 2001; 167:3887-93.
24. Kolev M, Le Friec G, Kemper C. Complement-tapping into new sites and effector systems. Nat Rev Immunol 2014; 14:811-20.
25. Carroll M C. The complement system in regulation of adaptive immunity. Nature immunology 2004; 5:981-6.
26. Heeger P S, Kemper C. Novel roles of complement in T effector cell regulation. Immunobiology 2012; 217:216-24.
27. Cardone J, Le Friec G, Vantourout P, et al. Complement regulator CD46 temporally regulates cytokine production by conventional and unconventional T cells. Nature immunology 2010; 11:862-71.
28. Kolev M, Dimeloe S, Le Friec G, et al. Complement Regulates Nutrient Influx and Metabolic Reprogramming during Th1 Cell Responses. Immunity 2015; 42:1033-47.
29. Strainic M G, Liu J, Huang D, et al. Locally produced complement fragments C5a and C3a provide both costimulatory and survival signals to naive $CD4^+$ T cells. Immunity 2008; 28:425-35.
30. Lalli P N, Strainic M G, Yang M, Lin F, Medof M E, Heeger P S. Locally produced C5a binds to T cell-expressed C5aR to enhance effector T-cell expansion by limiting antigen-induced apoptosis. Blood 2008; 112: 1759-66.
31. Ghannam A, Fauquert J L, Thomas C, Kemper C, Drouet C. Human complement C3 deficiency: Th1 induction requires T cell-derived complement C3a and CD46 activation. Molecular immunology 2014; 58:98-107.
32. Liu J, Miwa T, Hilliard B, et al. The complement inhibitory protein DAF (CD55) suppresses T cell immunity in vivo. J Exp Med 2005; 201:567-77.
33. Miwa T, Maldonado M A, Zhou L, et al. Deletion of decay-accelerating factor (CD55) exacerbates autoimmune disease development in MRL/lpr mice. Am J Pathol 2002; 161:1077-86.
34. Miwa T, Maldonado M A, Zhou L, et al. Decay-accelerating factor ameliorates systemic autoimmune disease in MRL/lpr mice via both complement-dependent and -independent mechanisms. Am J Pathol 2007; 170: 1258-66.
35. Iwata M, Hirakiyama A, Eshima Y, Kagechika H, Kato C, Song S Y. Retinoic acid imprints gut-homing specificity on T cells. Immunity 2004; 21:527-38.
36. Spendlove I, Sutavani R. The role of CD97 in regulating adaptive T-cell responses. Adv Exp Med Biol 2010; 706:138-48.
37. Hot A, Lenief V, Miossec P. Combination of IL-17 and TNFalpha induces a pro-inflammatory, pro-coagulant and pro-thrombotic phenotype in human endothelial cells. Annals of the rheumatic diseases 2012; 71:768-76.
38. Ricklin D, Hajishengallis G, Yang K, Lambris J D. Complement: a key system for immune surveillance and homeostasis. Nature immunology 2010; 11:785-97.
39. Zipfel P F, Skerka C. Complement regulators and inhibitory proteins. Nat Rev Immunol 2009; 9:729-40.
40. Nicholson-Weller A, March J P, Rosenfeld S I, Austen K F. Affected erythrocytes of patients with paroxysmal nocturnal hemoglobinuria are deficient in the complement regulatory protein, decay accelerating factor. Proc Natl Acad Sci USA 1983; 80:5066-70.
41. Nicholson-Weller A, Burge J, Fearon D T, Weller P F, Austen K F. Isolation of a human erythrocyte membrane glycoprotein with decay-accelerating activity for C3 convertases of the complement system. J Immunol 1982; 129:184-9.
42. Nicholson-Weller A, Spicer D B, Austen K F. Deficiency of the complement regulatory protein, "decay-accelerating factor," on membranes of granulocytes, monocytes, and platelets in paroxysmal nocturnal hemoglobinuria. The New England journal of medicine 1985; 312:1091-7.
43. Risitano A M. Paroxysmal nocturnal hemoglobinuria and the complement system: recent insights and novel anticomplement strategies. Adv Exp Med Biol 2013; 735:155-72.
44. Noris M, Remuzzi G. Atypical hemolytic-uremic syndrome. The New England journal of medicine 2009; 361:1676-87.
45. Delvaeye M, Noris M, De Vriese A, et al. Thrombomodulin mutations in atypical hemolytic-uremic syndrome. The New England journal of medicine 2009; 361:345-57.

46. Hill A, Kelly R J, Hillmen P. Thrombosis in paroxysmal nocturnal hemoglobinuria. Blood 2013; 121:4985-96; quiz 5105.
47. Campistol J M, Arias M, Ariceta G, et al. An update for atypical haemolytic uraemic syndrome: diagnosis and treatment. A consensus document. Nefrologia: publicacion oficial de la Sociedad Espanola Nefrologia 2015; 35:421-47.
48. Landau D, Shalev H, Levy-Finer G, Polonsky A, Segev Y, Katchko L. Familial hemolytic uremic syndrome associated with complement factor H deficiency. The Journal of pediatrics 2001; 138:412-7.
49. Montes T, Goicoechea de Jorge E, Ramos R, et al. Genetic deficiency of complement factor H in a patient with age-related macular degeneration and membranoproliferative glomerulonephritis. Molecular immunology 2008; 45:2897-904.
50. Harrison E H. Mechanisms involved in the intestinal absorption of dietary vitamin A and provitamin A carotenoids. Biochim Biophys Acta 2012; 1821:70-7.
51. Raverdeau M, Mills K H. Modulation of T cell and innate immune responses by retinoic Acid. J Immunol 2014; 192:2953-8.
52. Neurath M F. Cytokines in inflammatory bowel disease. Nat Rev Immunol 2014; 14:329-42.
53. Glocker E O, Kotlarz D, Bortug K, et al. Inflammatory bowel disease and mutations affecting the interleukin-10 receptor. The New England journal of medicine 2009; 361:2033-45.
54. Schepp-Berglind J, Atkinson C, Elvington M, Qiao F, Mannon P, Tomlinson S. Complement-dependent injury and protection in a murine model of acute dextran sulfate sodium-induced colitis. J Immunol 2012; 188:6309-18.
55. Lin F, Spencer D, Hatala D A, Levine A D, Medof M E. Decay-accelerating factor deficiency increases susceptibility to dextran sulfate sodium-induced colitis: role for complement in inflammatory bowel disease. J Immunol 2004; 172:3836-41.
56. Liszewski M K, Kolev M, Le Friec G, et al. Intracellular complement activation sustains T cell homeostasis and mediates effector differentiation. Immunity 2013; 39:1143-57.
57. Cofiell R, Kukreja A, Bedard K, et al. Eculizumab reduces complement activation, inflammation, endothelial damage, thrombosis, and renal injury markers in aHUS. Blood 2015; 125:3253-62.
58. Lucas C L, Zhang Y, Venida A, et al. Heterozygous splice mutation in PIK3R1 causes human immunodeficiency with lymphoproliferation due to dominant activation of PI3K. J Exp Med 2014; 211:2537-47.
59. Ran F A, Hsu P D, Wright J, Agarwala V, Scott D A, Zhang F. Genome engineering using the CRISPR-Cas9 system. Nature protocols 2013; 8:2281-308.
60. Sanjana N E, Shalem O, Zhang F. Improved vectors and genome-wide libraries for CRISPR screening. Nat Methods 2014; 11:783-4.
61. Fridkis-Hareli M, Storek M, Mazsaroff I, Risitano A M, Lundberg A S, Horvath C J, Holers V A, Design and development of TT30, a novel C3d-targeted C3/C5 convertase inhibitor for treatment of human complement alternative pathway-medicated diseases. BLOOD 2011; 118(17): 4705-4713.

We claim:

1. A method of treating a subject having CD55 deficiency, hyperactivation of complement, angiopathic thrombosis and protein losing enteropathy (CHAPLE), the method comprising:

selecting a subject having CD55 deficiency, hyperactivation of complement, angiopathic thrombosis and protein losing enteropathy (CHAPLE); and administering an effect amount of a composition comprising at least one therapeutic antibody to the subject, wherein the therapeutic antibody is eculizumab, ALXN1007, neutrazumab, Pexelizumab, ofatumumab, HuMax-CD38, TNX-558, TNX-234, or TA106, thereby treating the subject having CD55 deficiency, hyperactivation of complement, angiopathic thrombosis and protein losing enteropathy (CHAPLE).

2. A method of treating a subject having CD55 deficiency, hyperactivation of complement, angiopathic thrombosis and protein losing enteropathy (CHAPLE), the method comprising:

selecting a subject having CD55 deficiency, hyperactivation of complement, angiopathic thrombosis and protein losing enteropathy (CHAPLE); and administering an effective amount of a composition comprising a therapeutic antibody to the subject, wherein the therapeutic antibody is eculizumab, thereby treating the subject having CD55 deficiency, hyperactivation of complement, angiopathic thrombosis and protein losing enteropathy (CHAPLE).

3. The method of claim 1, wherein the therapeutic antibody is ALXN1007.

4. The method of claim 1, wherein the therapeutic antibody is neutrazumab.

5. The method of claim 1, wherein the therapeutic antibody is Pexelizumab.

6. The method of claim 1, wherein the therapeutic antibody is ofatumumab.

7. The method of claim 1, wherein the therapeutic antibody is HuMax-CD38.

8. The method of claim 1, wherein the therapeutic antibody is TNX-558.

9. The method of claim 1, wherein the therapeutic antibody is TNX-234.

10. The method of claim 1, wherein the therapeutic antibody is TA106.

* * * * *

UNITED STATES PATENT AND TRADEMARK OFFICE

CERTIFICATE OF CORRECTION

PATENT NO. : 12,168,802 B2
APPLICATION NO. : 18/154745
DATED : December 17, 2024
INVENTOR(S) : Lenardo et al.

It is certified that error appears in the above-identified patent and that said Letters Patent is hereby corrected as shown below:

On the Title Page

At Lines 16-17 of item [57], the abstract, the phrase “at least on symptom of CHAPLE.” should read --at least one symptom of CHAPLE.--

In the Claims

In Claim 1, Column 99, Line 9, “administering an effect amount of a composition” should read --administering an effective amount of a composition--

Signed and Sealed this
Twelfth Day of August, 2025

Coke Morgan Stewart
*Acting Director of the United States Patent and Trademark Office*